US009953650B1

(12) United States Patent
Falevsky

(10) Patent No.: US 9,953,650 B1
(45) Date of Patent: Apr. 24, 2018

(54) SYSTEMS, APPARATUS AND METHODS FOR USING BIOFEEDBACK FOR ALTERING SPEECH

(71) Applicant: Louise M Falevsky, Rancho Palos Verdes, CA (US)

(72) Inventor: Louise M Falevsky, Rancho Palos Verdes, CA (US)

(*) Notice: Subject to any disclaimer, the term of this patent is extended or adjusted under 35 U.S.C. 154(b) by 0 days.

(21) Appl. No.: 15/530,169

(22) Filed: Dec. 8, 2016

(51) Int. Cl.
*G10L 15/22* (2006.01)
*G06F 3/01* (2006.01)
*G10L 15/18* (2013.01)
G10L 25/66 (2013.01)
A61B 5/00 (2006.01)

(52) U.S. Cl.
CPC .............. *G10L 15/22* (2013.01); *G06F 3/016* (2013.01); *G10L 15/1822* (2013.01); *A61B 5/486* (2013.01); *G10L 25/66* (2013.01); *G10L 2015/225* (2013.01); *G10L 2015/227* (2013.01)

(58) Field of Classification Search
CPC ...................................................... G10L 15/22
See application file for complete search history.

(56) References Cited

U.S. PATENT DOCUMENTS

| 5,647,834 A | 7/1997 | Ron |
| 5,722,418 A | 3/1998 | Bro |
| 6,001,065 A | 12/1999 | DeVito |
| 6,151,571 A | 11/2000 | Pertruskin |
| 6,255,937 B1* | 7/2001 | Hamaguchi ........... B06B 1/0215 340/384.7 |
| 6,425,764 B1 | 7/2002 | Lamson |
| 6,450,820 B1 | 9/2002 | Palsson |
| 6,728,680 B1* | 4/2004 | Aaron ..................... G10L 21/06 434/185 |
| 7,805,486 B2* | 9/2010 | Hering .................. H04Q 11/04 709/204 |
| 7,933,226 B2 | 4/2011 | Woodruff |
| 8,062,129 B2 | 11/2011 | Pope |
| 8,131,750 B2 | 3/2012 | Bathiche |
| 9,173,567 B2 | 11/2015 | Jain |
| 9,292,858 B2 | 3/2016 | Marci |
| 9,324,096 B2 | 4/2016 | Higgins |
| 9,374,394 B2 | 6/2016 | Kahn |
| 2002/0010587 A1 | 1/2002 | Pertrushin |
| 2002/0143241 A1 | 10/2002 | Thorell |
| 2004/0001616 A1* | 1/2004 | Gutta ..................... G06Q 30/02 382/118 |
| 2006/0224430 A1* | 10/2006 | Butt ............... G06Q 10/063116 705/7.16 |
| 2009/0225971 A1* | 9/2009 | Miller .............. H04M 3/42153 379/202.01 |

(Continued)

*Primary Examiner* — Jialong He
(74) *Attorney, Agent, or Firm* — Fish IP, Law

(57) ABSTRACT

Biofeedback is used to alter subsequent speech of one or more participants engaged in a discussion. Biofeedback signals can range from simplistic (beeps, flashes, vibrations, etc.) to more complicated images, videos, and music. In one aspect, feedback signals can be rendered to the participant(s) based on the extent to which the discussion relates to one or more goals. Signals can be rendered in any suitable manner, including a visual image rendered by a virtual reality headset or other device, an electronically generated auditory sound, other tactilely perceptible vibrations or other movements, preferably in substantially near real-time.

22 Claims, 17 Drawing Sheets

(56) References Cited

U.S. PATENT DOCUMENTS

| | | | |
|---|---|---|---|
| 2009/0271438 A1* | 10/2009 | Agapi | G06Q 10/1095 |
| 2009/0299840 A1* | 12/2009 | Smith | G06Q 30/02 |
| | | | 705/14.19 |
| 2011/0038472 A1* | 2/2011 | Gartner | H04L 12/5815 |
| | | | 379/202.01 |
| 2011/0060591 A1* | 3/2011 | Chanvez | H04M 3/2281 |
| | | | 704/270 |
| 2011/0072362 A1* | 3/2011 | Denner | G06Q 10/109 |
| | | | 715/751 |
| 2011/0201899 A1 | 8/2011 | Price | |
| 2011/0201959 A1 | 8/2011 | Price | |
| 2011/0201960 A1 | 8/2011 | Price | |
| 2011/0225013 A1* | 9/2011 | Chavez | G06Q 10/10 |
| | | | 705/7.18 |
| 2012/0054281 A1 | 3/2012 | Westmoreland | |
| 2012/0123779 A1* | 5/2012 | Pratt | G10L 15/26 |
| | | | 704/235 |
| 2012/0172661 A1* | 7/2012 | Chiu | A61F 5/41 |
| | | | 600/38 |
| 2012/0323575 A1* | 12/2012 | Gibbon | G11B 27/28 |
| | | | 704/246 |
| 2014/0082100 A1* | 3/2014 | Sammon | G06Q 10/109 |
| | | | 709/206 |
| 2014/0316192 A1* | 10/2014 | de Zambotti | A61M 21/02 |
| | | | 600/28 |
| 2015/0110277 A1 | 4/2015 | Pidgeon | |
| 2015/0142082 A1* | 5/2015 | Simon | A61N 1/36053 |
| | | | 607/61 |
| 2015/0215351 A1* | 7/2015 | Barzuza | G06T 19/006 |
| | | | 715/757 |
| 2016/0077547 A1 | 3/2016 | Aimone | |
| 2016/0117624 A1* | 4/2016 | Flores | G06Q 10/06393 |
| | | | 705/7.39 |
| 2016/0171062 A1* | 6/2016 | Bufe | H04L 67/36 |
| | | | 707/722 |

* cited by examiner

SYSTEMS, APPARATUS AND METHODS FOR USING BIOFEEDBACK FOR ALTERING SPEECH

FIELD OF THE INVENTION

The field of the invention is biofeedback.

BACKGROUND

The following description includes information that may be useful in understanding the present invention. It is not an admission that any of the information provided herein is prior art or relevant to the presently claimed invention, or that any publication specifically or implicitly referenced is prior art.

Biofeedback is often described as using substantially near real-time feedback signals to modify autonomic physiological functions. For example, brain waves, heart rate, breathing rate, hand temperature etc. Some researchers have pushed the envelope further, to use substantially near real-time feedback signals to modify kinetic activities that are partially under voluntary control, for example, stuttering or other speech pathologies (Electronic anti-stuttering device providing auditory feedback and disfluency-detecting biofeedback U.S. Pat. No. 6,231,500 B1), intention tremors (Clinical Application of Biofeedback Treatment with a Microvibration Transducer, *Journal of Experimental & Clinical Medicine* Vol. 12 No. 5,6, pp, S19-324, 1987), cardiac arrhythmias (The Effects of Respiratory Sinus Arrhythmia Biofeedback on Heart Rate Variability and Posttraumatic Stress Disorder Symptoms: A Pilot Study, Zucker, T. L., Samuelson, K. W., Muench, F. et al. Appl Psychophysiol Biofeedback (2009) 34: 135. doi:10.1007/s10484-009-9085-2), incontinence (Effect of Adding Biofeedback to Pelvic Floor Muscle Training to Treat Urodynamic Stress Incontinence, Mørkved, Siv MSc, P T; Bø, Kari PhD, P T; Fjørtoft, Toril P T, Obstetrics & Gynecology: October 2002-Volume 100-Issue 4-p 730-739), temporomandibular disorders (Efficacy of Biofeedback-Based Treatments for Temporomandibular Disorders, Crider, A., Glaros, A. G. & Gevirtz, R. N. Appl Psychophysiol Biofeedback (2005) 30: 333. doi:10.1007/s10484-005-8420-5) to name a few.

Still other researchers have used biofeedback techniques to deal with some cognitive patterns. Among other things, biofeedback techniques have been used to treat fear or anxiety (Neurofeedback in the Treatment of Developmental Trauma: Calming the Fear-Driven Brain" by Sebern F. Fisher. W. W. Norton & Company, New York, N.Y., 2014, 416 pages, ISBN: 978-0-393-70786-1), attention deficit (Attention Enhancement System using Virtual Reality and EEG Biofeedback, B. H. Cho; J. M. Lee; J. H. Ku; D. P. Jang; J. S. Kim; I. Y. Kim; J. H. Lee; S. I. Kim, Virtual Reality, 2002. Proceedings. IEEE), alcohol abuse (Sobriety Outcome After Alcoholism Treatment with Biofeedback Participation: A Pilot Inpatient Study, International Journal of the Addictions, M. R. Denney, Jarod L. Baugh & Henry D. Hardt, Volume 26, 1991-Issue 3, Pages 335-341), smoking (Sampling of empirically supported psychological treatments from health psychology: Smoking, chronic pain, cancer, and bulimia nervosa, Compas, Bruce E.; Haaga, David A. F.; Keefe, Francis J.; Leitenberg, Harold; Williams, David A., Journal of Consulting and Clinical Psychology, Vol 66(1), February 1998, 89-112.), insomnia (Biofeedback and Progressive Relaxation Treatment of Sleep-Onset Insomnia: A Controlled, All-Night Investigation, Robert Freedman and James D. Papsdorf, Biofeedback and Self-Regulation, VoL 1, No. 3, 1976.), pain (Pain management in rheumatoid arthritis patients, Parker, J. C., Frank, R. G., Beck, N. C., Smarr, K. L., Buescher, K. L., Phillips, L. R., Smith, Ed., Anderson, S. K., Walker, S. E., Arthritis & Rheumatology, Volume 31, Issue 5, May 1988, Pages 593-601.), and socially undesirable behaviors, as in for example, aggressive thoughts of sexual predators (Sexual recidivism among child molesters released from a maximum security psychiatric institution, Rice, Mamie E.; Quinsey, Vernon L.; Harris, Grant T., Journal of Consulting and Clinical Psychology, Vol 59(3), June 1991, 381-386.).

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Despite all of this focus on disease amelioration and psychophysical therapies, it appears that biofeedback has never been applied to assist with more everyday, common experiences, including for example guiding business meetings (Dynamic media augmentation for presentations, US 20090327896 A1.), assisting with invention brainstorming sessions ((Effects of Simulated Biofeedback and Human Monitoring on Brainstorming Performance, Graham, William K., The Journal of Social Psychology, Volume 101, 1977-Issue 1, Pages 139-143.), mediating disputes, helping people get to know each other, accelerate their learning (Electroencephalograph based biofeedback system for improving learning skills, U.S. Pat. No. 6,626,676 B2.), and providing guidance with respect to other goal oriented discussions.

Biofeedback has also apparently not taken advantage of artificial intelligence (AI) systems, which can conceivably be used to guide the feedback signals.

AI has been employed to assist humans in cognitive functioning, but not using biofeedback. For example, the CALO (Cognitive Assistant that Learns and Organizes) project funded by the Defense Advanced Research Projects Agency (DARPA) has facilities for organizing and prioritizing information, preparing information artifacts, mediating human communications, task management, scheduling and reasoning, and allocating resources. Spin-offs from this project include Siri™ (now an Apple™ product), Social Kinetics, a social application that learned personalized intervention and treatment strategies for chronic disease patients; the Trapit project, which is a web scraper and news aggregator that makes intelligent selections of web content based on user preferences; Tempo AI, a smart calendar, Desti, a personalized travel guide; and Kuato Studios, a game development startup. Yet because CALO applications don't utilize biofeedback, they cannot provide substantially at least near real-time feedback to human users who are seeking cognitive assistance; especially during an interactive discussion.

Thus, although some technologies utilize biofeedback, other technologies assist humans in cognitive functioning, and still other technologies use AI, it appears that no one has so far figured out how to utilize biofeedback to assist humans in their cognitive functioning, let alone using both biofeedback and AI to assist humans in their cognitive functioning.

SUMMARY OF THE INVENTION

The inventive subject matter provides systems, apparatus, and methods in which biofeedback is used to assist humans in their cognitive functioning.

Of particular interest are embodiments where biofeedback assists in altering subsequent speech of participants engaged in a discussion. Preferred embodiments in that regard include the steps of categorizing content and/or an expression characteristic of a participant's speech, generating a feedback signal corresponding to the categorization, and rendering the feedback signal to the participant during the discussion.

Feedback signals can advantageously be provided to the participant in any suitable manner, including for example, a visual image rendered by a virtual reality headset or other device, an electronically generated auditory sound, rendered through earphones or speakers, other tactilely perceptible vibration or other movement. Feedback signal might or might not have sufficient intensity to elicit a perceptible pain response from the participant. Feedback signals are preferably rendered to the participant in substantially near real-time relative to a time in which the portion of speech was produced.

Contemplated systems and methods might or might not utilize specialized biofeedback equipment. Such equipment can be used as an input device from the participant into a Biofeedback Discussion System as in cameras, eye tracking devices, pupil dilation detection devices, microphones, skin temperature detection devices, skin pore size detection devices, skin moisture detection devices, brainwave detection devices, heart rate detection devices, or respiratory detection devices. Other biofeedback equipment can be used as an output or rendering device from the Biofeedback Discussion System to the participant including but not limited to visual displays, stationary or wearable (headset) speakers, aromatherapy devices, and devices that produce vibration effects including smartphones, vibrating furniture (chairs), or wristbands. Some biofeedback wristband devices may introduce a mild shock signal. One piece of equipment that is thought to be valuable is an augmented reality headset. Such headsets could convey composite images to the participant(s), including for example (a) a representation of another participant providing a portion of the discussion information, and at least one of (b1) a representation of profile information about the other participant, and (b2) a rendering of the multiple categorizations and their respective rankings.

In some embodiments, at least some of the speech in a discussion is conveyed to an artificial intelligence system ("AI system"), which then replies with one or more categorizations of topics or ideas or expression characteristics that the AI system derives from the discussion. In such instances, biofeedback to the participant(s) is advantageously related to the extent to which the discussion over some period of time relates to one of inure goals, of one or more participants. AI systems contemplated to be suitable for this use include IBM™ Watson™ and Google's™ Deep Mind™.

In embodiments involving discussions, there are at least two aspects of goals that can be tracked. One aspect is endpoint satisfaction—how well (or poorly) the discussion is satisfying the stated goal(s). Another aspect is topic relevance—the extent to which the discussion information over a period of time relates to the categorization concepts. Thus, a meandering discussion might score high on endpoint satisfaction, but low on topic relevance.

In some embodiments, multiple categorizations are received from the AI system, along with relative rankings, and both the multiple categorizations and the relative rankings are rendered to the participant or participants using the system, via word clouds, charts, graphs, lists or any other suitable visual, auditory, tactile, or other means.

For embodiments involving a discussion, additional participants in the discussion might or might not be humans, and where they are humans, feedback signals can also be administered to those other participants. Consider two inventors are engaged in a discussion over a long distance, communicating via any a suitable communication means, including for example, a telephone, WebEx™, Skype™, Snapchat™, or Slack™. They also use any suitable device(s) set up for biofeedback input and output, and interact with a human-machine interface. Contemplated such devices include one or more of a mobile phone, a computer monitor, and a VR or VR/AR headset.

Before the discussion starts, necessary information, and possibly goals, are input to a machine of a preferred embodiment of the present invention, which in turn communicates with an AI system. Once the discussion starts, a portion of the first participant's speech contents is captured and suitably transformed, perhaps using audio-to-text software. Characteristics of the speech, such as pitch or tone of the speaker, are identified. The contents and characteristics are sent to the machine and also to the AI system, which produce categorizations. From the categorizations, feedback signals are generated. And then the feedback signals cause biofeedback devices to render various signals to the participants. Among other things, the rendering can include indications on the extent to which goals are being met. Where participants react to the rendering, such reactions can be used to help alter the participants' subsequent speech.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
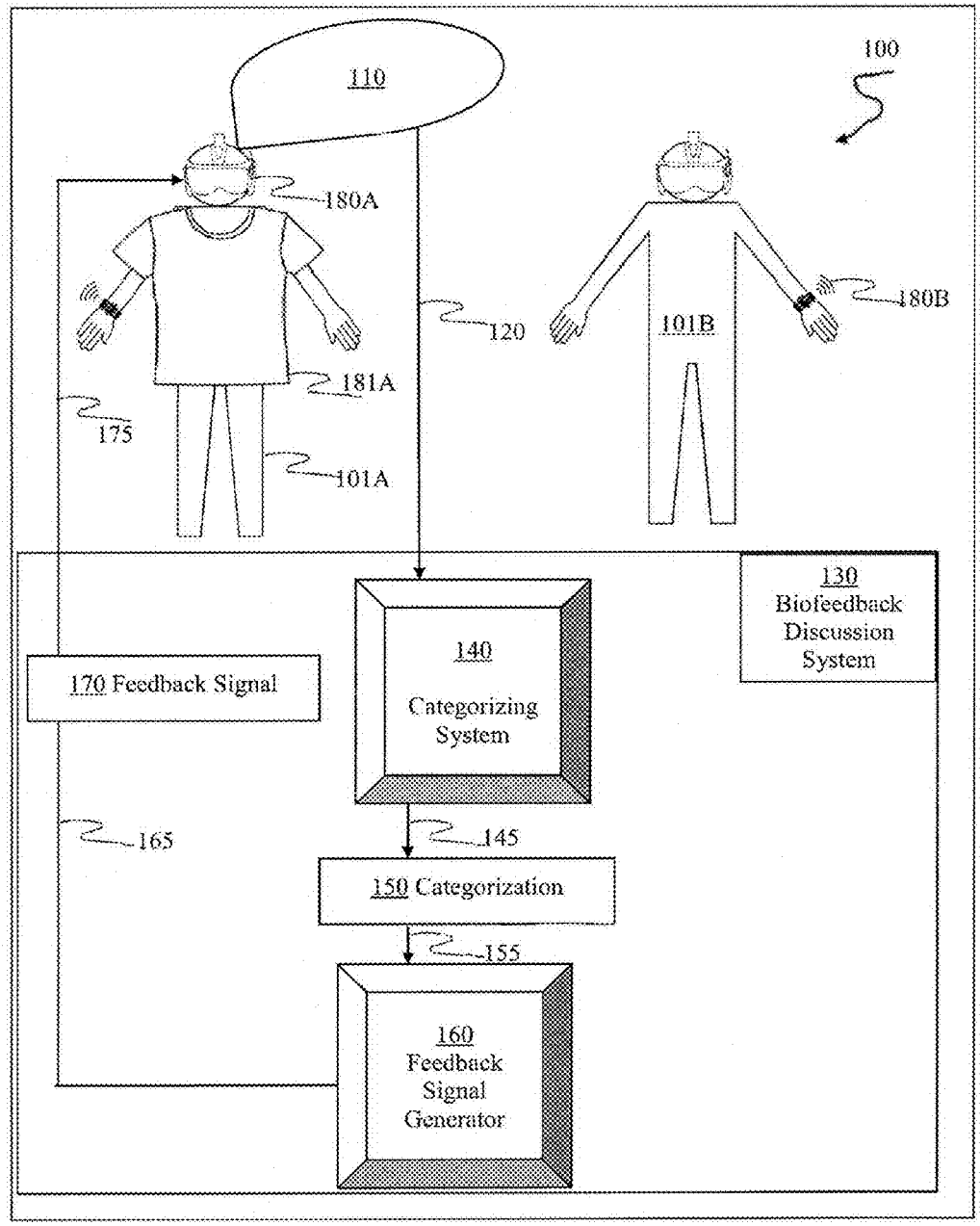
FIG. 1 is a diagram of two participants engaged in a discussion with each other, where the discussion is captured by a Biofeedback Discussion System, a categorization is derived, a response to the participants is generated by a Feedback Signal Generator, and the response is rendered to the participants.

In some embodiments, the numbers expressing quantities of ingredients, properties for example concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Throughout the following discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

As used herein, the term "biofeedback" means using electronics to monitor a physiological function of a person, and using the acquired information to provide a signal to the person, in substantially near real-time, with a goal of assisting the person to alter the function. Contemplated physiologic functions include brainwaves, muscle tone, skin conductance, heart rate, breathing, and speech. The alteration of function could be conscious or unconscious.

As used herein, the term "speech" means verbal expressions using a communication, whether rendered auditorily, through typing, sign language, or any other manner, plus hand gestures or other expression characteristics, which are considered herein to have no commonly accepted, specific language equivalent. As used herein, the term "expression characteristics" include, for example, facial expressions, hand motions, eye movements, and body movements, to the extent that they have communicative meaning.

As used herein, the term "content of a portion of the speech" means the subject matter of the speech, divorced from an auditory tone. This includes, for example, the words used in the speech.

As used herein, the term "discussion" means an exchange of opinions with respect to a topic. Discussion excludes a purely factual question and answer session, in which no opinions are expressed. If one person asks "where do you live?" and another person answers "125 Main Street", that's not a discussion. If one person asks "Where would you like to go to dinner?" and the other person answers "It's too late to go to dinner", then the exchange would be construed as a discussion. Thus, engaging in a verbal exchange in order to reach a decision or debate an idea would be considered a discussion.

As used herein, the term "near real-time" with respect to a triggering event and a response event means that the time between the triggering and response events is no more than 5 seconds. Also as used herein, "substantially near real-time" means no more than a minute, including for example, less than 30 seconds, less than 20 seconds, and less than 10 or 5 seconds.

As used herein, the term "categorization" means the process in which ideas and objects are recognized, differentiated, and understood. Categorization implies that ideas and/or objects are grouped into categories, usually for some specific purpose.

As used herein, the term "artificial intelligence system" means a system that provides responses derived by a system that simulates human intelligence by learning and/or making inferences.

As used herein, the term "biosignal" means any signal in a living being that can be measured and monitored. Biosignals can be bioelectrical signals, but they can also be electrical and non-electrical signals.

As used herein, the term "gesture" means a movement of the hands, face, or other parts of the body that communicates a non-verbal message.

As used herein, the term "stipulation" is a condition or requirement that is specified or demanded as part of an agreement.

As used herein, the term "listen" is to pay attention to someone or something in order to hear what is being said, sung, played, typed, or emitted.

As used herein, the term "talk-time" means the amount of time that a participant has contributed a portion of speech (talked) during the discussion.

As used herein, the term "includes" means "includes, but not limited to".

The technical problem being addressed is how to use electronics to help humans to achieve goal-based objectives, especially during discussions. The technical solution is to apply biofeedback signals to the participants, based upon substantially near real-time analysis of their contributions and reactions to the discussion(s). In some embodiments at least some of the biofeedback signals are derived in part using output from an AI System.

From another perspective, one could say that the technical effects include software: (1) that contains a human-machine interface with various settings so that humans can provide information to devices; (2) that deploys audio-to-text software; (3) that generates categorization; (4) that generates feedback signals; (5) that renders feedback signals; (5) that drives biofeedback devices; (6) that creates a software robot (i.e., a BOT or system software agent).

Such software could be completely or partially resident on a device, or completely or partially resident on a different device, or completely or partially resident on the server, or completely or partially resident on the devices that interact with the users.

From still another perspective, one could say that the technical effects include hardware: (1) that optimizes the rendering of feedback signals on computer monitors and mobile phones and VR headsets; (2) that is wearable computing device that preferred combines both biofeedback input and biofeedback output.

One should also appreciate that the technical effects include combining such software with hardware, which could be combined in middleware and/or microchips.

FIG. 1 generally includes first and second participants 101A, 101B involved in a discussion, a portion of speech 110, a categorizing system 140, a categorization 150, a feedback signal generator 160, a feedback signal 170, a VR headset 180A, a T-shirt embedded with sensors 181A, and a notification wristband 180B. A Biofeedback Discussion System 130 comprises the categorization system 140, the categorization 150, the feedback signal generator 160, and the feedback signal 170; the Biofeedback Discussion System 130 labeled here to simplify system descriptions. Communication lines carry speech 120, a categorization 145 and 155, a feedback signal 165, and a rendering 175. The categorizing system receives text, video and/or audio of a portion of the discussion, and categorizes that portion. The feedback signal generator instructs the signal generator to produce a feedback signal based upon the categorization, the VR headset renders the feedback signal to participant 101A, and the notification wristband 180B renders the signal to participant 101B via a wireless connection.

Both participants 101A and 101B are humans, but it is also contemplated that one of them could be a system software agent or other non-human. It is also contemplated that more than two participants could take part in the discussion, e.g., 301A-301N. Participant 101A is wearing a T-shirt with embedded sensors e.g., 1680 that output biosignals of heart rate and breathing rate for participant 101A. The extracted biosignals from participants 101A and 101B are used by the categorizing system 140 as part of the portion of speech to be categorized. Participants 101A and 101B are both wearing VR goggles e.g., 1730 and notification wristband e.g. 1780 that are used to render the feedback signal 170.

A portion of speech 110 is extracted from the participant 101A and 101B discussion by the Biofeedback Discussion System 130. The Biofeedback Discussion System 130 "listens" to the discussion. The portion of speech that is extracted from the discussion is based on particular words or phrases that are pertinent to the discussion for a specific embodiment domain.

The categorizing system 140 is a component of the Biofeedback Discussion System 130. The categorizing system listens to the discussion to extract the portion of speech 110 that includes participant discussion contents and expression characteristics. The categorizing system then uses an AI System, for example IBM™ Watson™, to identify a characterization. IBM™ Watson™ is an example of an appropriate AI System that analyzes speech (including the speech and/or text) for keywords, concepts, relationships, taxonomy, classification, personality attributes, tone of voice to name some of the Watson™ AI System capabilities.

The categorization 150 is an output from the categorizing system 140. The characterization is identified by IBM™ Watson™ or other AI System. The characterization 150 that has been identified by the AI System is modified by the categorizing system 140 to select the appropriate elements of categorization that are relevant to the participants' 101A and 101B discussion. Relevant elements of categorization are dependent on the embodiment domain and may include the percentage confidence of relevance determined by the AI System, the matching of keywords, concepts, personality attributes, and tone of voice to participant 101A and 101B profiles, and additional ontological and taxonomic classification applied to the elements of categorization. The categorization also includes elements of biosignals that have been extracted from participants 101A and 101B as part of the extracted portion of speech. Biosignals from participants 101A and 101B are captured by any number of biosignal capture devices e.g., 1610, 1620, 1630, 1640, 1650, 1660, 1670, or 1680.

The feedback signal generator 160 is a component of the Biofeedback Discussion System 130. The feedback signal generator uses the categorization 150 and generates a feedback signal 170 corresponding to that categorization. A correspondence between the categorization and the feedback signal is determined by the embodiment domain and the specific participants 101A and 101B having the discussion. A correspondence determination can include but is not limited to the goals, profiles, prior discussions, and biosignals of participants 101A and 101B.

In FIG. 1, the feedback signal is an output from the feedback signal generator 160. The feedback signal can be visual, aural, olfactory, or tactile data elements that will be rendered to the participants 101A and 101B. The feedback signal can also take the form of direct instruction to the rendering devices in order to generate renderings to participants 101A and 101B.

The feedback signal 170 is shown as being rendered by VR headset 180A (also e.g., 1730). Additionally or alternatively, the signal could be rendered by any number of other rendering devices e.g., 1710, 1715, 1720, 1725, 1735, 1740, 1745, 1750, 1755, 1760, 1770, 1775, or 1780. This feedback signal rendered by the VR headset 180A can alter the subsequent speech of participant 101A.

Biofeedback discussion system 130 receives input from participants 101A and 101B via communication line 120 into the categorizing system 140. The communication lines could be Internet, WiFi, Bluetooth, near-field, or telecommunications bands or any combination of line/radio, simplex/duplex, analog/digital, or baseband/carrier communication systems. The preference being the Internet coupled with telecommunications bands enabled by standardized protocols to send portions of speech and biosignals over any distance.

Communication lines 145 and 155 carries information from categorizing system 140 to the feedback signal generator 160. Again, the communication lines could be Internet, WiFi, Bluetooth, near-field, or telecommunications bands or any combination of line/radio, simplex/duplex, analog/digital, or baseband/carrier communication systems. The preference being the Internet coupled with telecommunications bands enabled by standardized protocols to send portions of speech and biosignals over any distance.

Rendering communication lines 165 and 175 carries rendering signals or instructions 170 to the VR headset 180A. Again, the communication lines could be Internet, WiFi, Bluetooth, near-field, or telecommunications bands or any combination of line/radio, simplex/duplex, analog/digital, or baseband/carrier communication systems. The preference being the Internet coupled with telecommunications bands enabled by standardized protocols to send portions of speech and biosignals over any distance. Depending on the device(s) used for rendering the long-haul communication lines 165 and 175 that may be Internet and/or other telecommunications bands may be converted to localized communication lines including but not limited to WiFi, Bluetooth, near-field, or other proximity based communication systems.

VR headset 180A is worn by participant 101A over the eyes. The VR headset provides digital feedback signals for the participant to use during the discussion. The VR headset may provide all the feedback signals corresponding to the categorization for participant 101A or the VR headset may be used in conjunction with other rendering devices e.g., 1710, 1715, 1720, 1725, 1735, 1740, 1745, 1750, 1755, 1760, 1770, 1775, or 1780.

Notification wristband 180B worn by participant 101B is not actively in use in this diagram. The notification wristband is an example of a rendering device that can be used by participants.

T-shirt with embedded sensors 181A is worn by participant 101A. The T-shirt sensors detect the heart rate and respiratory rate of participant 101A. The participant 101A biosignals detected by the T-shirt sensors are communicated into the categorization system via an intermediary device; for example a smartphone application. The biosignals captured by the smartphone application are sent via communication line 120 to the categorizing system.

Figure 2:
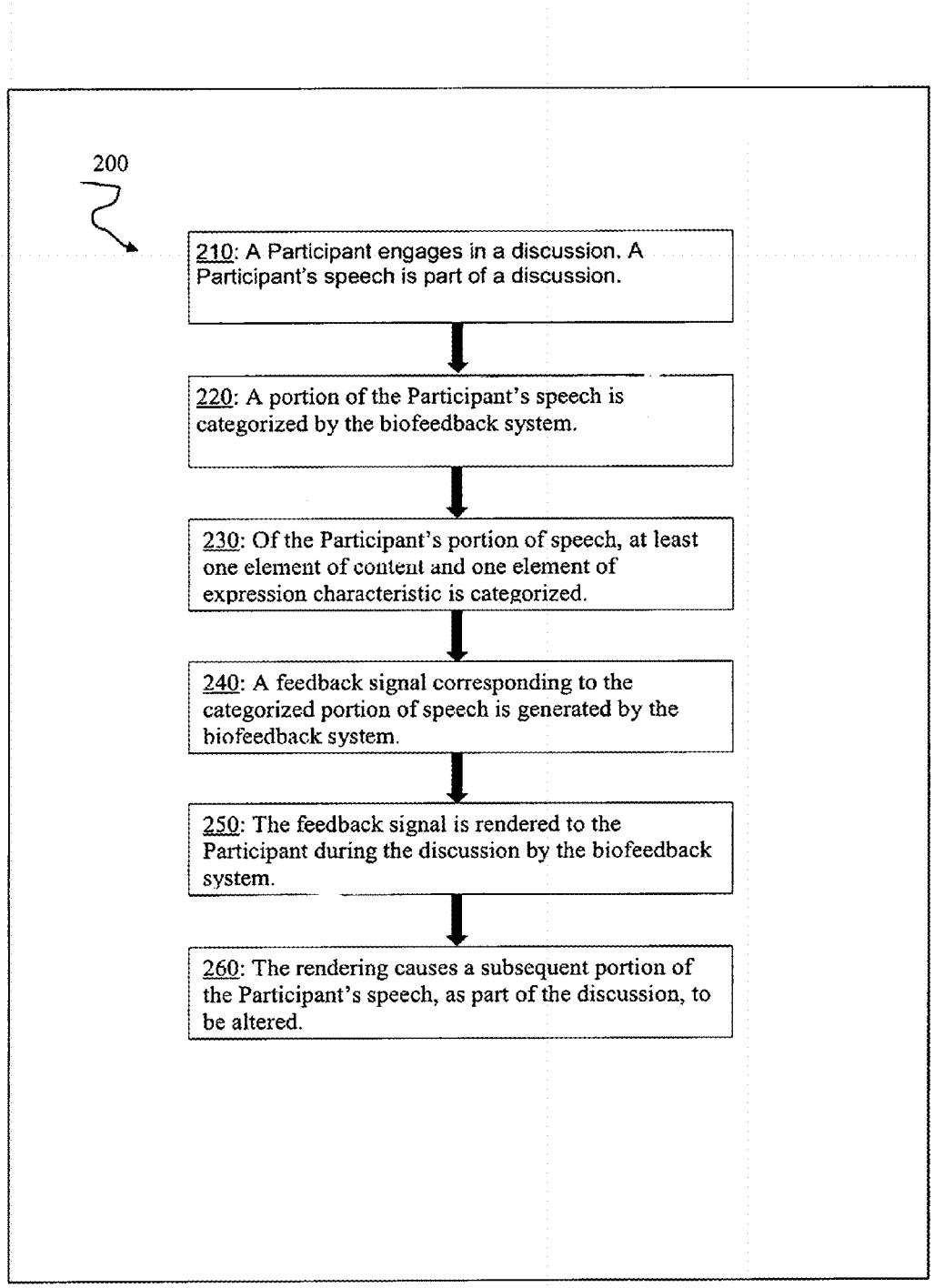
FIG. 2 is a flowchart of interactions between the participants and the Biofeedback Discussion System depicted in FIG. 1.

FIG. 2 is a flowchart 200 depicting steps taken by the Biofeedback Discussion System e.g. 130 in FIG. 1 that extracts a portion of speech from the participant, categorizes that portion of speech including at least one content and an expression characteristic, identifies a categorization, generates a feedback signal corresponding to the categorization, and renders the feedback signal to the participant, altering the participant's subsequent speech during a discussion.

At step 210, the participant enters into a discussion. The discussion takes place between two or more participants who may be located in proximity or distributed geographically (in different locations). All participants discuss in an environment that can be absorbed digitally such that they are using microphones, cameras, or other speech and or video devices that can capture their voice and possibly their image and/or they are using textual input that is digitized. Participant's speech, including visual and textual inputs, are accessible to the Biofeedback Discussion System via communication links to all participants.

In FIG. 2, the participants can access the system's digital realm via any device that enables a digital signal to be sent to the Biofeedback Discussion System, and a feedback signal to be rendered to the participant and allows for remotely connecting to other participants, including but not limited to, a mobile device including but not limited to a mobile phone, tablet, or WiFi enabled computing device, an internet wired computer or terminal, or other communication connection.

In FIG. 2, one or more participants may elect to also include in a discussion an AI embodiment of a participant; a system software agent or BOT. This AI embodiment can be trained prior to use by the participants to respond to the human participants on topics, and in manners that are meaningful within the particular embodiment domain where they are used.

Focusing back on FIG. 2, at step 210, a discussion is composed of multiple participants' "speech", as defined herein.

The "expression characteristic of a portion of the speech" is preferably derived analyzing data from one or more sensors. For example, an expression characteristic of yelling could be obtained by measuring a decibel level of the speech as received by a microphone. Similarly, an expression characteristic of "accusation" could be obtained by analyzing images for hand, facial and body gestures, as received by a camera.

At step 220, a portion of the participant's speech is selected for categorization by the Biofeedback Discussion System.

Also at step 220 in preferred embodiments, the selection of the participant's speech is performed by Biofeedback Discussion System triggers (predetermined system settings that watch for particular events to occur and then act on those events) that monitor all of the participant's speech and then selects a portion of that participant's speech when a threshold for a particular event has been reached. The speech threshold that triggers the portion of speech that is then selected is dependent on the embodiment domain but can include words of perception, words of disagreement or agreement, words of confusion, words matching topics selected by discussion participants, and words that are within or outside the particular subject matter of the participant's discussion to name a few types triggers in various domains.

At step 230, the portion of the participant's speech containing word content, and the expression characteristic of that word content, is categorized by the Biofeedback Discussion System. The Biofeedback Discussion System includes at least an AI system that enables categorizing input by means of weighted scoring of keywords, concepts, relationships, taxonomy classification, personality attributes, as well as the underlying tone of voice used either aurally, in textual word content, or both.

At step 240, the Biofeedback Discussion System generates a feedback signal that corresponds to the portion of the participant's speech that has been captured. The feedback signal correspondence pertains to the categorization weighting of the attributes considered for the particular domain embodiment and the speech expression characteristic analysis.

Also at step 240, the feedback signal can take the form of a sound, a vibration, a smell, or a textual or other visual message.

At step 250, the feedback signal is rendered to the participant during the discussion. The feedback signal corresponding to the categorized portion of speech is rendered to the participant in a substantially near real-time manner (and preferably in near real-time) such that the participant finds the feedback signal information relevant to the current discussion that has continued during the time of the categorization and rendering of the feedback signal.

Also at step 250, the feedback signal can be rendered for some participants and not others, for only one specific participant, or for all participants depending on the embodiment domain.

At step 260, by the means of rendering the feedback signal to the participant and the participant noticing the rendered feedback signal, the participant will react to that signal and either mention the content of the feedback signal to other discussion participants, take note of the feedback signal and add the new information into the discussion, or the participant will realize that the feedback signal is one that encourages a change in the subsequent content or expression characteristic of that participant's speech and alter their subsequent speech accordingly. The feedback signal is rendered to the participant in such a way that the participant can incorporate the feedback signal information into their subsequent thoughts and actions.

Figure 3:
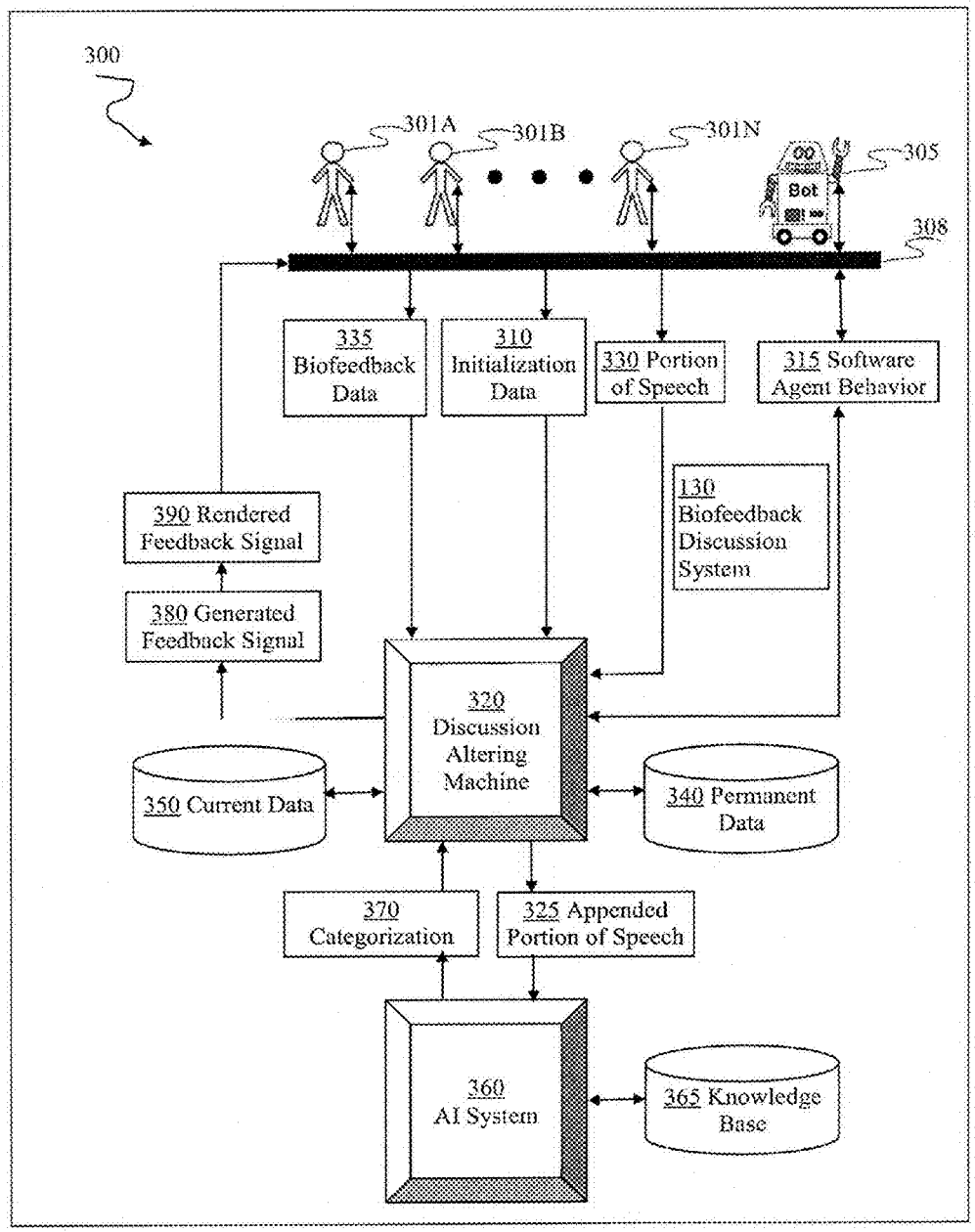
FIG. 3 is a diagram of the Biofeedback Discussion System of FIG. 1, operating with respect to N participants. In this rendering, the functions of Categorizing System 140 (from FIG. 1) are split between a Discussion Altering Machine 320 and an AI System, and the functions of the Feedback Signal Generator 160 (from FIG. 1) are satisfied by the Discussion Altering Machine 320.

FIG. 3 is a diagram of interactions among participants and the Biofeedback Discussion System e.g., 130. FIG. 3 depicts flow of information from participants into the Discussion Altering Machine, the system categorization process by the AI System, and generation and rendering of a feedback signal to the participant(s). Also shown are data storage systems used by the Discussion Altering Machine and AI System, and the interaction of the software agent behavior.

The diagram shows multiple participants 301A, 301B . . . , 301N providing initialization data 310, a portion of speech 330 e.g., 110, and biofeedback data 335 into the Discussion Altering Machine 320. Participants 301A, 301B, . . . 301N are persons, but 301A e.g., 101A could be the only person contributing initialization information 310, a portion of speech 330, and biofeedback data 335 into the Discussion Altering Machine 320.

A rendering of a visual avatar (or BOT) 305 is representing a system software agent behavior 315 driven by the Discussion Altering Machine 320. The system software agent behavior 315 includes asking participants to vote on a particular topic, assisting in goal setting to align participant goals into a group goal that satisfies the SMART goal definition of Specific, Measurable, Attainable, Relevant, and Time-Bounded characteristics, detecting confusion, lack of knowledge, or topic clarity on the part of a participant 301A, 301B, . . . 301N, responding to specific questions posed by a participant, commenting or reminding participants of their progress in time or towards a goal or agenda list completion that has been set as a target for the discussion, and other facilitation or mentoring behaviors that differ depending on the domain of the embodiment, for example, inventors with BOT exhibiting such facilitation or mentoring behaviors, dispute mediation with mediator, dating with matchmaker, education with teacher or professor, conferences with a business consultant, and meetings with a business person.

The communication link 308 between the participants 301A, 301B, . . . 301N and the Discussion Altering Machine 320 enables participants to communicate with each other and with the Discussion Altering Machine 320. Communication link 308 can operate over any remote digital connection protocol, including but not limited to, the Internet, WiFi, Bluetooth, near-field, or telecommunications bands.

In FIG. 3, the Biofeedback Discussion System e.g., 130 is enclosed by a box. This box encompasses the components and operations of the Biofeedback Discussion System e.g., 130. The box in this diagram demonstrates the relationship between the operations of the Biofeedback Discussion System e.g., 130 and the expanded detail of that system in FIG. 3.

Initialization Data 310 is entered by each participant 301A, 301B . . . 301N that includes personal profile information, related documents, and their goal for the discussion via a web interface form into the Discussion Altering Machine 320 as a step in initializing the starting point for the discussion. The personal profile, related documents, and goal information will vary according to the specific domain embodiment and will be described in greater detail in each embodiment herein.

The portion of speech 330 is emitted by the human participants 301A, 301B . . . 301N, during the discussion. The Discussion Altering Machine 320 monitors all of the participants' speech and then selects a portion of that participant's speech when a threshold or trigger (predetermined system settings that watch for particular events to occur and then act on those events) for a particular event has been reached. The Discussion Altering Machine 320 then captures the portion of speech 330 around the trigger word or phrase. The speech threshold that triggers the portion of speech 330 that is then captured is dependent on the embodiment domain but can include words of perception, words of disagreement or agreement, words of confusion, words matching topics selected by discussion participants, and words that are within or outside the particular subject matter of the participant's discussion to name a few types triggers in various domains.

Biofeedback data 335 includes the human participant 301A, 301B . . . 301N biosignals emitted during the discussion. All available biosignal data from each participant 301A, 301B . . . 301N is monitored by the Discussion Altering Machine 320. Periodically during the discussion, each participants' 301A, 301B . . . 301N biofeedback data is taken as input to the Discussion Altering Machine and is analyzed by that machine to produce discrete data points for rendering to the participants 301A, 301B . . . 301N. Biofeedback data 325 available to the Discussion Altering Machine includes but is not limited to eye movement, pupil dilation, facial expression, voice loudness and tone, body gestures or movement as in wriggling, arm raising or waving, finger pointing, and standing, heart rate, respiratory rate, body temperature especially of the hands, pore size and sweat gland activity, and brain activity.

The Discussion Altering Machine 320 consists of one or more digital processing machines (computers or servers containing CPUs, GPU, or other instruction processing device). The instructions this digital device executes (a) manage the permanent and current data storage devices input and output, (b) determine realizable goals using SMART (Specific, Measurable, Attainable, Relevant, and Time-Bounded) analysis, (c) listen to the participants' 301A, 301B . . . 301N discussion and, using the particular embodiment's requirements, (d) capture a portion of a participant's speech as input to the AI System for analysis, (e) analyze the AI System 360 categorization for rendering to the participants, (f) generate an appropriate feedback signal for one or more or all participants, (g) render the feedback signal corresponding to the AI System 360 categorization to one or more or all participants, (h) forward participant questions to the AI System and return information links to answer the participant's question to the participants, manage all software agent (BOT) behavior including answering questions, (i) request participant votes on specific topics, (j) monitor participant's discussion for goal achievement with respect to content, (k) cover agenda items, and in elapsed time of a discussion, and other mentoring behaviors dependent upon the domain embodiment, (l) intake participants' initialization data 310 including but not limited to profiles, documents, goals or needs, and discussion metadata and storing them in permanent and current data storage as appropriate, (m) manage participant discussion connection session information, (n) intake biosignal data from participants' 301A, 301B . . . 301N personal digital monitors to track some or all, but not limited to voice loudness, use of big or complex words in the discussion, the rapidity of a participant's speech, heart rate, breathing rate, participants' body temperature, eye movements, (o) manage discussion administration by storing discussion artifacts including but not limited to a discussion transcript, discussion agenda, and (p) record of discussion participants, their goals, profiles, and documents contributed, and other artifacts created during the discussion including but not limited to diagrams, lists, documents, or spreadsheets as an in-exhaustive list of examples.

Output from the Discussion Altering Machine 320 provides an internally generated feedback signal 380 corresponding to the AI System 360 categorization. The generated feedback signal 380 is then used by the Discussion Altering Machine 320 to formulate an appropriate rendering of that generated feedback signal 380 to the participants 301A, 301B . . . 301N. Other outputs rendered by the Discussion Altering Machine 320 include information links as answers to questions posed by the participants 301A, 301B . . . 301N and answered by the AI System 360 and software agent behavior 315 embodied in an avatar 305 visible to the participants 301A, 301B . . . 301N.

The appended portion of speech 325 is the portion of speech that has been appended by the Discussion Altering Machine 320. The portion of speech 330 is captured as intake from the participants' discussion, has been prepared by the Discussion Altering Machine 320, and is forwarded on to the AI System 360. The appended portion of speech 325 may be the same as the participants' captured portion of speech 330 or it may be appended by the Discussion Altering Machine 320 with relevant information. Information relevant to the portion of speech 330 may include but is not limited to participant 301A, 301B . . . 301N profile characteristics (a subset of participant profile information submitted as initialization data 310 as well as participant profile information that is contained in the permanent data storage and is deemed relevant to the participant discussion), participant 301A, 301B . . . 301N documents from the initialization data 310 (a subset of participant documents submitted as initialization data 310 as well as participant documents that are contained in the permanent data storage and is deemed relevant to the participant discussion), and any other relevant information contributed by discussion participants 301A, 301B . . . 301N either prior to the discussion in the initialization data 310 or contributed prior to the discussion and stored in the permanent data storage.

The AI System 360 has capabilities that include learning, reasoning, problem-solving, perception, and language understanding, delivering intelligent capabilities of deriving logical analysis and relationship associations that have not been explicitly programmed into the AI System. IBM™ Watson™ is an example of an appropriate AI System because it analyzes speech (including the speech and/or text) for keywords, concepts, relationships, taxonomy, classification, personality attributes, tone of voice to name some of the Watson™ AI System capabilities. Here we discuss the use of Watson™ as an AI system capable of categorizing 370 an appended portion of speech 325, but other AI systems delivering the same or more capabilities can also be used in domain embodiments. Other functions of the AI System 360 include contributing to the software agent behavior 315, and providing answers to participant 301A, 301B, . . . 301N questions in the form of web links (HTML locations accessible via the HTTP protocol) to web pages that contain the answer to the question posed by the participant.

The knowledge base 365 depicts the internal data structures and data contents of the AI System 360. Data structure organization particular to the AI System 360 is not included here as it is a component of the out-of-the box AI System 360. Different domain embodiments will employ different configurations of an AI System depending on the particular domain of the embodiment, but all embodiments will require ontologies, taxonomies, semantics, controlled vocabularies, knowledge graphs, statistical models, and domain specific content to be learned by the domain embodied AI System 360.

The categorization 370 is derived from the appended portion of speech 325 is returned by the AI System 360. The categorization comprises one or more types of analyses performed by the AI System including keywords, concepts, relationships, taxonomy, classification, personality attributes, and tone of voice. The categorization elements are assigned probability weights correlating the appended portion of speech 325 more or less closely with the output categorization elements. The higher weighted categorization elements are more likely to be relevant to the appended portion of speech 325 and therefore to the overall discussion and participant 301A, 301B, . . . 301N goals or needs.

The permanent data storage 340 for the Discussion Altering Machine 320 contains participant 301A, 301B, . . . 301N discussion data. The types of data contained in the permanent data storage 340 includes but is not limited to participant profiles for participants who have participated in prior biofeedback discussions using Biofeedback Discussion System 130 and wish to maintain a permanent data profile. These same prior system participants may wish to store their personal documents to be used in current or future discussions, information about prior discussions a participant has had with other participants including the list of participants, the agenda of the discussion, the group goal of the discussion, the list of needs of theirs and other participants in a discussion, questions and answers that occurred during a prior discussion, and copies of prior discussion transcripts to name a few discussion artifacts pertinent to a participant 301A, 301B . . . 301N. Other data items pertaining to system operation include but are not limited metadata about prior discussions, usage data, performance data, and other system-wide statistics or management metrics.

The current data storage 350 contains data structures and content that is used during the instance of each discussion among participants 301A, 301B . . . 301N. Current data storage 350 content can include discussion connection session information, participant digital apparatus including rendering and biosignal and biofeedback (both input and output) devices, participants' 301A, 301B . . . 301N goals, profile, and documents contributed by each participant for this particular discussion, the group goal, discussion agenda, categorizations rendered for individual participants and for the discussion group participants 301A, 301B . . . 301N, participant 301A, 301B . . . 301N questions and the information link answers returned by the AI System 360, the discussion transcript up to the current time, and each portion of speech 330 categorized during the discussion corresponding to that portion of speech 330.

The generated feedback signal 380 is generated by the Discussion Altering Machine 320. The feedback signal 380 is dependent upon the domain of the embodiment, the participants' digital apparatus available to the system, and the content of the categorization to be rendered to the participants 301A, 301B . . . 301N. The feedback signal is the content that participants will be made aware of via the system rendering 390.

The rendered feedback signal 390 is rendered to the participants 301A, 301B . . . 301N by the Discussion Altering Machine. The feedback signal 380 rendering 390 is determined by the Discussion Altering Machine 320 and is dependent on each participants' 301A, 301B . . . 301N available digital apparatus. Rendering 390 can take the form of, but is not limited to one of the following formats: sound, vibration, heat or cold, visual signals including but not limited to lights, pictures, text, smell, or taste. In most instances, the rendered feedback signal will likely be the same as the generated feedback signal 380.

Figure 4:
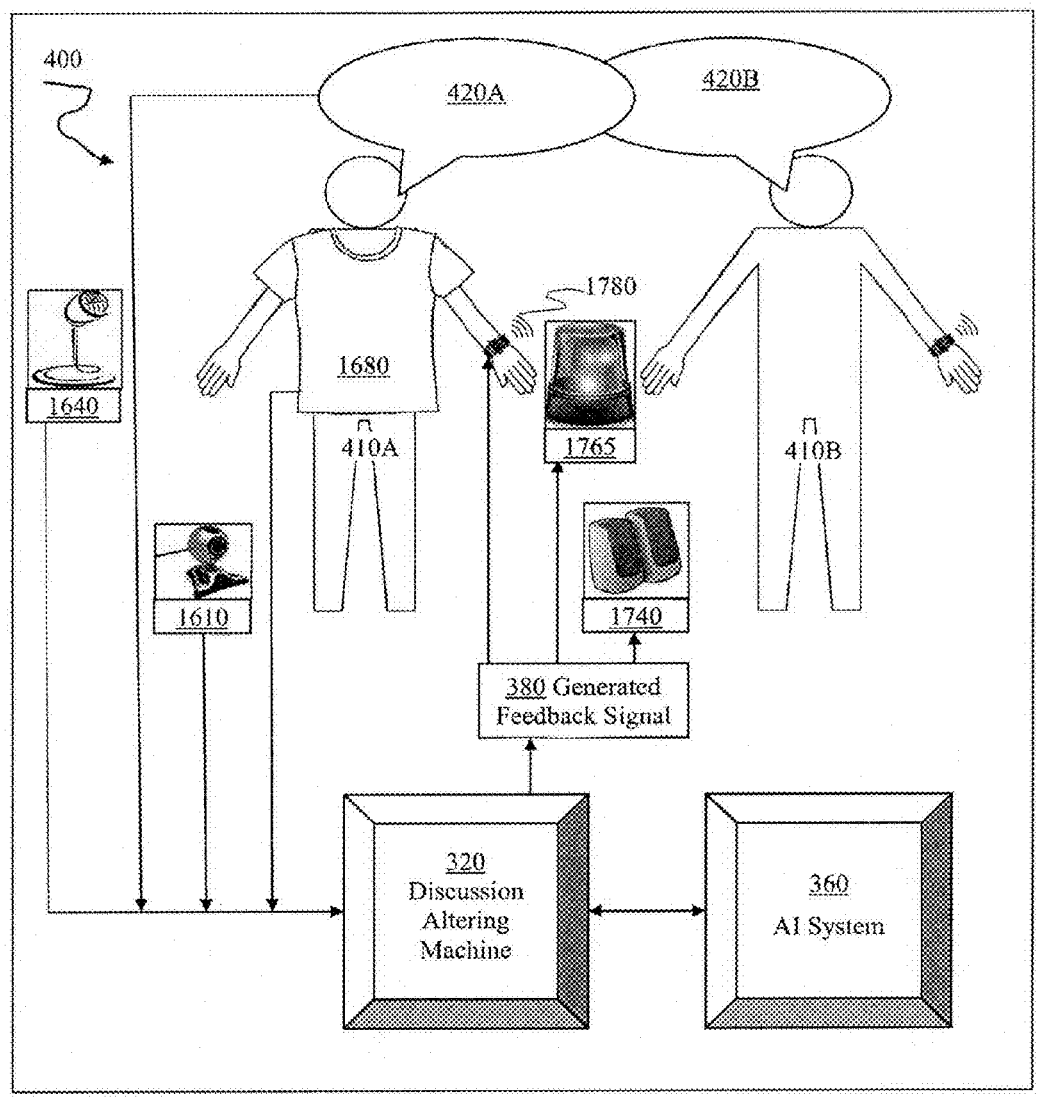
FIG. 4 is a diagram of participants having a discussion, while their biosignals are categorized, and feedback signals are generated and then rendered back to the participants.

FIG. 4 is a diagram of a participants 410A and 410B having a discussion. Devices capture their visually perceptible and sound output biosignals as well as heart and breathing rates e.g., with a camera 1610, a microphone 1640, and a T-shirt containing sensors 1680 respectively. Feedback devices render visual, aural, and tactile feedback signals to participants 410A and 410B. These feedback signals are rendered e.g., to a flashing light 1765, speakers 1740, and a vibrating/shock emitting wristband 1780.

To be useful as biofeedback, biofeedback signals rendered via devices e.g., 1740, 1765, and 1780 are presented to the participants 410A and 410B in substantially near real-time, and preferably in near real-time.

Participants 410A and 410B provide many different types of information to the system. One type is profile information that is dependent on the domain of the embodiment. Another type of information is sensor derived information from a heart and breathing rate T-shirt e.g., 1680, a standard microphone e.g., 1640, and camera e.g., 1610 all to capture their biosignals. Feedback signal are rendered to participant 410A via e.g., a flashing light 1765, speakers 1740, and a vibrating/shock emitting wristband 1780.

Participants 410A and 410B are both human. This example shows two humans in a discussion, but there could be humans 410C, 410D, 410E . . . 410N included in the discussion.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Participant 410A emits biosignals while engaged in the discussion with participant 410B. Biofeedback signals for heart rate, breathing rate, eye movement, and fidgeting and gestures (both general body and hand and limb movement) are categorized. Measurement of heart rate and breathing rate biosignals are obtained whereby the participant 410A wears clothing containing sensors, e.g., a T-shirt 1680. The participants' eye movement, fidgeting, and gesture biosignals are obtained by that participant's eye movement and actions being observed by e.g. a camera 1610.

Participant's 410A portion of speech 420A, as the content, along with participant's 410A biosignals for heart rate, breathing rate, eye movement, fidgeting, and gestures, as expression characteristics, is used by the Discussion Altering Machine e.g., 320. The portion of speech 420A is forwarded on from the Discussion Altering Machine e.g., 320 to the AI System e.g., 360. The AI System e.g., 360 identifies a categorization. The content biosignal categorization is then used by the Discussion Altering Machine e.g., 320 along with the expression characteristic biosignals to generate a Feedback Signal e.g., 380 corresponding to the categorization. The Feedback Signal e.g., 380 is then rendered to participant 410A as aurally from the speakers e.g., 1740, visually from a flashing light e.g., 1765, and tactilely to a vibrating/shock emitting wristband e.g., 1780 during the discussion. The feedback signal from the speakers e.g., 1740, a flashing light e.g., 1765 may alter a subsequent portion of participant's 410A speech.

An example of how the Feedback Signals e.g., 380 are rendered to the participant 410A is as follows: The participants' 410A feedback signals are rendered by the Discussion Altering Machine e.g., 320. If participant's 410A heart rate or breathing rate detected by the T-shirt with sensors e.g., 1680 exceeds normal values the Feedback Signal e.g., 380 will sound a pleasing melody from the speakers e.g., 1740 in order to calm the participant during the discussion. A flashing light e.g., 1765 will illuminate if the participant's 410A eye movement shows a lack of concentration. The wristband e.g., 1780 will vibrate if participant's 410A is seen to be fidgeting by the camera e.g., 1610. The wristband e.g., 1780 will emit a mild shock to participant 410A if their expression characteristic gestures are wild or rude. A loud beep will sound from the speakers e.g., 1740 when participant's 410A portion of speech is characterized as outside of or irrelevant to the goal of the discussion. The participant 410A is likely to respond to these feedback signals as they are rendered and possibly alter their discussion with participant 410B.

Figure 5:
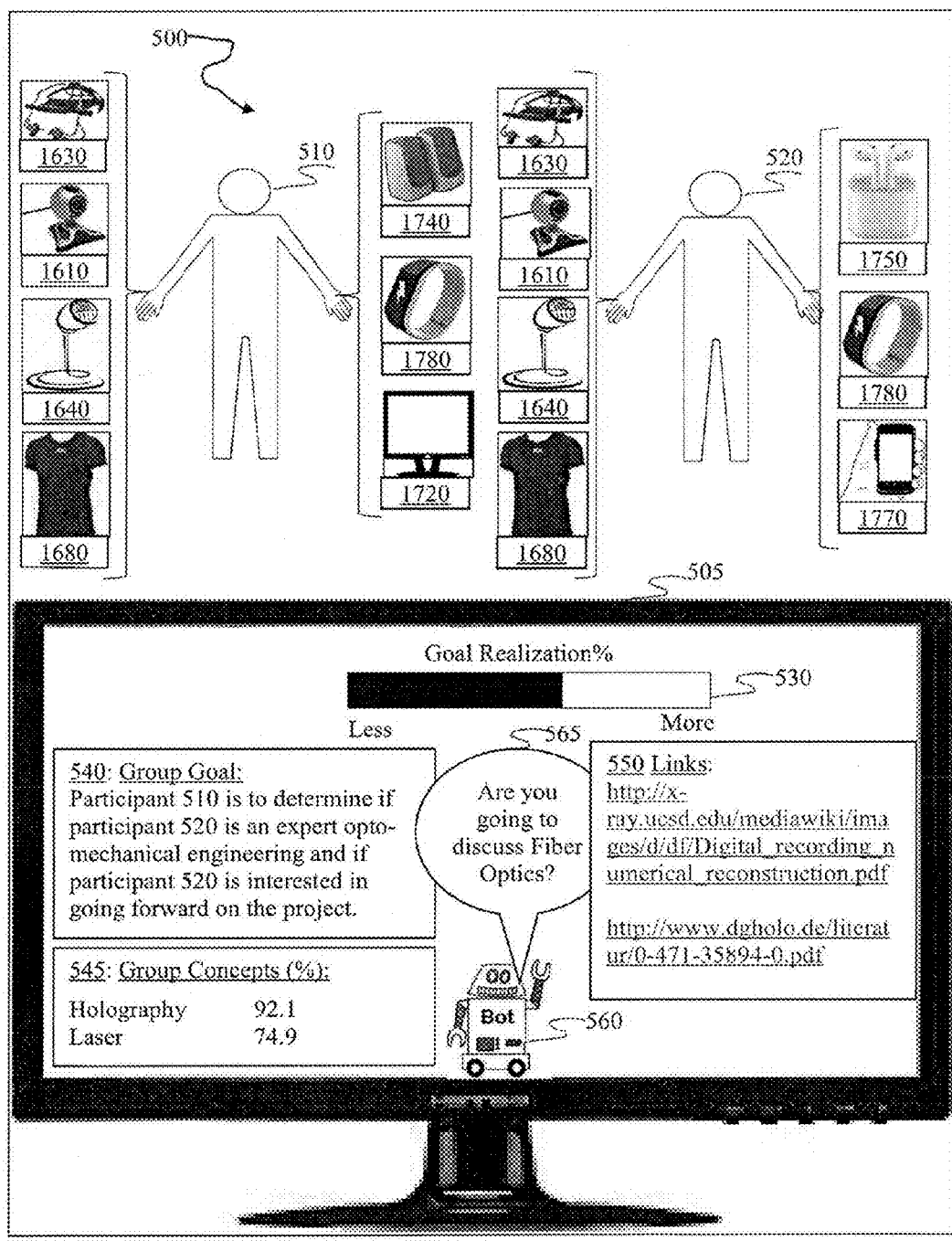
FIG. 5 is a diagram of a two inventor participants engaged in a discussion. Their speech content and expression characteristics are categorized and they receive auditory, visual, and tactile feedback signals in near-real time that may alter their discussion.

FIG. 5 is a diagram of two participants 510 and 520 engaged in a discussion. Devices capture their visually perceptible and sound output biosignals as well as eye behavior and heart and breathing rates e.g., camera 1610, microphone 1640, eye-tracking headset 1630, and T-shirt containing sensors 1680 respectively. Feedback devices render visual, aural, and tactile feedback signals to the inventor participants. These feedback signals are rendered e.g., to a computer display 1720, smartphone 1715, speakers 1740, AirPod™ 1750, and vibrating or shock delivery wristband 1780. The visual display 505 includes a progress indicator for the realization of meeting their group goal 530, the participant's group goal 540, group concepts list 545, their information links 550, an invention system software avatar 560, and the avatar's speech bubble 565.

To be useful as biofeedback, biofeedback signals rendered via devices e.g., 1715, 1720, 1740, and 1750 are presented to one or both of the participants 510, 520 in substantially near real-time, and preferably in near real-time.

Usefulness of biofeedback signals to participants 510, 520 is very likely related to the amount, quality and relevance of information provided to the system. For example, for inventors or knowledge workers, discussions are often centered around their particular domain of study or invention and so it can be important that such persons, when acting as participants, provide copies, or links to, work product that they have produced (authored, created), including documents, papers, patents, drawings, designs, pseudo-code, musical scores, digital art or other creative artifacts that would inform a discussion on a relevant topic with other participants. Some preferred embodiments will request profile information of the participants prior to the discussion (e.g., as part of initialization data 310), which could advantageously include their education and/or career history, their preferred communication language, and possibly other personal attributes that pertain to their knowledge work and invention. Therefore, contribution of relevant artifacts and profile information into the discussion as part of the initialization data prior to the start of the discussion can clarify each participant's initial point of view and stated goal(s). Such initialization data can be used by the Biofeedback Discussion System e.g., 310, along with the discussion content of the portion of speech between the participants, and expression characteristics derived from such speech, to categorize and generate corresponding feedback signals to the participants.

Participant 510 provides many different types of information to the system. One type of information is goals and profile information, and documents. Another type of information is sensor derived information, from cameras, microphones, eye-tracking headsets, body sensors, etc. In this particular example, inventor participant 510 is wearing a heart and breathing rate T-shirt e.g., 1680, an eye-tracking headset e.g., 1630, and is using a standard microphone e.g., 1640, and camera e.g., 1610 to capture their biosignals. Feedback signals are rendered to inventor participant 510 via speakers e.g., 1740, vibrating/shock wristband e.g., 1780, and a display e.g., 1720.

Participant 520 also provides information to the system. One type of information is a relevant patent in addition to their goal and profile information. In this particular example, inventor participant 520 is wearing a heart and breathing rate T-shirt e.g., 1680, an eye-tracking headset e.g., 1630, is using a standard microphone e.g., 1640, and camera e.g., 1610 to capture their biosignals. Feedback signals are rendered to inventor participant 520 via e.g., AirPods™ 1750, a vibrating/shock wristband 1780, and smartphone 1715.

Biofeedback signals rendered to participants can range from the very simple (buzzes, flashes, vibrations, etc.) to more complicated auditory and visual tactile signals, for example music, photographs and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Inventor participant's 510 feedback signals are rendered by the Biofeedback Discussion System e.g., 310. Information available to the discussion about inventor participant 510 includes heart rate and breathing rate from the T-shirt with sensors, voice anger (voice loudness), content anger (anger words), and word complexity from the microphone, eye movement (possibly signifying lying) and pupil dilation (signifying concentration level where 1 is the least concentration and 10 is the highest concentration) from the eye-tracking headset e.g., 1630 and gestures from the camera e.g., 1610. Inventor participant 510 will hear a harsh audio tone from their speakers if they use a loud voice that exceed the loudness threshold, use angry words, or express unfriendly or negative gestures. The speaker e.g., 1740 will emit a foghorn sound to inventor participant 510 if inventor participant 520 shows possible lying that has been detected by their eye-tracking headset. In order to keep the inventor participant concentrating on the discussion, the wristband will provide a mild shock if inventor participant's 510 pupils have constricted below a threshold showing lack of concentration or the camera observes the participants fidgeting or showing other distracting activities showing that their attention is waning. If the words inventor participant 510 uses during the discussion exceed a threshold for word complexity, the wristband will vibrate reminding the participant to be sure to use words that will aid the discussion. Visual feedback signals rendered to inventor participant 510 on a computer display and include the group goal and the discussion progress towards reaching that goal, group concept list, information links, and the system software agent and its speech bubble. Inventor participant 510 may alter their portion of speech and possibly their expression characteristics based on feedback signals that have been generated and rendered to them.

Content anger words include acrid, acrimonious, aggravated, angered, annoyed, antagonistic, antipathetic, apoplectic, ballistic, bellicose, belligerent, bitter, blue in the face, boiling, bristling, burning, caustic, cheesed off, choleric, churlish, cold, contrary, cool, embittered, enraged, exasperated, fired up, fit to be tied, foaming, frustrated, fuming, furious, going crook, hopping, hopping mad, horn-mad, hostile, hot, hot under the collar, icy, incensed, indignant, inflamed, infuriated, irate, ireful, livid, mad, outraged, perturbed, pissed off, rabid, raging, rancorous, rankled, ranting, raving, riled, roiled, seeing red, seething, shirty, smoldering, sore, soreheaded, steamed, steaming, storming, stormy, ticked, vitriolic, worked up, wrathful, wroth, and wrought up.

Word complexity is measured using Flesch-Kincaid core measures (word length and sentence length).

Inventor participant's 520 feedback signals are rendered by the Biofeedback Discussion System e.g., 310. Information available to the discussion about inventor participant 520 includes heart rate and breathing rate from the T-shirt with sensors, voice anger (voice loudness), content anger (anger words), and word complexity from the microphone, eye movement (possibly signifying lying) and pupil dilation (signifying concentration level where 1 is the least concentration and 10 is the highest concentration) from the eye-tracking headset and gestures from the camera. Inventor participant 520 will hear a harsh audio tone from their speakers if they use a loud voice that exceed the loudness threshold, use angry words, or express unfriendly or negative gestures. The speaker will emit a foghorn sound to inventor participant 520 if inventor participant 510 shows possible lying that has been detected by their eye-tracking headset. In order to keep the inventor participant concentrating on the discussion, the wristband will provide a mild shock if inventor participant's 510 pupils have constricted below a threshold showing lack of concentration or the camera observes the participants fidgeting or showing other distracting activities showing that their attention is waning. If the words inventor participant 520 uses during the discussion exceed a threshold for word complexity, the wristband will vibrate reminding the participant to be sure to use words that will aid the discussion. Visual feedback signals rendered to inventor participant 510 on a computer display and include the group goal and the discussion progress towards reaching that goal, group concept list, information links, and the system software agent and its speech bubble. Inventor participant 520 may alter their portion of speech and possibly their expression characteristics based on feedback signals that have been generated and rendered to them.

In FIG. 5, inventor participant 510 and inventor participant 520 happen to be located in different places, but they could use the Biofeedback Discussion System e.g., 310 when sitting next to one another. Inventor participant 510 and inventor participant 520 both enter into the digital realm that will enable the two inventor participants to communicate via the communication link e.g., 120 with each other verbally via video or audio only transmission as well as by using textual exchanges back and forth between each other.

The goal realization progress bar 530 signifies a percentage of the group goal that has been achieved at particular point in time of the inventor participant 510 and inventor participant 520 discussion. The Discussion Altering Machine e.g., 320 keeps track of the group goal at 540, the group concepts at 540, and the top 10 words used in the discussion at 540 and determines a correlation between the group goal, the group concepts, and top 10 words as a percentage of completion in achieving the group goal during the discussion. The measurement derived from this analysis is rendered as a goal realization progress bar 530 signifying whether the discussion is reaching greater or lesser consensus with the group goal 540. The black portion of the goal realization 530 scale signifies the portion of the goal that has been realized with respect to the white part of the scale that is the portion of the goal that has not yet been realized. Although it is a goal of the inventor participants 510 and 520 in the discussion to achieve a goal realization of 100% during the discussion, this will not always be the outcome of the discussion. The rendering of the progress to achieving the group goal, or lack thereof, aids inventor participant 510 and inventor participant 520 to more easily remain focused on achieving the inventor participants' 510 and 520 group goal and remain consistently on-topic to reach their goal during the discussion.

If inventor participants 510 and 520 notice the visually rendered goal realization progress bar 530 showing less progress than was shown in a previous rendering, the inventor participants can decide to either alter and refocus their discussion back within the bounds of the initially stated group goal or decide to change their group goal to incorporate the new, altered direction of their discussion.

Group goals for the discussion are analyzed by the Biofeedback Discussion System e.g., 130 using SMART (for Specific, Measurable, Attainable, Relevant, and Time-Bounded characteristics) as part of the goal setting activity. In the preferred embodiment, the time-bounded aspect of SMART is usually, but not always, the time of the discussion. The group goal format must be comprised of a meaningful complete sentence containing all of the characteristics within the SMART goal framework. The invention system software agent 560 will ask questions of inventor participants and request that inventor participants work together to narrow the differences in their goals iteratively getting closer to group goal convergence between the inventor participants 510 and 520 or combine their goals in such a way that both inventor participants' goals have been absorbed into the group goal, the group goal meets SMART characteristics, and the group goal has been agreed by both inventor participants.

Where there are more than two human inventor participants (more than 510 and 520 as in 510A, 510B . . . 510N, 520A, 520B . . . 520N), at the start of the discussion, the invention system software agent 560 will combine the goals of all inventor participants into a group goal that meets the SMART (for Specific, Measurable, Attainable, Relevant, and Time-Bounded characteristics) and ask each inventor participant to vote on this suggested group goal. If all inventor participants agree on this goal, the goal is rendered at 540 and the discussion begins. If the suggested group goal is not agreed by all inventor participants, each inventor participant will be asked by the invention system software agent 560 to restate their goal in alignment of SMART characteristics and towards goal convergence with the other inventor participant's (510, 510A, 510B . . . 510N, 520, 520A, 520B . . . 520N). The invention system software agent 560 cycling through each inventor participant in turn (will ask each inventor participant one after the other until having asked each inventor participant) presenting a suggested group goal to all inventor participants and then take a vote from each inventor participant on the new group goal until there is agreement on a group goal.

The inventor participants' visually rendered group goal 540 remains the same throughout the inventor participant discussion unless it is determined by inventor participants or is suggested by the Biofeedback Discussion System e.g., 130 that the current group goal no longer is an effective group goal and that the group goal should be reframed. It is rendered as a discussion aid to ensure that participants can always be aware of the goal for their discussion and possibly alter their discussion as needed to keep the discussion moving towards reaching that goal.

A list of group concepts 545 ranked in order from top to bottom vertically is visually rendered to the participant's 510, 520 displays; listed in order from the most relevant to least relevant group concepts so far in the discussion. These concepts are those that the AI system has identified as corresponding to the participant's 510, 520 categorization of their portion of speech. Each concept in the list is associated with a ranking number or rating that signifies its relevance to the discussion that has occurred. This ranking can be a number signifying how many times the categorization has been included in the group concept, can be a percentage of a total relevance over the discussion so far, or can be another measure of significance meaningful in the specific embodiment domain context. Each new rendering of group concepts corresponding to the categorization of a portion of speech e.g., 330 will alter the list of group concepts in one of the following ways: by rearranging the order of most to least important group concepts such that a group concept that has now been determined to have higher relevance to the discussion will be listed before (on top of) another group concept that has been determined to have a lesser relevance to the discussion than the other group concepts, by changing the ranking number or rating value of one or more group concepts that may or may not be reordered within the list but shows an increase or decrease in relevance due to the ranking number or rating value, by not rendering a concept in the list when a group concept that was categorized as relevant earlier in the discussion has subsequently not been part of the discussion for a period of time and is not included in recent categorizations and so its relevance to the overall discussion becomes less and less to the point where the particular group concept no longer is deemed sufficiently relevant by the Biofeedback Discussion System e.g., 320 to be rendered and remain on the group concepts list. In addition to a ranking number or rating that signifies the group concept's relevance to the discussion that has occurred, a rendering of concept relevance can take the form of a rendering as word prominence as in rendering in a larger or smaller font, brighter or duller color, or other differentiating representation. Inventor participants 510, 520 seeing the concepts list entries changing and adding new items during their discussion may likely highlight new topics for discussion to those participants and possibly alter their discussion.

In this example, the Biofeedback Discussion System watches for particular perception words contained in a portion of speech e.g., 330. Perception words include those that are synonyms of "perception" and other related words including but not limited to perceive, think, notice, observe, see, identify, remark, distinguish, take in, pick out, make out, sense, feel, realize, become aware of, understanding, comprehend, acuity, visual sense, acuteness, visual acuity, appreciation, view, apprehension, awareness, trenchancy, cogency, theory, cognizance, supposition, comprehension, sight, concept, sensory experience, cone vision, sense perception, critical discernment, sense impression, daylight vision, sensation, experience, scotopia, eye-mindedness, sagacity, fancy, rod vision, farsight, response, reflection, field of view, recept, flair, range, foresightedness, purview, horizon, power of sight, image, perspicuousness, impression, perspicacity, insight, perspective, intellection, peripheral field, intuition, perceptiveness, keen sight, penetration, knowledge, observation, longsightedness, mental image, noesis, mindfulness, night vision, mental impression, note, memory-trace, notion, longheadedness, opinion, ken, percept, judgment, percipience, intellectual object, peripheral vision, instinct, perspicaciousness, incisiveness, perspicuity, imago, photopia, idea, providence, grasp, quick sight, foresight, realization, field of vision, recognition, feeling, representation, farsightedness, response to stimuli, farseeingness, sagaciousness, eyesight, scope, eye, discernment, day vision, sense of sight, consciousness, sensibility, conception, sentiment, conceit, sightedness, color vision, sweep, cognition, thought, clear sight, twilight vision, astuteness, unobstructed vision, appreciativeness, vision, apperception, visual field, acumen including all grammatical constructions of each word. When a perception word occurs (is in a portion of speech e.g., 330) during a discussion, the Discussion Altering Machine e.g., 320 captures the portion of speech e.g., 330 around the perception word and uses this portion of speech as an input into the AI system e.g., 360. This portion of speech e.g., 330 selected may be the sentence including the perception word, may be the total portion of speech contributed by the inventor participant that spoke the perception word, or may be a portion of speech of a particular length that is useful to the Biofeedback Discussion System e.g., 320 for the particular embodiment.

If the new concepts list 545 presents a divergence away from the group goal, inventor participant 510 or inventor participant 520 may notice that the divergence is actually an interesting combination of concepts, or new idea. Group concepts 545 that are derived from categorizations by the Discussion Altering Machine e.g., 320 may lead inventor participant 510 and inventor participant 520 to associate new information with the new group concepts in the list; possibly deriving new viewpoints, approaches, or concepts. The new inventor participant 510 and 520 ideas may either be in alignment with or divergent from their group goal 540 causing inventor participants 510 and 520 to alter subsequent their discussion or change their group goal.

The interaction of the inventor participants 510 and 520 observing the changing rankings of the rendered group concepts 545 in combination with the other biofeedback signal data, continues throughout the discussion in order to assist the inventor participants to more quickly cover the domain topic under discussion and will help direct the participants towards achieving their group goal.

Links to information 550 that are relevant to the inventor participants 510 and 520 during the discussion are provided by the Discussion Altering Machine e.g., 320 and are triggered by the discussion portions of speech. The Discussion Altering Machine e.g., 320, through the actions of the invention system software agent behavior e.g., 315, detects that an inventor participant, either 510 or 520, may be confused, unknowledgeable, or unclear about a particular topic relevant to the discussion. The invention system software agent 560, acting with invention system software agent behavior, detects the need for information when an inventor participant 510 or 520 uses phrases including but not limited to: "I don't know", "I'm confused", "I disagree", "I don't think so", "I think you should check", or other similar phrases. In this case, the invention system software agent 560 will render a link to information that is rendered as an HTTP(s) URL to the inventor participants 510 and 520. The links may or may not be ranked in a relevance order based on other rankings.

The invention system software agent 560 is rendered as a "BOT" avatar that is visible to the inventor participants 510 and 520 in their displays and demonstrates invention system software agent behavior e.g., 315; managed by the Discussion Altering Machine e.g., 320. The invention system software agent behavior e.g., 315 includes asking inventor participants to vote on a particular topic, assisting in goal setting to align inventor participant 510 and 520 goals into a group goal that satisfies the SMART goal definition of Specific, Measurable, Attainable, Relevant, and Time-Bounded characteristics, responding to specific questions posed by an inventor participant 510 or 520, commenting on or reminding inventor participants 510 and 520 of their progress towards a group goal that has been set as a target for the discussion, and other facilitation or mentoring behaviors.

The invention system software agent speech bubble 565 is used by the invention system software agent 560 to carry on the discussion with the inventor participants 510 and 520. Although it is anticipated that the dispute mediation system software agent 560 will have the capability of aural speech, this embodiment implies both the additional aural speech discussion capability as well as the textual discussion capability via the example of the feedback signal rendered as visual text.

Figure 6:
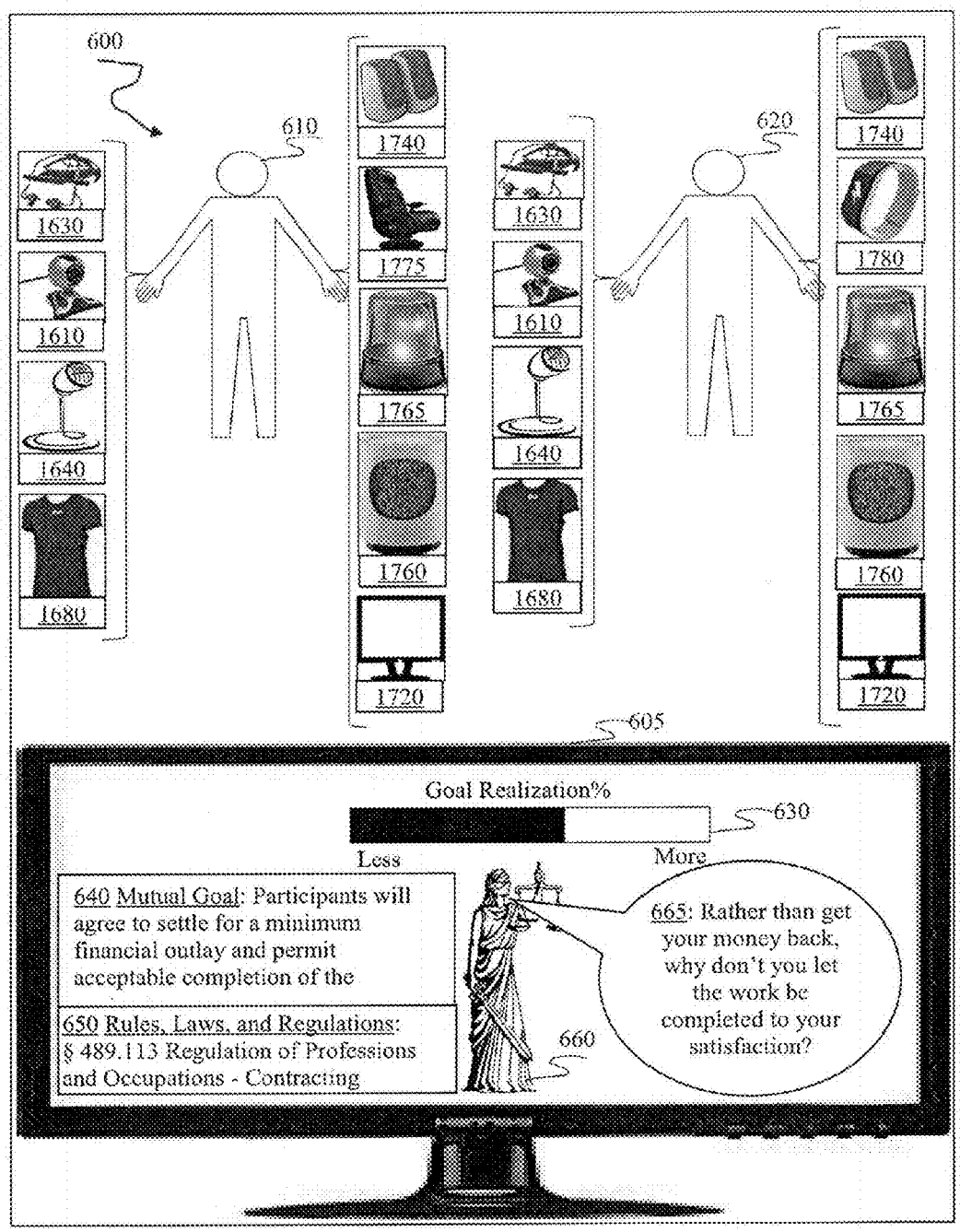
FIG. 6 is a diagram of two dispute mediation participants engaged in a discussion. The diagram depicts an example of using biofeedback to facilitate dispute mediation for the participants reacting to auditory, visual, and tactile feedback signals.

FIG. 6 is a diagram of two participants 610 and 620 engaged in a dispute mediation discussion. Devices capture their visually perceptible and sound output biosignals as well as eye behavior and heart and breathing rates e.g., with a camera 1610, a microphone 1640, an eye-tracking headset 1630, and a T-shirt containing sensors 1680 respectively. Feedback devices render visual, aural, tactile, and olfactory feedback signals to the inventor participants. These feedback signals are rendered e.g., to a computer display 1720, speakers 1740, a vibrating or shock delivery wristband 1780, a vibrating chair 1775, a flashing light 1765, and an aromatherapy dispenser 1760. The visual display 605 includes a progress indicator for the realization of achieving their mutual goal 630, the participant's mutual goal 640, rules, laws, and regulations list 650, a dispute mediation system software avatar 660, and the avatar's speech bubble 665.

To be useful as biofeedback, biofeedback signals rendered via devices e.g., 1720, 1740, 1760, 1765, 1775, and 1780 are presented to one or both of the participants 610, 620 in substantially near real-time, and preferably in near real-time.

Dispute mediation participants 610, 620 have goals in mind that they would like to accomplish during a discussion with one or more other dispute mediation participants and also have stipulations that need to be addressed. Therefore, it is helpful for dispute mediation participants to receive biofeedback from a system that can understand their goals and stipulations and the goals and stipulations of the other dispute mediation participants that will enable them to alter their speech in such a way so that all dispute mediation participants can reach their goals and also resolve the dispute in discussion.

Usefulness of biofeedback signals to participants 610, 620 is very likely related to the amount, quality and relevance of information provided to the system. For example, for dispute mediation participants' discussions are often centered around their particular position in the dispute and their stipulations towards mediation agreement; providing copies, or links to, documents for example depositions, affidavits, contracts, or other relevant artifacts that can inform a mediation discussion with other participants. Some preferred embodiments will request profile information of the participants prior to the discussion (e.g., as part of initialization data 310), which could advantageously provide background on each participant's position in the dispute. Therefore, contribution of relevant artifacts and profile information into the discussion as part of the initialization data prior to the start of the discussion can clarify each participant's initial point of view and stated goal(s). Such initialization data can be used by the Biofeedback Discussion System e.g., 310, along with the discussion content of the portion of speech between the participants, and expression characteristics derived from such speech, to categorize and generate corresponding feedback signals to the participants.

As part of the initialization data input process in this example, each dispute mediation participant states their individual goal for the discussion and lists their primary stipulations with respect to their goal. Also, both dispute mediation participants have submitted affidavits as to their position or opinion on the problem to be discussed during the discussion. Other examples may also request other profile information of the dispute mediation participants for example their role as a dispute mediation participant in the dispute (husband or wife, girlfriend or boyfriend, child, neighbor, business partner, employee, landlord or tenant, or other dispute mediation participant association). Other relevant profile information depends on the type of dispute and may include employment information and history, resident information, criminal or legal dispute history, core issues, values, interests, additional stakeholders, and position, or other germane personal information. Additionally, there may exist legal documents that have been filed or served to one or both dispute mediation participants that each dispute mediation participant would want to have included in the discussion as a basis for an argument or as evidence of the progress to date of the mediation of the dispute.

Each dispute mediation participant needs to disclose if they hold legal degrees, have had legal training (including para-legal), and if and when they have participated in mediation prior to this discussion. Dispute mediation participants are required to provide consent to enter into a dispute mediation discussion and agree that they will be bound by the eventual resolution in a Heads of Agreement. The Biofeedback Discussion System e.g. 130 will not allow a dispute mediation discussion to occur between the dispute mediation participants unless both have provided legal consent. A confidentiality agreement is signed by each of the dispute mediation participants and uploaded to the system.

Dispute mediation is often used to mediate legal contract issues including but not limited to workplace issues, divorce, child custody, commercial agreements, family disputes, and landlord-tenant disputes. It can also be effective in disputes between family members, employees, or neighbors. Non-violent criminal matters, for example claims of verbal or other personal harassment, can also be successfully mediated.

In this dispute mediation example, there are two (2) dispute mediation participants, but there could be more than two for other dispute mediation examples. Examples where there are more than two dispute mediation participants follow a pattern of consensus building similar to the case of when there are more than two inventors in a discussion.

Dispute mediation participant 610 provides many different types of information to the system. One type is profile information (disclosure), where they disclose that they are an attorney and are an interested party in the dispute, a fact-finding and affidavit document, and their stipulations and goals. Another type of information is sensor derived information from a heart and breathing rate T-shirt e.g., 1680, an eye-tracking headset e.g., 1630, a standard microphone e.g., 1640, and camera e.g., 1610 all to capture their biosignals. Feedback signals are rendered to dispute mediation participant 610 via e.g., a display 1720, speakers 1740, a flashing light 1765, a vibrating chair 1775, and an aromatherapy device 1760.

Dispute mediation participant 620 also provides information to the system. One type is profile information (disclosure) and an affidavit document. Another type of information is sensor derived information from a heart and breathing rate T-shirt e.g., 1680, an eye-tracking headset e.g., 1630, and a standard microphone e.g., 1640, and camera e.g., 1610 to capture their biosignals. Feedback signals are rendered to dispute mediation participant 620 via e.g., a display 1720, speakers 1740, a vibrating/shock wristband 1780 that receives vibration or mild shock notifications, and an aromatherapy device 1760.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Dispute mediation participants' 610 and 620 emit biosignals while engaged in their dispute mediation discussion. Biofeedback signals for heart rate, breathing rate, voice anger (loudness), content anger (words), word complexity, eye movement, pupil dilation, and gestures (both general body and hand and limb movement) are categorized. Measurement of heart rate and breathing rate biosignals are obtained whereby each dispute mediation participant 610, 620 wears clothing containing sensors, e.g., a T-shirt 1680. Voice anger (loudness more than 65 dB), content anger (words), and word complexity are obtained via the participant speaking into a microphone, e.g. 1640. Content anger words include acrid, acrimonious, aggravated, angered, annoyed, antagonistic, antipathetic, apoplectic, ballistic, bellicose, belligerent, bitter, blue in the face, boiling, bristling, burning, caustic, cheesed off, choleric, churlish, cold, contrary, cool, embittered, enraged, exasperated, fired up, fit to be tied, foaming, frustrated, fuming, furious, going crook, hopping, hopping mad, horn-mad, hostile, hot, hot under the collar, icy, incensed, indignant, inflamed, infuriated, irate, ireful, livid, mad, outraged, perturbed, pissed off, rabid, raging, rancorous, rankled, ranting, raving, riled, roiled, seeing red, seething, shirty, smoldering, sore, soreheaded, steamed, steaming, storming, stormy, ticked, vitriolic, worked up, wrathful, wroth, and wrought up. Word complexity is measured using Flesch-Kincaid core measures (word length and sentence length). The dispute mediation participants' 610 eye movement and pupil dilation biosignals are obtained by each dispute mediation participant wearing an eye-tracking headset, e.g., 1630. It has been shown that particular eye movement patterns, as in eyes looking up and to the left, can signify lying. Pupil dilation amount exceeding a normal dilation responding only to room lighting likely shows the level of concentration of that participant. The dispute mediation participants' gesture biosignals are obtained by that participant's actions being observed by a camera, e.g. 1610.

Dispute mediation participants' feedback signals are rendered by the Biofeedback Discussion System e.g., 310. The system software agent will respond and notify a dispute mediation participant if the participant's heart rate or breathing rate exceeds normal values and ask them to breathe deeply and take a break from the discussion for a minute or two in order to calm down. At the same time, the aromatherapy device will dispense lemon oil, known to be a calming scent. If a participant's voice exceeds the loudness threshold, uses angry words, or unfriendly gestures, a flashing light will be visible to both participants reminding them to carry out their dispute mediation discussion civilly. A beep from the speakers will sound if either dispute mediation participant uses words that are more complex than is deemed necessary. A foghorn sound from the speakers will be heard by the participants if either has been shown they might be lying from their eye-tracking headsets. Detection of pupil dilation that is less than optimal for concentration or gestures for example fidgeting or moving attention away from the discussion will initiate dispute mediation participant's 610 chair to vibrate and dispute mediation participant's 620 wristband to vibrate whenever their concentration on the discussion wavers. The dispute mediation participants 610, 620 are likely to respond to these feedback signals as they are rendered and possibly alter their discussion.

Although not a requirement, in this example dispute mediation participant 610 is located in the same room as dispute mediation participant 620. They would be able to see each other as well as share some of the biofeedback devices including but not limited to the camera e.g., 1610, the speakers e.g., 1740, computer display e.g., 1720, flashing light e.g., 1765, and aromatherapy device e.g., 1760. FIG. 6 depicts that each dispute mediation participant 610, 620 uses their own set of biofeedback devices, but this is not necessarily required.

The personal goal of each dispute mediation participant 610, 620 must be relevant to the discussion and understood that it will be merged or aligned with the personal goal of the other dispute mediation participant(s). At the start of the discussion, the dispute mediation system software agent 660 asks the dispute mediation participants 610 and 620 about their goals for the discussion. Each dispute mediation participant will answer this question with an opening statement that includes the statement of a goal towards dispute resolution. Both dispute mediation participants' 610 and 620 opening statements are analyzed for similarities and differences by the dispute mediation system software agent 660. From this analysis, the dispute mediation system software agent 660 frames the dispute in a statement to the dispute mediation participants 610 and 620. The dispute mediation system software agent 660 then asks the dispute mediation participants 610 and 620 to reply with a percentage level of agreement on whether the dispute framing is in agreement with their positions. Depending on the responses of the dispute mediation participants, the dispute mediation system software agent 660 will either suggest a mutual goal to be used as a target goal for the discussion or will reframe the statement and ask the participants 610 and 620 reply again with percentage level of agreement with the statement. This process of reframing, generating a statement, replying with percentage agreement, and then formulating a mutual goal continues until both dispute mediation participants 610 and 620 have agreed on a mutual goal.

Feedback signals are rendered visually to the dispute mediation participants 610, 620 by the Biofeedback Discussion System e.g. 130. Participants would see these feedback signals rendered via the computer display e.g., 1720. In this example, a view of the visual display 605 shows example feedback signal renderings that includes a progress indicator for the realization of meeting their group goal 630, the participants' group goal 640, rules, laws, and regulations list 650, a dispute mediation system software avatar 660, and the avatar's speech bubble 665.

A goal realization scale 630 reflects the outcome of both dispute mediation participant's 610 and 620 level of agreement with the dispute framing definition. The consensus scale progress bar graphically shows the amount of agreement between the dispute mediation participants by rendering more black fill in the rectangle as the goal is more realized. The software system agent periodically reminds the dispute mediation participants 610, 620 that this rendered scale signifies their degree of consensus and will continue to reflect the party's escalation or de-escalation of their dispute; providing feedback signals about the convergence toward or divergence from compromise leading to resolution thus altering the dispute mediation participants' 610, 620 discussion.

The dispute mediation participants' mutual goal, 640, derived by combining each participant's personal goals is rendered visually to the dispute mediation participants 610, 620. The mutual goal is made visible to the participant so that they are continually reminded of the goal that they have agreed to work toward during the discussion. Awareness of the mutual goal and reminders by the system software agent of that goal may alter the participants' discussion.

Relevant rules, laws, and regulations 650 are visually by the dispute mediation system software agent so that dispute mediation participants 610, 620 have access to these rules, laws, and regulations during their discussion. The dispute mediation system software agent 660 provides certification to participants 610, 620 that it is a qualified arbiter in front of certain associations for example the FINRA. The dispute mediation system software agent 660 caches relevant laws, regulations, procedural requirements, the Mediation Resolution Agreement, and code of ethics for reference during the discussion between the dispute mediation participants 610, 620.

In this particular example, a dispute mediation system software agent 660, trained as a mediator, is a required dispute mediation participant during the discussion. The Biofeedback Discussion System e.g. 130 renders a visual avatar image (in this example the visually rendered avatar is in the form of "blind justice") that dispute mediation participants 610, 620 that participates in the discussion acting as the dispute mediator. The visual rendering of the system software agent as an avatar is likely to encourage interaction with the participants as it guides them through the mediation, possibly altering their discussion. The system dispute mediation software agent behavior 660 includes asking dispute mediation participants to vote on a particular topic, assisting in mutual goal setting to align dispute mediation participant 610, 620 goals into a group goal that satisfies the SMART goal definition (Specific, Measurable, Attainable, Relevant, and Time-Bounded) characteristics, asking dispute mediation participants 610 and 620 about the stipulations they have entered as part of their initialization data, responding to specific questions posed by a dispute mediation participant 610, 620, and commenting or reminding dispute mediation participants 610, 620 of their progress in towards a goal that has been set as a target for the discussion.

A speech bubble 665 is used by the dispute mediation system software agent 660 to carry on the discussion with the dispute mediation participants 610, 620. Although in other examples the dispute mediation system software agent 660 will have the capability of aural speech, this example implies both the additional aural speech discussion capability as well as the textual discussion capability via the example of the feedback signal rendered as visual text.

At the start of the discussion, the system software agent mediator gives an address to the dispute mediation participants framing the dispute mediation participant's dispute and the rules under which the dialogue and mediation is to take place. The dispute mediation participants have agreed on what forms they are willing to accept in the Heads of Agreement resolution statement at the end of the discussion or series of discussions. The dispute mediation system software agent 660 asks both dispute mediation participants if they agree the terms of the dialogue mediation.

Figure 7:
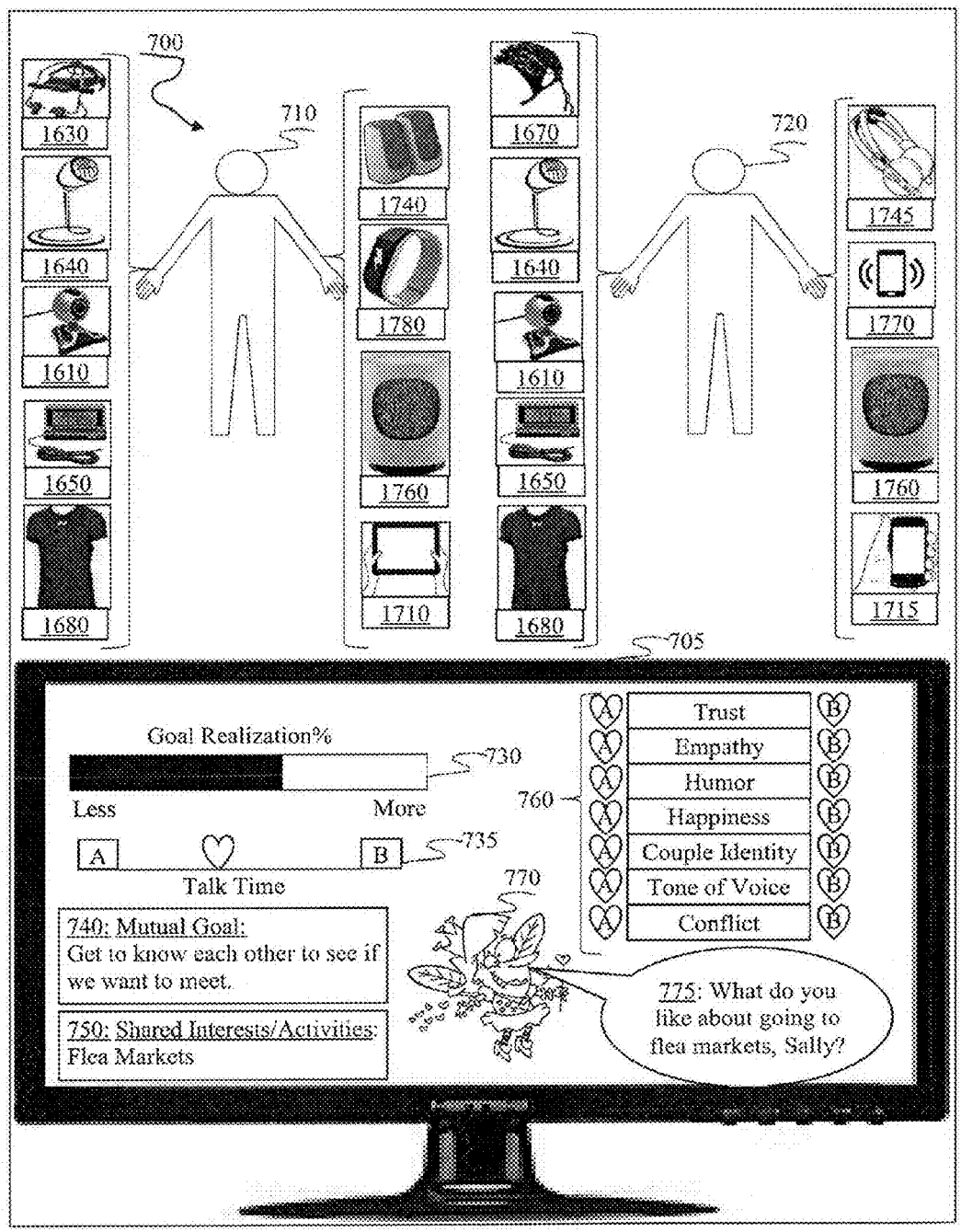
FIG. 7 is a diagram of two dating participants engaged in a discussion. The diagram depicts an example of dating and matchmaking situation where the participants can conduct a discussion about their life goals, their needs, and interests that is informed by auditory, visual, tactile, and olfactory biofeedback signals from the Biofeedback Discussion System.

FIG. 7 is a diagram of two participants 710 and 720 engaged in a dating discussion between two individuals who want to get to know one another. Dating participants can conduct a discussion about their life goals, their needs, and interests that may be altered by the Biofeedback Discussion System e.g., 130. Devices capture their visually perceptible and sound output biosignals as well as eye behavior, brainwave signals, and heart and breathing rates e.g., with a camera 1610, a microphone 1640, an eye-tracking headset 1630, a brainwave helmet 1670, a hand temperature sensor 1650, and a T-shirt containing sensors 1680 respectively. Feedback devices render visual, aural, tactile, and olfactory feedback signals to the inventor participants. These feedback signals are rendered e.g., to a tablet 1710, a smartphone 1715, speakers 1740, headphones 1745, a vibrating or shock delivery wristband 1780, a vibrating smartphone 1770, and an aromatherapy dispenser 1760. The visual display 705 includes a progress indicator for the realization of achieving their mutual goal 730, a participant equal talk-time measure 735, the participants' mutual goal 740, the participants' list of shared interests and activities 750, a relationship compatibility indicator 760, a dispute mediation system software avatar 770, and the avatar's speech bubble 775.

To be useful as biofeedback, biofeedback signals rendered via devices e.g., 1710, 1715, 1740, 1745, 1760, 1770, and 1780 are presented to one or both of the participants 510, 520 in substantially near real-time, and preferably in near real-time.

Dating participants 710, 720 have goals in mind that they would like to accomplish during a discussion with another dating participant. Therefore, it is helpful for dating participants to receive biofeedback from a system that can understand their goals and the goals of the other dating participant that will enable them alter their speech in such a way so that each of the dating participants can reach their goals during the discussion.

Usefulness of biofeedback signals to participants 710, 720 is very likely related to the amount, quality and relevance of information provided to the system. For example, for dating participants' discussions are often centered on their backgrounds, interests, and experiences.

As part of the initialization process in this example, each dating participant provides their personality profiles, life priorities, interests and activities as well as their goals for the discussion that can inform their dating discussion with another dating participant. In some examples, the biofeedback discussion system e.g., 130 in FIG. 1 will request profile information of the participants prior to the discussion (e.g., as part of initialization data 310) which could advantageously provide background on each dating participant's expectations. Awareness of personality attributes including but not limited to timeliness, punctuality, cleanliness, orderliness, physical and emotional needs, financial goals, spending habits, career goals, family priorities, religious or spiritual aspects, and the lifestyle tempo of each dating participant will be helpful to the other participant to know prior to the discussion. In this example, it is assumed that each dating participant 710, 720 has reviewed the other participants profiles prior to the discussion.

Therefore, the contribution of relevant personality and profile information into the discussion as part of the initialization data prior to the start of the discussion can illuminate each dating participant's view of the world and their stated goal(s). Such initialization data can be used by the Biofeedback Discussion System e.g., 310, along with the discussion content of the portion of speech between the participants, and expression characteristics derived from such speech, to categorize and generate corresponding feedback signals to the participants.

When considering dating, physical proximity can be very important, Yet in this example, the actual location of each dating participant 710, 720 is assumed to be acceptable to the other participant prior to entering into the discussion. In this example, dating participants 710 and 720 are situated in different locations.

Dating participant 710 provides many different types of information to the system. One type is profile information (disclosure), including personality characteristic scores, a life priority, their location, their interests and activities, and their personal goal for the discussion. Other profile attributes that may be important in some examples are attributes like language, age, education achieved. Another type of information is sensor derived information from a heart and breathing rate T-shirt e.g., 1680, an eye-tracking headset e.g., 1630, a hand temperature sensor e.g., 1650, a standard microphone e.g., 1640, and camera e.g., 1610 all to capture their biosignals. Feedback signals are rendered to dispute mediation participant 710 via e.g., a tablet 1710, speakers 1740, a vibrating/shock emitting wristband 1780, and an aromatherapy device 1760.

Biofeedback signals rendered to participants can range from the very simple (buzzes, flashes, vibrations, etc.) to more complicated auditory and visual tactile signals, for example photographs and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Dating participants' 710 and 720 emit biosignals while engaged in their dispute mediation discussion. Biofeedback signals for heart rate, breathing rate, hand temperature, word complexity, eye movement, and pupil dilation are categorized.

Measurement of dating participant's 710 heart rate and breathing rate biosignals are obtained by each dating participant wearing clothing containing sensors, e.g., a T-shirt 1680. The dating participant's hand temperature biosignal is obtained by the dating participant affixing a temperature sensor to their finger(s), e.g., 1650. The level of dating participant's 710 word complexity is measured using the Flesch-Kincaid core measures (word length and sentence length). The dating participant's eye movement and pupil dilation biosignals are obtained by the dating participant wearing an eye-tracking headset, e.g., 1630.

Dating participant 720 also provides information to the system. One type is profile information (disclosure) including personality characteristic scores, a life priority, their location, their interests and activities, and their personal goal for the discussion. Another type of information is sensor derived information from a heart and breathing rate T shirt e.g., 1680, an brainwave helmet e.g., 1670, a hand temperature sensor e.g., 1650, a standard microphone e.g., 1640, and camera e.g., 1610 all to capture their biosignals. Feedback signals are rendered to dispute mediation participant 710 via e.g., a smartphone 1715, headphones 1745, a vibrating smartphone 1770, and an aromatherapy device 1760.

Measurement of dating participant's 720 heart rate and breathing rate biosignals are obtained by each dating participant wearing clothing containing sensors, e.g., a T-shirt 1680. The dating participant's hand temperature biosignal is obtained by the dating participant affixing a temperature sensor to their finger(s), e.g., 1650. The level of dating participant's 710 word complexity is measured using the Flesch-Kincaid core measures (word length and sentence length). The dating participant's brainwaves for concentration biosignals are obtained by the dating participant wearing a brainwave headset, e.g., 1670.

Dating participants' feedback signals are rendered by the Biofeedback Discussion System e.g., 310. The system software agent will respond and notify a dating participant if the participant's heart rate or breathing rate exceeds normal values and ask them to breathe deeply and take a break from the discussion for a minute or two in order to calm down. At the same time, the aromatherapy device will dispense lemon oil, known to be a calming scent, or another pleasing scent chosen by the dating participant. A harsh sound would be emitted by the headset dating participant 720 is listening to if it was determined from their eye movements that dating participant 710 was lying. Dating participant's 710 wristband and dating participant's 720 vibrating smartphone will vibrate if that participant's word usage complexity exceeds a threshold. A pleasant tone is sounded from participant's 710 speakers and from participant's 720 headphone when participant's 710 eye-tracking headset and participant's 720 brainwave helmet shows that they are concentrating on the discussion. A gong will sound for each participant whose concentration is shown to be waning. The dating participants 710, 720 are likely to respond to these feedback signals as they are rendered and possibly alter their discussion.

The personal goal of each dating participant 710, 720 must be relevant to the discussion and understood that it will be merged or aligned with the personal goal of the other dating participant. At the start of the discussion, the dating system software agent 770 asks the dating participants 710 and 720 about their goals for the discussion. Each dating participant will answer this question. Both dating participants' 710 and 720 answers are analyzed for similarities and differences by the dating system software agent 770. From this analysis, the dating system software agent 770 frames the mutual goal to the dating participants 710, 720. The dating system software agent 770 then asks the dating participants 710, 720 to reply with a percentage level of agreement on whether the mutual goal is sufficiently in agreement with their goal. Depending on the responses of the dating participants, the dating system software agent 770 will either suggest a mutual goal to be used as a target goal for the discussion or will reframe the statement and ask the participants 710, 720 to reply again with percentage level of agreement with the new mutual goal. This process of reframing, generating a mutual goal, replying with percentage agreement, and then agreeing a mutual goal continues until both dating participants 710, 720 have agreed on a mutual goal.

Feedback signals are rendered visually to the dispute mediation participants 710, 720 by the Biofeedback Discussion System e.g. 130. Participants would see these feedback signals rendered via their tablet e.g., 1720 or smartphone e.g., 1715. In this example, a view of the visual display 705 shows example feedback signal renderings that includes a progress indicator for the realization of meeting their group goal 730, a participant equal talk-time measure 735, the participants' group goal 740, the participants' shared interests and activities 750, a relationship compatibility indicator 760, a dating system software avatar 770, and the avatar's speech bubble 775.

A sliding-scale goal realization measure 730 shows how successful the dating participants 710 and 720 have been in realizing their mutual goal. In this dating example, as opposed to other examples, goals can be quite vague. It is preferred that the dating example mutual goal does not follow the structure of setting SMART (for Specific, Measurable, Attainable, Relevant, and Time-Bounded characteristics) goals. Measurement of goal realization in this embodiment is based on measurement factors as in the process of setting a mutual goal in the beginning, how many shared interests and experiences the dating participants 710 and 720 share during the discussion, and how the dating participants react to the feedback signals 730 throughout the discussion.

A sliding-scale measure of the percentage of talk-time that each dating participant 710 and 720 has had during the discussion is rendered visually to the participants. The slider measurement indicator is rendered here as a heart-shape that will slide across the horizontal line from left to right and back as the percentage of talk-time for each of the dating participants 710, 720 out of the total time that has so far elapsed during the discussion changes. As an example, participant 710 has contributed portions of speech for 20 minutes of the total of 30 minutes that have so far elapsed for the discussion with participant 710. That would mean that participant 720 has contributed portions of speech for 10 minutes during that discussion with participant 710. Therefore the generated feedback signal for percentage of talk-time would be visually rendered showing the heart-shaped indicator at the two-thirds (⅔) point from the left-hand side of the scale. Dating participants 710 and 720 will be able to track if either of them is dominating the discussion and possibly change their discussion to allow more turn-taking or ask questions of the less voluble participant so that they have more of a chance to talk; thus the talk-time scale rendering may alter the discussion.

The mutual goal 740 is agreed by both dating participants 710 and 720. When the discussion begins, the dating system software agent 770 will acknowledge each dating participants' 710, 720 individual goals. The dating system software agent will explain that discussions are more successful if both dating participants 710, 720 agree to one mutual goal. The dating system software agent will ask each of the dating participants 710, 720 to suggest a goal that could be considered mutual. If the dating participants 710, 720 are able to agree on one stated goal for the discussion then this goal is rendered at 740. If the dating participants are not able to agree, then the dating system software agent will suggest some generalized mutual goals that are considered by the participants and finally agreed by the dating participants 710 and 720 and that feedback signal is visually rendered at 740.

A list of shared interests and activities 750 is a simple matching of both participant's 710 and 720 profiles that were part of their initialization data e.g., 310 for interests and activities. Although the profile lists for each dating participant 710, 720 contain the matched item, by visually rendering the matched item as being shared between the dating participants, it encourages a feeling of consensus thus possibly altering the subsequent discussion. Dating participants 710 and 720 may likely be interested and engaged more deeply in the discussion knowing that the other participant shares an interest or activity of theirs. During the discussion, other shared interests or activities may be discussed and the system will add these items to the shared interests and activities list, further reinforcing a commonality between the dating participants and possibly altering their subsequent discussion.

A relationship compatibility indicator 760 is a visual rendering of dating participant 710, 720 feedback signals generated from the personal attributes dating participants demonstrate during the discussion. As dating participants' 710, 720 portions of speech are categorized, their expression characteristics observed, and their biosignals are detected, feedback signals signifying the level of trust and empathy they feel for the other dating participant, how humorous they feel the other dating participant is, the amount of happiness they feel when they are in a discussion with the other dating participant, the amount of couple identity that they feel is being established, their tone of voice during the discussion, and their feeling of conflict or lack thereof are rendered visually for the dating participants 710, 720. The heart-shaped icons situated to the left of each personal attribute and labeled with an "A" are feedback signal outputs for dating participant 710 and to the right of each personal attribute and labeled with a "B" are feedback signal outputs for dating participant 720. The heart-shaped icons will change color based on the feedback signal values generated. Colors ranging from low feedback signal values to high feedback signal values are rendered to dating participants 710 and 720 as violet, blue, green, yellow, orange, and red.

A relationship compatibility indicator 760 visually renders feedback signals for trust, empathy, humor, happiness, couple identity, tone of voice, and conflict amount. Trust for each dating participant 710 and 720 is measured by eye movement and pupil dilation biosignals categorized with respect to values for personal reputation and self-disclosure. Empathy for each dating participant 710 and 720 is measured by the Biofeedback Discussion System e.g. 130 analyzing the discussion content for word use, the length of interaction on topics (level of involvement) where sharing or supportive exchange occurs, and the amount and of questions (degree of initiative) posed by one dating participant to the other dating participant. Humor is measured for each dating participant 710, 720 by the Biofeedback Discussion System e.g. 130 analyzing the discussion content for humor content including but not limited to instances of parody, irony, satire, wit, surprise turn, and word play. The reaction of the other dating participant to these forms of humor through laughter or smiling (as a positive response) or through silence, a negative expression, or looking away (as a negative response) enhances or mitigates the dating participant's humor feedback signal discussion content measurement. It is envisioned in other dating examples that dating participants will use biosignal devices as in a non-invasive optical brain and tissue monitoring system that can detect the activation of regions in the brain for verbal humor now shown to occur in the amygdalar and midbrain regions as well as the anterior cingulate cortex and frontoinsular cortex. Happiness is measured for each dating participant 710, 720 by the Biofeedback Discussion System e.g. 130 by categorizing the discussion content for positive word use especially when coupled with humor. Facial expression characteristics, for example, smiles are categorized by using a camera e.g., 1610. Couple Identity is measured for each dating participant 710, 720 by the Biofeedback Discussion System e.g. 130 categorizing the discussion content for we-ness statements; specifically statements demonstrating mutuality, interaction similarity, and inclusion of other in self. Tone of Voice is measured for each dating participant 710, 720 by the Biofeedback Discussion System e.g. 130 categorizing voice loudness and tone biosignal from the dating participant's speech using a microphone e.g., 1640. Conflict is measured for each dating participant 710, 720 by the Biofeedback Discussion System e.g. 130 categorizing the pattern of speech between dating participants 710, 720 where the increased use of overlapping speech connoting competition as well as the number and frequency of interruptions showing increased conflict and changes in speaker (turn-taking) showing reduced conflict.

The dating system software agent 770 is visually rendered to the dating participants 710, 720 as a matchmaker avatar. The dating system Software Agent Behavior e.g., 315 is driven by the Discussion Altering Machine e.g., 320. Focusing back on FIG. 7, the dating system software agent participates in a discussion with the dating participants 710 and 720 providing feedback signals in the form of prompts about personality test readings for each dating participant, aligning dating participant goals into a mutual goal 740, asking one or the other dating participants 710, 720 about their interests or activities that might be shared 750 or just interesting to each other, asking one or the other dating participants about their personality characteristic scores or other profile items, commenting on aural or tactile feedback signal renderings for each dating participant 710, 720, commenting on the participants' level of shared experience, providing advice on ways to achieve the dating participants' mutual goal 730, helping the participants 710 and 720 keep track of the time during their discussion, and answer questions that have been posed directly to the dating system software agent.

A speech bubble 775 is used by the dating system software agent 770 to carry on the discussion with the dating participants 710 and 720. Although it is anticipated that the dating system software agent 770 will have the capability of aural speech, this example implies both the additional aural speech discussion capability as well as the textual discussion capability via the example of the feedback signal rendered as visual text.

Figure 8:
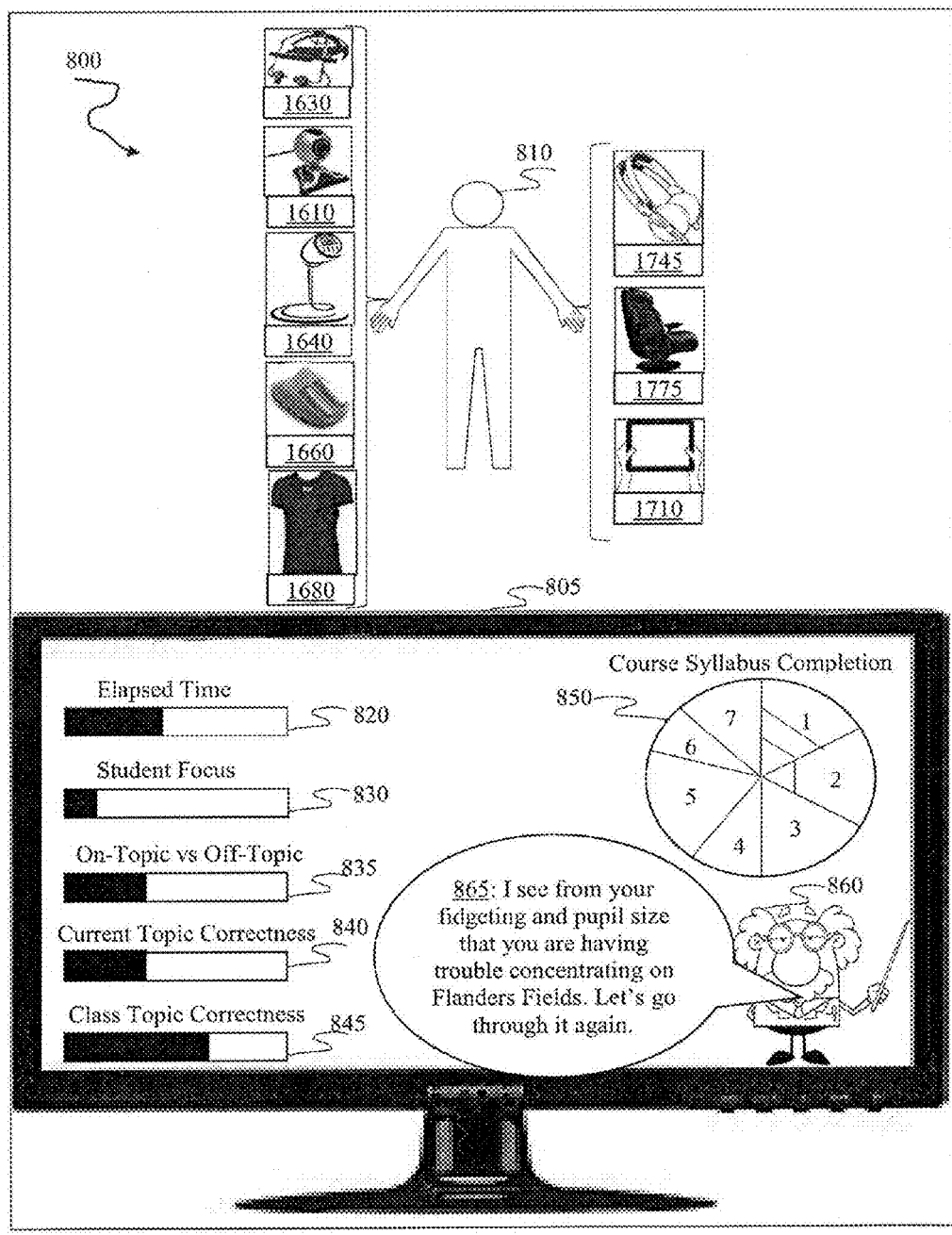
FIG. 8 is a diagram of a student participants taking coursework. The diagram depicts an example where the participant can conduct an informed coursework discussion with the Biofeedback Discussion System's embodiment of a professor avatar.

FIG. 8 is a diagram of a student participant 810 who is enrolled in a Massively Open Online Course (MOOC) or other educational course using an educational support system. Devices capture his/her visually perceptible and sound output biosignals as well as eye behavior, hand temperature, and heart and breathing rates e.g., with a camera 1610, a microphone 1640, an eye-tracking headset 1630, a hand temperature sensor 1650, and a T-shirt containing sensors 1680 respectively. Feedback devices render visual, aural, and tactile feedback signals to the student participants. These feedback signals are rendered e.g., to a tablet 1710, headphones 1745, and a vibrating chair 1775. The visual display 805 includes a progress indicator for the elapsed time of the discussion 820, the student focus metric 830, the percentage of the discussion that has been either on-topic or off-topic 835, the percentage of correct answers versus incorrect answers given by the student participant 810 within the current topic 840, the percentage of correct answers versus incorrect answers given by other students using the system and registered for the same MOOC class 845, the course completion graph 850, the an education system software agent avatar 860, and the avatar's speech bubble 865.

To be useful as biofeedback, biofeedback signals rendered via devices e.g., 1710, 1745, and 1775 are presented to the participant 810 in substantially near real-time, and preferably in near real-time.

In the domain of education and the sub-domain of students in a MOOC or other educational course, students have goals in mind that they would like to accomplish during a discussion with the Biofeedback Discussion System e.g., 130 and possibly with other student participants who are enrolled in the same course. All student participants as described herein are human. A student participant 810 may have difficulty with the course subject matter or may be challenged by the process of absorbing coursework information in a manner that enables them to be successful in achieving satisfactory or even exemplary scores on tests and graded written coursework. Often in a typical educational course or more often in a MOOC, a student participant does not receive sufficient personalized tutorial support due to staffing and cost challenges. Therefore, it is helpful for a student participant 810 to receive biofeedback signals from a system that can understand their educational goals. The system's categorization of their portion of speech and expression characteristics from the discussion, generating feedback signals that are then rendered back to the student participant 810 should provide helpful guidance and cues to alter their speech in alignment with coursework topics in order to help them reach their desired educational goal.

The goal for student participant 810 is implied in that the student participant is enrolled in a particular course and by using the biofeedback discussion system for tutorial implies that the student participant's goal is to learn the coursework material to achieve some level of competence through discussions with the education system software agent 860.

Usefulness of biofeedback signals to participant 810 is very likely related to the amount, quality and relevance of information provided to the system. For example, for coursework education participants, discussions are mostly centered on their course syllabus, textbooks, ancillary study materials, and prior discussion session data. Some preferred embodiments will automatically load the participant's data (e.g., as part of initialization data 310) from prior learning sessions and populate the rendered feedback signals accordingly; incorporating this data for the start of the current discussion.

In this coursework education example, there is one student participant 810. This example demonstrates a one-on-one tutorial assisted by an education system software agent 860. It is envisioned that there would be other student participants 810B, 810C, 810D . . . 810N who would be enrolled in the same course as student participant 810; each student participant engaged in their own one-on-one learning session. In the case where more than one student participant in a course is using the biofeedback discussion system e.g., 130 at the same time, these students can communicate with each other by text (chat) and voice to possibly aid their learning experience.

Student participant 810 provides many different types of information to the system. One type is coursework particular, for example, includes syllabus, textbook content, and ancillary course materials. Another type of information is sensor derived information from a heart and breathing rate T-shirt e.g., 1680, an eye-tracking headset e.g., 1630, a Galvanic Skin Response (GSR) monitor e.g., 1660, a standard microphone e.g., 1640, and camera e.g., 1610 all to capture their biosignals. Feedback signal are rendered to student participant 810 via e.g., a tablet 1710, headphones 1745, and a vibrating chair 1775.

Student participant 810, who is enrolled in the MOOC or other educational course, wants to improve their coursework learning and retention. The motivation for using the Biofeedback Discussion System can be for the satisfaction of learning the coursework subject matter to the best of their ability in the time afforded during the course duration or they might be more focused on achieving sufficient learning proficiency in the coursework subject in order to test and write well enough to achieve a targeted grade for the course from the instructor (a pass).

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Student participant 810 emits biosignals while engaged in their educational tutorial discussion. Biofeedback signals for heart rate, breathing rate, hand temperature, pupil dilation, and fidgeting and gestures (both general body and hand and limb movement) are categorized. Measurement of heart rate and breathing rate biosignals are obtained whereby the student participant 810 wears clothing containing sensors, e.g., a T-shirt 1680. The student participant's 810 hand temperature and hand moisture are obtained whereby the student participant 810 rests his/her fingers in the slots at the top of the GSR device, e.g., 1660. The student participant's 810 pupil dilation biosignal is obtained by the student participant wearing an eye-tracking headset, e.g., 1630. It has been shown a participant's concentration level can be discerned by the amount of pupil dilation observed for that participant. The student participants' fidgeting and gesture biosignals are obtained by that participant's actions being observed by a camera, e.g. 1610.

Student participants' 810 feedback signals are rendered by the Biofeedback Discussion System e.g., 310. The education system software agent 860 will respond and notify a student participant if the participant's heart rate or breathing rate exceeds normal values or the GSR devices shows that they are stressed and ask them to breathe deeply and take a break from the discussion for a minute or two in order to calm down. A loud beep will sound if the student participant's pupil dilation goes below a threshold showing lack of concentration or if the camera shows fidgeting or hand or arm movement that shows that the student participant is distracted and their attention is waning. A pleasant tone is sounded periodically for as student participant 810 if the participant has answered questions correctly during that time interval. A short pleasant melody will be played when a student participant's correct answers exceed those of his/her classmates in the same course and using the biofeedback discussion system. If the student participant 810 goes off-topic, the participant's chair vibrates. The student participant 810 is likely to respond to these feedback signals as they are rendered and possibly alter their discussion.

Feedback signals are rendered visually to the dispute mediation participant 810 by the Biofeedback Discussion System e.g. 130. The student participants 810 would see these feedback signals rendered via the tablet e.g., 1710. In this example, a view of the visual display 805 shows example feedback signal renderings that include, but is not limited to a discussion time elapsed indicator 820, a student focus measurement indicator 830, an on-topic vs off-topic indicator 835, a current topic correctness measure 840, an overall class correctness indicator 845, an education system software avatar 860, and the avatar's speech bubble 865.

A sliding-scale measure 820 shows the time that has elapsed during the discussion. Prior to starting the discussion a student participant 810 states how much time they want to devote to their current discussion with the Biofeedback Discussion System e.g. 130; this time allotment signifies 100%. The black portion of the elapsed time box, signifies the portion of the total time set aside for the discussion that has already elapsed. The portion of time is measured as a percentage of the whole time allocated for the discussion. The time elapsed rendering is provided as a tool to help the student participant 810 manage the time that they have allocated in order to best achieve their current discussion goal. When the elapsed time measurement approaches 90% completion, the Biofeedback Discussion System will notify or remind the student participant (by way of the education system software agent speech bubble 865) that the discussion time is nearing completion. In the event the student participant 810 exceeds the planned time that was selected by the student participant prior to starting the discussion, the Biofeedback Discussion System will continue the discussion with the student participant and remind them at regular intervals (possibly 5 minutes or 10 minutes for different examples) that the student participant's 810 allocated time has been exceeded by the total aggregate of time that has elapsed since the discussion was planned to have ended. The elapsed time measurement graph would in this case show as totally black until the discussion is closed.

A measurement bar 830 indicates the level of focus or concentration of the student participant 810 during the discussion. The feedback signal that is generated and rendered at 830 is derived from the categorization of the student participant's portion of speech compared with the pupil dilation biofeedback signal from the student participant. An example can be when a student participant 810 is asked a question by the education system software agent 860 and the student participant answers the question. If the student participant's 810 answer to the question is determined by the Biofeedback Discussion System e.g. 130 as correct and the pupil dilation biofeedback signal shows a dilated pupil, the rendering of the focus measurement bar will show a higher proportion of black as a percentage of total concentration. The education system software agent 860 will complement the student participant on their ability to focus and indicate to the student that their behavior during the discussion was appropriate so that they understand that they have applied the correct amount of focus on the question; through positive biofeedback. If the student participant's 810 answer to the question is correct and the pupil dilation is low, then the pupil dilation biofeedback signal shows a constricted or less dilated pupil, the student participant 810 will hear a loud beep and the rendering of the focus measurement bar will show a lower proportion of black as a percentage of total concentration. The education system software agent 860 will next ask a more difficult question of the student participant 810 as the student participant was likely not challenged sufficiently by the prior question. If the student participant's 810 answer to the question is incorrect and the pupil dilation is low, the student participant 810 will hear a loud beep and the rendering of the focus measurement bar will show a lower proportion of black as a percentage of total concentration. The education system software agent 860 will suggest to the student to focus on the questions. If the student participant's 810 answer to the question is incorrect and the biofeedback signal shows a dilated pupil, the rendering of the focus measurement bar will show a higher proportion of black as a percentage of total concentration. The education system software agent 860 will ask a less difficult question next as the student participant 810 shows that they were focused, but their understanding of the question and the information they were trying to learn was not yet sufficient for the difficult question that had just been incorrectly answered.

A measurement bar 835 indicates the aggregate of the student participant's speech in the discussion that pertaining to the topic selected for discussion. The feedback signal that is rendered as a measurement is a percentage of the proportion of on-topic discussion compared to the off-topic portion of the discussion. The Biofeedback Discussion System e.g., 130, matches the vocabulary contained in the student participant's 810 portion of speech against a taxonomic and ontological view of the coursework topic content. Divergence from the vocabulary considered to be "part of" the topic content is tabulated as off-topic. This vibrating chair (e.g., 1775) feedback signal informs the student participant 810 as to how familiar they are with their selected topic (knowing where the topic boundaries are), how efficient they are during their discussion study time, and how clear or unclear they are about a particular topic.

A measurement bar 840 signifies the number of questions posed by the education system software agent 860 to the student participant 810 that have been answered correctly compared to those questions that have been answered incorrectly as a percentage. The student participant selects the coursework topic list and the rendering 840 is a measurement of correct vs incorrect answers that have been completed during the current discussion within the currently selected topic. This feedback signal informs the student participant about their progress in learning about and retaining information about a particular topic as a part of their coursework. A pleasant tone is sounded periodically if student participant 810 has answered questions correctly during some time interval, possibly giving encouragement to the student participant that will increase his/her focus; altering a subsequent portion of speech.

A measurement bar 845 indicates the performance of other student participants 810B, 810C, 810D . . . 810N in other discussions in achieving correct answers for the student participant's 810 currently selected topic. The other student participants' data included in the rendered feedback signal are student participants who have participated in discussions using the Biofeedback Discussion System e.g., 130 and are students in the same MOOC or other educational course as student participant 810. The measurement of correct vs incorrect answers for students from other discussions are rendered only for the specific topic within the coursework that student participant 810 has selected. This feedback signal informs student participant 810 about their scholastic performance in comparison with other students in their particular course. This information is especially helpful to those student participants who are using the Biofeedback Discussion System to ensure that they achieve a passing grade for the course or may want to achieve the top grade in the course when competing against the other student participants.

A graphical representation 850 of the student participant's coursework (either a MOOC or other educational course) curricula that the student has been supplied at the outset of the course. The Biofeedback Discussion System in this example would be aligned with educational institutions and educational instruction providers such that the course curricula for each course for which a student participant 810 would access the Biofeedback Discussion System is available to that system prior to the student participant entering into the discussion. The Biofeedback Discussion System would also have access to coursework reading material and any other educational information tools that are made available to the student participant 810 as part of the particular course for which that student will use the Biofeedback Discussion System. This example shows a course that consists of seven (7) main topics or areas of study that comprise the syllabus for the course. The graph 850 it shows that student participant 810 has used the Biofeedback Discussion System to discuss topics 1 and 2. The graph also shows that more discussion has occurred about topic 1 than topic 2. A filled in segment of the circle that comprises a topic signifies that the student participant has completed their learning and study of that topic. Completion signified by this graphic does not prevent the student participant from continuing discussions on that topic with the Biofeedback Discussion System.

The education system software agent 860 embodying the system Software Agent Behavior e.g., 315 for education is driven by the Discussion Altering Machine e.g., 320. Focusing back on FIG. 8, the system has rendered a visual representation of the education system software agent as a professor avatar. The education system software agent 860 participates in a discussion with the student participant 810 to provide feedback signals in the form of informational links pertinent to the discussion topic, reacts to student participant feedback signals 830, 835, 840, 845, and 850, and determines the presentation order and difficulty of questions asked of student participant 810 that have been derived from the MOOC or other educational course syllabus and collated by the Biofeedback Discussion System e.g., 130. The student participant 810 engaged in a one-on one discussion with the education system software agent 860 may identify the professor avatar as a kind and helpful persona that is encouraging and always finds the appropriate level of difficulty to use when in a discussion with that student participant.

A speech bubble 865 is used by the education system software agent 860 to carry on the discussion with student participant 810. Although it is anticipated that the education system software agent 860 will have the capability of aural speech, this embodiment implies both the additional aural speech discussion capability as well as the textual discussion capability via the example of the feedback signal rendered as visual text.

Figure 9:
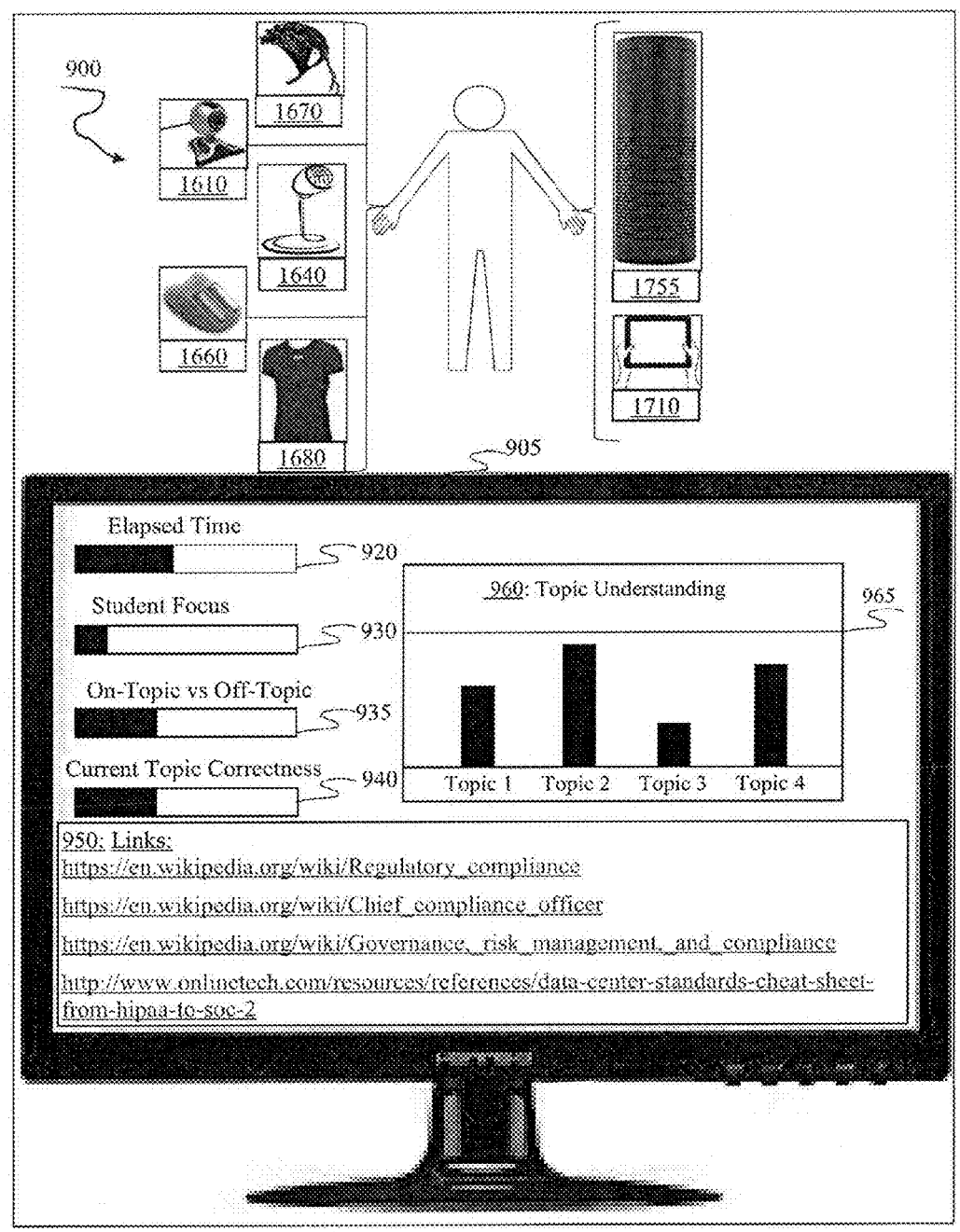
FIG. 9 is a diagram of a student participant practicing a skill during a discussion. The diagram depicts an example where the participant practices the skill, or wants behavioral practice education. The Biofeedback Discussion System provides aural and visual feedback signals that guide the participant's learning of the skill.

FIG. 9 is a diagram of a student participant 910 who wants to learn detailed knowledge within a specific domain area or sub-domain area of knowledge in order to be considered skilled in that domain or sub-domain area. Devices capture his/her visually perceptible and sound output biosignals as well as eye behavior, hand temperature, and heart and breathing rates e.g., with a camera 1610, a microphone 1640, an eye-tracking headset 1630, a hand temperature sensor 1650, and a T-shirt containing sensors 1680 respectively. Feedback devices render visual and aural signals to the student participants. These feedback signals are rendered e.g., to a tablet 1710 and the Echo speaker/AI system e.g., 1755. The visual display 805 includes a progress indicator for the elapsed time of the discussion 820, the student focus metric 830, the percentage of the discussion that has been either on-topic or off-topic 835, the percentage of correct answers versus incorrect answers given by the student participant 810 within the current topic 840, the percentage of correct answers versus incorrect answers given by other students using the system and registered for the same MOOC class 845, the course completion graph 850, the an education system software agent avatar 860, and the avatar's speech bubble 865.

To be useful as biofeedback, biofeedback signals rendered via devices e.g., 1710 and 1755 are presented to the participant 910 in substantially near real-time, and preferably in near real time.

When seeking educational support to learn and master domain or sub-domain knowledge, students have goals in mind that they would like to accomplish during a discussion with the Biofeedback Discussion System e.g., 130. All student participants as described herein are human. A student participant 910 may have recently been selected for a new job position, been promoted at their current job position, wants to seek a new job position, or has some other reason for wanting to understand a specific domain or sub-domain of knowledge which they have not yet mastered. Therefore, it is helpful for a student participant to receive biofeedback signals from a system that can understand their educational goals and work with the student participant one-on-one to help them achieve their desired educational goal. The goal for the student participant is to sufficiently learn enough for their purposes and possibly to achieve mastery such that they would be considered as subject matter experts within their chosen domain.

The student participant 910 wants to master knowledge in a specific domain or sub-domain. The motivation for using the Biofeedback Discussion System can be that they want to be able to discuss pertinent topics within a domain or sub-domain as needed, as when unknown topic areas arise at work. Another motivation can be that the student participant's 910 peers employed in a particular industry all understand a domain or sub-domain and that the student participant knows that in order to be competitive with their peers they will need to also gain this knowledge. Other motivating situations are when a student participant 910 has identified a particular job position or a job role for which they want to be qualified and so want to fill in the holes in their domain knowledge on pertinent topics.

Usefulness of biofeedback signals to participant 910 is very likely related to the amount, quality and relevance of information provided to the system. For example, for domain knowledge mastery, discussions are mostly centered on their topical books, articles, papers, whitepapers, industry news, informational videos, prior discussion session data, and any other relevant artifacts to the domain. Some preferred embodiments will automatically load the participant's data (e.g., as part of initialization data 310) from prior learning sessions and populate the rendered feedback signals accordingly; incorporating this data for the start of the current discussion.

In this domain knowledge mastery example, there is only one student participant 910 who is human. Student participant 910 engages in a one-on-one discussion with the Biofeedback Discussion System e.g., 130. The Biofeedback Discussion System is embodied by the Echo speaker/AI system, e.g., 1755.

Student participant 910 provides many different types of information to the system. One type is domain knowledge specific for example books, papers, textbook articles, whitepapers, industry news articles, informational videos, and other relevant content. Another type of information is sensor derived information from a heart and breathing rate T-shirt e.g., 1680, a brainwave helmet e.g., 1670, a standard microphone e.g., 1640, and camera e.g., 1610 all to capture their biosignals. Feedback signal are rendered to student participant 910 via e.g., a tablet 1710, and the Echo speaker/AI system 1755.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Student participant 910 emits biosignals while engaged in their domain knowledge mastery discussion. Biofeedback signals for heart rate, breathing rate, hand temperature, mental concentration, and fidgeting and gestures (both general body and hand and limb movement) are categorized. Measurement of heart rate and breathing rate biosignals are obtained whereby the student participant 910 wears clothing containing sensors, e.g., a T-shirt 1680. The student participant's 910 hand temperature and hand moisture are obtained whereby the student participant 910 rests his/her fingers in the slots at the top of the GSR device, e.g., 1660. The student participant's 910 mental concentration biosignal is obtained by the student participant wearing a brainwave helmet, e.g., 1670. It has been shown a participant's concentration level can be discerned by the brainwave activity in the prefrontal cortex observed for that participant. The student participants' fidgeting and gesture biosignals are obtained by that participant's actions being observed by a camera, e.g. 1610.

Student participants' 910 feedback signals are rendered by the Biofeedback Discussion System e.g., 310. The Echo speaker/AI system e.g., 1755 will respond and notify a student participant if the participant's heart rate or breathing rate exceeds normal values or the GSR devices shows that they are stressed and ask them to breathe deeply and take a break from the discussion for a minute or two in order to calm down. A foghorn will sound if the student participant's 910 brainwaves showing lack of concentration or if the camera shows fidgeting or hand or arm movement that signifies that the student participant is distracted and their attention is waning. A pleasant tone is sounded periodically for as student participant 910 if the participant has answered questions correctly during that time interval. A short pleasant melody will be played when a student participant's correct answers exceed have exceeded a system determined threshold over a period of time. The motivated student participant 910 is likely to respond to these feedback signals as they are rendered and possibly alter their discussion.

Feedback signals are rendered visually to the dispute mediation participant 910 by the Biofeedback Discussion System e.g. 130. The student participants 910 would see these feedback signals rendered via the tablet e.g., 1710. In this example, a view of the visual display 905 shows example feedback signal renderings that include, but is not limited to a discussion time elapsed indicator 920, a student focus measurement indicator 930, an on-topic vs off-topic indicator 935, a current topic correctness measure 940, an informational links list 950, a topic understanding graph 960 with a domain understanding target line 965.

A sliding-scale measure 920 of the time that has elapsed during the discussion. Prior to starting the discussion a student participant 910 states how much time they want to devote to their current discussion with the Biofeedback Discussion System e.g. 130; this time allotment signifies 100%. The black portion of the elapsed time box, signifies the portion of the total time set aside for the discussion that has already elapsed. The portion of time is measured as a percentage of the whole time allocated for the discussion. The time elapsed rendering is provided as a tool to help the student participant 910 manage the time that they have allocated in order to best achieve their current discussion goal. When the elapsed time measurement approaches 90% completion, the Biofeedback Discussion System will notify or remind the student participant (by way of the Echo speaker/AI system e.g., 1755) that the discussion time is nearing completion. In the event the student participant 910 exceeds the planned time that was selected by the student participant prior to starting the discussion, the Biofeedback Discussion System will continue the discussion with the student participant and remind the student participant at regular intervals (possibly 5 minutes or 10 minutes for different embodiments) that the student participant's allocated time has been exceeded by the total aggregate of time that has elapsed since the discussion was planned to have ended. The elapsed time measurement graph would in this case show as totally black until the discussion is closed.

A measurement bar 930 indicates the level of focus or concentration of the student participant 910 during the discussion. The feedback signal that is generated and rendered at 930 is derived from the categorization of the student participant's 910 portion of speech compared with the brainwave biofeedback signal from the student participant. An example can be when a student participant is asked a question by the Echo speaker/AI system e.g., 1755 and the student participant 910 answers the question. If the student participant's answer to the question is determined by the Biofeedback Discussion System e.g. 130 as correct and the brainwave biofeedback signal indicates concentrated focus, the rendering of the focus measurement bar will show a higher proportion of black as a percentage of total concentration. The Echo speaker/AI system e.g., 1755 will complement the student participant on their ability to focus and to indicate to the student that their behavior during the discussion was appropriate and to understand that they have applied the correct amount of focus on the question; providing positive biofeedback. If the student participant's 910 answer to the question is correct and the brainwave activity shows low concentration, the rendering of the focus measurement bar will show a lower proportion of black as a percentage of total concentration and the Echo speaker/AI system e.g., 1755 will emit a foghorn sound. The Echo speaker/AI system e.g., 1755 will next ask a more difficult question of the student participant 910 as the student participant was likely not challenged sufficiently by the prior question. If the student participant's 910 answer to the question is incorrect and the brainwave activity shows low concentration, the rendering of the focus measurement bar will show a lower proportion of black as a percentage of total concentration and the Echo speaker/AI System e.g., 1755 will emit a foghorn sound. The Echo speaker/AI system e.g., 1755 will suggest to the student to focus on the questions. If the student participant's 910 answer to the question is incorrect and the biofeedback signal shows brainwave focused concentration, the rendering of the focus measurement bar will show a higher proportion of black as a percentage of total concentration. The Echo speaker/AI system e.g., 1755 will ask a less difficult question next as the student shows that they were focused, but their understanding of the question and the information they were trying to learn was not yet sufficient for the difficult question that had just been incorrectly answered.

A measurement bar 935 indicates the aggregate of the student participant's 910 speech in the discussion pertaining to the topic selected for discussion. The feedback signal that is rendered is a measurement as a percentage of the proportion of on-topic discussion compared to the off-topic portion of the discussion. The Biofeedback Discussion System e.g., 130, matches the vocabulary contained in the student participant's 910 portion of speech against a taxonomic and ontological view of the coursework topic content. Divergence from the vocabulary considered to be "part of" the topic content is tabulated as off-topic and the Echo speaker/AI system e.g., 1755 will sound a buzzer. This feedback signal informs the student participant 910 as to how familiar they are with their selected topic (knowing where the topic boundaries are), how efficient they are during their discussion study time, and how clear or unclear they are about a particular topic.

A measurement bar 940 signifies the number of questions posed by the Echo speaker/AI system e.g., 1755 to the student participant 910 that have been answered correctly compared to those questions that have been answered incorrectly as a percentage. The student participant 910 selects the topic from a topic list and the rendering is a measurement of correct vs incorrect answers that have been completed during the current discussion within the currently selected topic. This feedback signal informs the student participant 910 about their progress in learning about and retaining information about a particular topic as a part of their coursework. A pleasant tone is sounded periodically if student participant 910 has answered questions correctly during some time interval, possibly giving encouragement to the student participant that will increase his/her focus; altering a subsequent portion of speech.

Information links 950 are provided by the Biofeedback Discussion System e.g., 130. The links rendered in this list pertain to the specific topic that has been currently selected by the student participant 910 for the discussion. In addition, when the system has determined that a student participant 910 either has not yet fully understood and retained a topic from the current list of links or when a specific question asked by the student participant is not covered in the list of links, the system will render other or more details links to information to assist the student participant 910 in gaining understanding and topic competence. The student participant 910 may want to ask the Echo speaker/AI system e.g., 1755 to clarify information contained in one or more links and can ask questions accordingly.

A graph of the all topics from a topic list is generated by the Biofeedback Discussion System e.g., 130. The graphical rendering of feedback signals based on categorizations of a portion of speech from the student participant 910 signify the gained understanding (learning) or lack of understanding of each of the topics in a topic list. The graph bar length is determined based on the number of questions asked by the Echo speaker/AI system e.g., 1755 and answered correctly by the student participant 910 within a topic when compared against all questions asked within that topic. The graph bar length is also affected by the difficulty of the questions being asked by the Echo speaker/AI system e.g., 1755 of the student participant 910. Question difficulty within a topic is an attribute assigned by the Biofeedback Discussion System as part of that topic's ontological description. The question difficulty attribute is a multiplier applied to the value of # questions answered correctly/# questions asked (the number of questions answered correctly divided by the total number of questions asked).

An achievement threshold line 965 signifies the target to reach to achieve mastery of the identified topics. This graphical feedback signal identifies to the student participant 910 the extent of the skills gap they currently have for a particular topic. The value of this line with respect to the reflection of questions answered correctly and with respect to question difficulty within the topic is determined by the Biofeedback Discussion System e.g., 130 as a measure of possibly somewhere between 75-85% in most cases as an appropriate threshold of knowledge mastery that would be found acceptable in most job position and operational knowledge situations. It is envisioned that this embodiment will take into consideration the competition that is found to exist with the selected knowledge domain and adjust the acceptable threshold for knowledge mastery upwards if there is considered to be greater competition or downwards if the competition is less.

In this example, the education system Software Agent Behavior e.g., 315 and driven by the Discussion Altering Machine e.g., 320 is embodied in the Echo speaker/AI system e.g., 1755. Focusing back on FIG. 9, the Echo speaker/AI system e.g., 1755 participates in a discussion with the student participant 910 to provide feedback signals in the form of informational links 950 pertinent to the discussion topic, reacts to student participant 910 feedback signals 920, 930, 935, 940, and 960 and determines the presentation order and difficulty of questions asked of the student participant 910 that have been derived from the topic list and collated by the Biofeedback Discussion System e.g., 130. The Software Agent Behavior e.g., 315 embodied in the Echo speaker/AI system e.g., 1755 will remind the student participant 910 of the time, will make comments on the student participant's 910 progress within a topic, and may suggest reviewing a particular topic more thoroughly based on the student participant's 910 correct answer performance to date. In this example it is assumed all communication with the Echo speaker/AI system e.g., 1755 is verbal although other interface options are envisioned for other examples.

Figure 10:
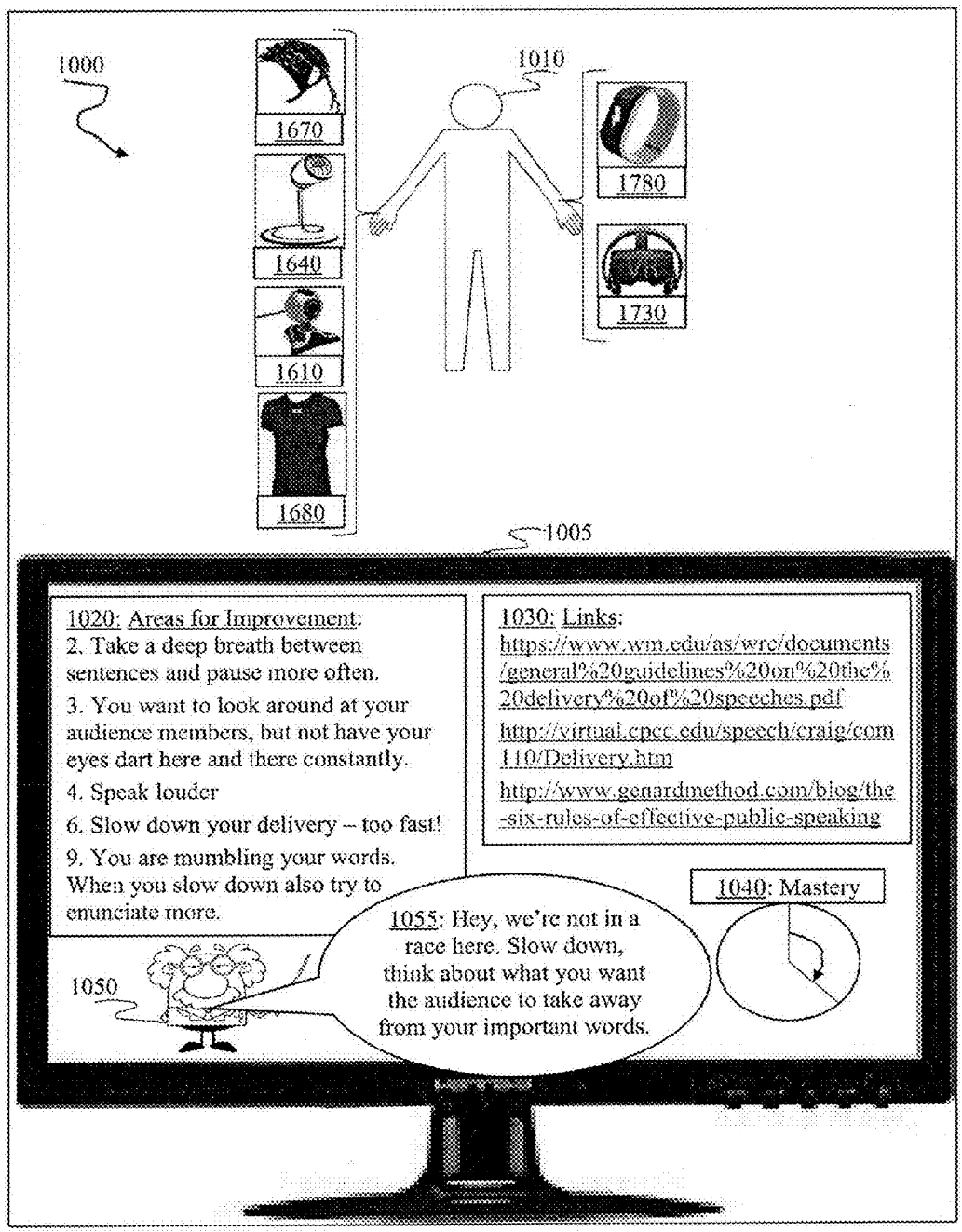
FIG. 10 is a diagram of a student participant wanting to master topic knowledge within a domain. The diagram depicts an example where the participant receives aural, visual, and tactile feedback signals to quickly gain the specific topical knowledge desired.

FIG. 10 is a diagram of an educational support system for a student participant 1010 who wants to master a skill or practice. Devices capture his/her visually perceptible and sound output biosignals as well as brain behavior and heart and breathing rates e.g., with a camera 1610, a microphone 1640, a brainwave helmet 1670, and a T-shirt containing sensors 1680 respectively. Feedback devices render visual, aural, and tactile feedback signals to the student participants. These feedback signals are rendered e.g., to a Virtual Reality (VR)/Augmented Reality (AR) headset 1730, and a vibrating/shock emitting wristband 1780. The visual display 1005 includes a list of areas for improvement 1060, a progress indicator for the elapsed time of the discussion 1120, informational links 1030, a graph of skill mastery progress 1140, an education system software agent avatar 1150, and the avatar's speech bubble 1155.

To be useful as biofeedback, biofeedback signals rendered via devices e.g., 1730 and 1780 are presented to the participant 1010 in substantially near real-time, and preferably in near real-time.

When a student participant 1010 has identified a particular skill or practice in which they want to become proficient they want to find an instructor who will understand what their specific goal is and who will be able to help them focus in on the steps required to achieve their goal without incurring extraneous instruction time. The motivation for using the Biofeedback Discussion System e.g., 130 can be that they want to learn how to be more socially adept in conversation as they are new to a group of people that they work with or engage with socially, they want to practice for an interview for a job or other important personal screening situation, or they want to practice speaking as in preparing for a speech to be delivered to a group of people. In this example, the student participant 1010 wants to perfect the delivery of a speech they will give to a large audience.

The goal for student participant 1010 is very straightforward. They want to achieve a maximum performance rating for content meaning, word usage, vocal tone, speed of speech delivery, and speech clarity by a particular calendar date.

Usefulness of biofeedback signals to participant 1010 is very likely related to the amount, quality and relevance of information provided to the system. For example, student participant 1010 would want the Biofeedback Discussion System to be aware of the background materials that they used to compose the content of their speech. They would also want to convey areas in which they feel they have weaknesses in speech delivery including but not limited to nervousness, talking too loudly or softly and other aspects of speech delivery clarity. Some preferred embodiments will automatically load the participant's data (e.g., as part of initialization data 310) from prior practice sessions and populate the rendered feedback signals accordingly; incorporating this data for the start of the current discussion.

In this mastery of a skill or practice example, there is only one student participant 1010 who is human. Student participant 1010 engages in a one-on-one discussion with the Biofeedback Discussion System e.g., 130. The Biofeedback Discussion System is embodied by the education system software agent avatar 1050.

Student participant 1010 provides many different types of information to the system. One type is skill or practice artifacts including but not limited to prior speeches (text), speeches given by others to be used as good examples (audio or video), and other relevant content. Another type of information is sensor derived information from a heart and breathing rate T-shirt e.g., 1680, a brainwave helmet e.g.,

1670, a standard microphone e.g., 1640, and camera e.g., 1610 all to capture their biosignals. Feedback signal are rendered to student participant 910 via e.g., a VR/AR headset 1730, and a vibrating or shock emitting wristband 1780.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Student participant 1010 emits biosignals while engaged in their speech practice discussion. Biofeedback signals for heart rate, breathing rate, eye movement, voice loudness, voice tone, speed of speech, word complexity, speech content, and speech clarity are categorized. Measurement of heart rate and breathing rate biosignals are obtained whereby the student participant 1010 wears clothing containing sensors, e.g., a T-shirt 1680. The student participant's 1010 eye movement biosignal is obtained by the camera e.g., 1610. The student participant's 1010 voice loudness, voice tone, speed of speech, word complexity, speech content, and speech clarity biosignals are obtained by the student participant speaking into a microphone, e.g., 1640.

Student participants' 1010 feedback signals are rendered by the Biofeedback Discussion System e.g., 310. The education system software agent 1050 will respond and notify a student participant if the participant's heart rate or breathing rate exceeds normal values and ask them to breathe deeply and take a break from the discussion for a minute or two in order to calm down. A loud beep will sound if the student participant's brainwaves show a lack of concentration or if the camera observes wandering eyes, fidgeting, or hand or arm movement that shows that the student participant 1010 is distracted and their attention is waning. A pleasant short melody sounds for the student participant 1010 at the end of each practice session (of the speech) if the most recent practice is an improvement over the previous practice (assessing voice loudness, voice tone, speed of speech, word complexity, speech delivery, and speech clarity). If there has been no improvement or there is a degrading in the speech delivery, then the foghorn sound comes through the VR/AR headset e.g., 1730 speakers. Whenever the student participant's 1010 speech speeds up too much for clear understanding or the speech participant's voice is too soft, the vibrating/shock wristband will vibrate reminding the student participant to enunciate and speak up. If the vibration reminder has been executed a set number of times, determined by the Biofeedback Discussion System assessment of the student participant's abilities, the vibrating/shock wristband will emit a mild shock to impress the student participant that they are not paying attention to their speech delivery. The student participant 810 is likely to respond to these feedback signals as they are rendered and possibly alter their discussion.

Feedback signals are rendered visually to the student participant 1010 by the Biofeedback Discussion System e.g. 130. Student participant 1010 would see these feedback signals rendered via the VR/AR headset e.g., 1730. In this example, a view of the visual display 1005 shows example feedback signal renderings that include a list of areas for improvement 1060, a progress indicator for the elapsed time of the discussion 1120, informational links 1030, a graph of skill mastery progress 1140, an education system software agent avatar 1150, and the avatar's speech bubble 1155.

In this example the VR/AR headset, e.g., 1730 provides aural and visual feedback signals to the student participant 1010 using the VR capabilities of the headset. It is envisioned that in other examples that feedback signal functionality would be two-way as in obtaining biosignals from the student participant 1010 as well as providing generated feedback signals to that student participant 1010 from the VR/AR headset e.g., 1730. VR headset biosignals may include eye movement detection as well as head, arm, and body movement detection. Feedback signals may expand visual and aural signals to include 3D sound and a 360° visual field with realistic depth perception.

Additional information or an Areas for Improvement list 1020 is provided to the student participant 1010 and is updated after each speech delivery by the student participant 1010. This example shows that student participant 1010 is breathing too fast and the Biofeedback Discussion System e.g., 310 through the system software avatar 1050 suggests that the student participant 1010 takes a deep breath at the end of a sentence, and possibly pause their speech more often. The system notices that the student participant's 1010 eyes are darting around constantly possibly conveying lying or lack of concentration to a future audience. The system suggests an approach to looking from place to place consciously (look at the audience members), but not move their eyes quickly without focus. The student participant 1010 has been speaking too softly, too quickly, and is not enunciating their words. The system points out these aspects of the student participant's 1010 speech delivery in a clear and concise textual manner that the education system software agent 1050 will mention from time to time during the next speech practice to provide multiple feedback signal sources that the student participant 1010 can use to alter the delivery of their speech.

Information links 1030 are provided by the Biofeedback Discussion System e.g., 130. The links rendered in this list pertain to the skill or practice area that has been currently selected by the student participant 1010 for the discussion. In addition, when the system has determined that a student participant 1010 either has not yet fully understood and retained a topic from the current list of links or when the student participants asks a specific question that has not been covered in the existing links list, the system will render other or more detailed and relevant links to information to assist the student participant 1010 in gaining understanding of the skill or practice with a goal to achieving competence.

A clock-shaped graph 1040 is rendered showing the level of mastery of the skill or practice achieved so far by the student participant 1010 over a series of discussions. Skill or practice mastery is heavily dependent on the goal that the student participant 1010 has set forth when in discussions with the Biofeedback Discussion System e.g. 130. Within the context of improving social conversation, aspects of the total time spent in discussion with the Biofeedback Discussion System as well as showing an improvement in keeping a discussion's biosignals within the target range set and rendered to the student participant are part of the mastery evaluation metric. Within the context of practicing for a job interview, answering questions correctly while maintaining within-target values for their biosignals constitutes mastery. Within the context of preparing to deliver a speech the speech content evaluation and the speech delivery biosignals being maintained within-target during speech delivery would constitute mastery.

The education system software agent 1050 embodying the system Software Agent Behavior e.g., 315 is driven by the Discussion Altering Machine e.g., 320. Focusing back on FIG. 10, the system has rendered a visual representation of the education system software agent 1050 as a professor avatar. The education system software agent participates in a discussion with the student participant 1010 to provide feedback signals in the form of a list of areas of improvement 1020, informational links 1030 pertinent to the discussion skill or practice, and a graph representing the student participant's level of skill mastery. The education system software agent 1050 reacts to student participant feedback signals 1020 and 1030 and provides supporting information about the student participant's 1010 biosignal output values.

A speech bubble 1055 is used by the education system software agent 1050 to carry on the discussion with the student participant 1010. Although it is anticipated that the education system software agent 1050 will have the capability of aural speech, this embodiment implies both the additional aural speech discussion capability as well as the textual discussion capability via the example of the feedback signal rendered as visual text.

Figure 11:
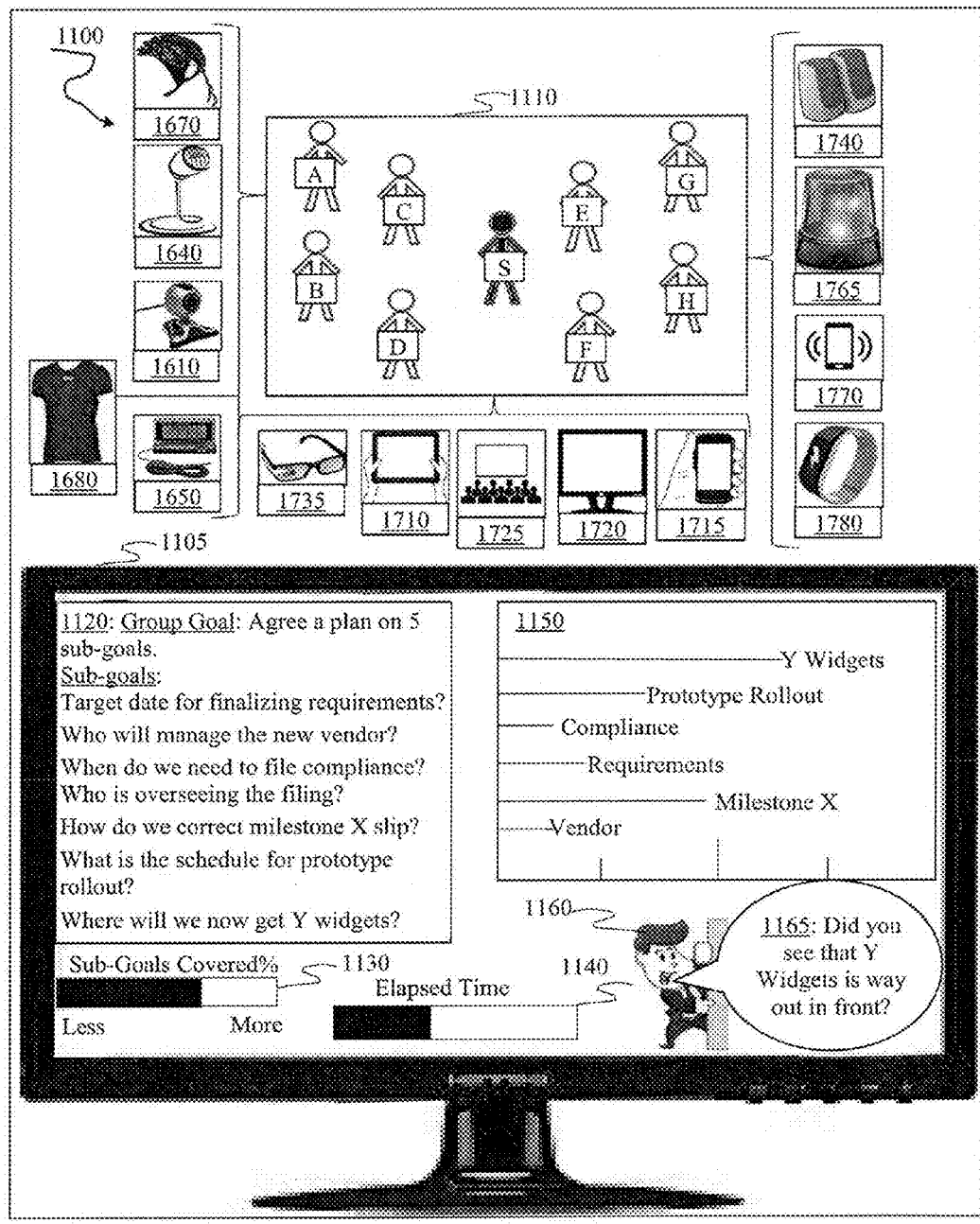
FIG. 11 is a diagram of meeting participants during a discussion. The diagram depicts an example of a business meeting where participants can receive feedback signals about who is talking and their speech delivery, the most often discussed topics, and goal setting and realization.

FIG. 11 is a diagram of a business meeting where a group of people are engaged in a discussion. Devices capture their visually perceptible and sound output biosignals as well as eye behavior, hand temperature, and heart and breathing rates e.g., with a camera 1610, a microphone 1640, a brainwave helmet 1670, a hand temperature sensor 1650, and a T-shirt containing sensors 1680 respectively. Feedback devices render visual, aural, and tactile feedback signals to the student participants 1110A, 1110B, 1110C, 1110D, 1110E, 1110F, 1110G, 1110H, and 1110S. These feedback signals are rendered e.g., to a tablet 1710, a smartphone 1715, a display monitor 1720, a large wall screen display 1725, Google™ Glass™ 1735, speakers 1740, a flashing light 1765, a vibrating smartphone 1770, and a vibrating/shock emitting wristband 1780. The visual display 1105 includes a group goal and sub-goals listing 1120, a progress indicator for the percentage of covered sub-goals 1130, a progress indicator for the elapsed time of the discussion 1140, a word race graph 1150, a meeting system software agent avatar 1160, and the avatar's speech bubble 1165.

To be useful as biofeedback, biofeedback signals rendered via devices e.g., 1710, 1715, 1720, 1725, 1735, 1740, 1765, 1770, and 1780 are presented to the participants 1110A, 1110B, 1110C, 1110D, 1110E, 1110F, 1110G, and 1110S in substantially near real-time, and preferably in near real-time.

The nature of the meeting in this example is one among co-workers within a business environment. Although, meetings among other groups including but not limited to social organizations, charitable organizations, religious organizations, special interest organizations are also considered as other likely examples where meeting biofeedback may altering a discussion. The meeting participants 1110A, 1110B, 1110C, 1110D, 1110E, 1110F, 1110G, 1110H, and 1110S may each have a meeting goal that they want to achieve during the discussion with the Biofeedback Discussion System e.g., 130 and with other meeting participants. Often in a business meeting the agenda has been set by one or a handful of meeting participants and the goal may or may not be clear to all meeting participants and then may only be stated at the culmination of the meeting as meeting outcomes (implying the goal for the meeting). When using the Biofeedback Discussion System, all meeting participants 1110A, 1110B, 1110C, 1110D, 1110E, 1110F, 1110G, 1110H, and 1110S contribute their goals and a group goal is then determined by agreement of all meeting participants with the help of the Biofeedback Discussion System to incorporate all meeting participant goals into a group goal to be achieved during the discussion.

Usefulness of biofeedback signals to participants 1110A, 1110B, 1110C, 1110D, 1110E, 1110F, 1110G, 1110H, and 1110S is very likely related to the amount, quality and relevance of information provided to the system. For example, for meeting participants, discussions are mostly centered on their agenda, work output, budget, schedule, manpower, reports, and prior discussion meeting data. Some preferred embodiments will automatically load the participants' data (e.g., as part of initialization data 310) from prior meeting sessions and populate the rendered feedback signals accordingly; incorporating this data for the start of the current discussion.

In this meeting discussion example, there are a group of meeting participants: 1110A, 1110B, 1110C, 1110D, 1110E, 1110F, 1110G, and 1110H. Although a specific number of meeting participants are shown in this example, it is anticipated that there may be any number of meeting participants 1110A, 1110B, 1110C . . . 1110N One of the participants not included in this group is the current speaker 1110S the discussion. The role of meeting speaker changes during the discussion so that any of the meeting participants 1110A, 1110B, 1110C, 1110D, 1110E, 1110F, 1110G, or 1110H can be the speaker as is normal during a business meeting. The letter 'S' signifier would then be conferred upon whichever participant is speaking at the time and the prior speaker would be conferred the 'A', 'B', 'C', 'D', 'E', 'F', 'G', or 'H' signifier accordingly.

Meeting participants 1110A, 1110B, 1110C, 1110D, 1110E, 1110F, 1110G, 1110H, and 1110S can all be located in the same room or each meeting participant can access the meeting using the Biofeedback Discussion System from varied locations. The diagram further delineates the speaker 1110S as such by showing the human stick-figure darker than the other meeting participant stick figures.

Meeting participants 1110A, 1110B, 1110C, 1110D, 1110E, 1110F, 1110G, 1110H, and 1110S provide many different types of information to the system. One type is particular to meetings including but not limited to an agenda, work output, budget, schedule, manpower, and reports. Another type of information is sensor derived information from a heart and breathing rate T-shirt e.g., 1680, a brainwave headset e.g., 1670, a hand temperature sensor e.g., 1650, and a standard microphone e.g., 1640, and camera e.g., 1610 all to capture their biosignals. Feedback signal are rendered to meeting participants 1110A, 1110B, 1110C, 1110D, 1110E, 1110F, 1110G, 1110H, and 1110S via e.g., to a tablet 1710, a smartphone 1715, a display monitor 1720, a large wall screen display 1725, Google™ Glass™ 1735, speakers 1740, a flashing light 1765, a vibrating smartphone 1770, and a vibrating/shock emitting wristband 1780.

Meeting participants 1110A, 1110B, 1110C, 1110D, 1110E, 1110F, 1110G, 1110H, and 1110S, attending the meeting, want to ensure that the meeting agenda items are discussed while at the same time they want to achieve their own meeting goals; here listed as sub-goals 1120. The motivation for using the Biofeedback Discussion System can be to keep track of multi-part agenda items linked to one or more sub-goals, ensure that all agenda and sub-goals items are sufficiently covered during the allotted meeting time, and they may want to ensure that one or more meeting participants do not dominate the discussion as can happen in many business meetings.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Meeting participant 1110A, 1110B, 1110C, 1110D, 1110E, 1110F, 1110G, 1110H, and 1110S, emit biosignals while engaged in their meeting discussion. Biofeedback signals for heart rate, breathing rate, voice anger, content anger, eye movement, pupil dilation, hand temperature, and fidgeting and gestures (both general body and hand and limb movement) are categorized. Measurement of heart rate and breathing rate biosignals are obtained whereby the meeting participants 1110A, 1110B, 1110C, 1110D, 1110E, 1110F, 1110G, 1110H, and 1110S wear clothing containing sensors, e.g., a T-shirt 1680. The meeting participants' voice anger and content anger (when the meeting participant is the speaker) is obtained by a microphone, e.g., 1640. The meeting participants' eye movement and pupil dilation biosignal is obtained by a camera, e.g., 1610. The meeting participants' hand temperature is obtained whereby the meeting participants affix a hand temperature sensor, e.g., 1650 to their finger. The meeting participants' fidgeting and gesture biosignals are obtained by that participant's actions being observed by a camera, e.g. 1610.

Meeting participants' 1110A, 1110B, 1110C, 1110D, 1110E, 1110F, 1110G, 1110H, and 1110S feedback signals are rendered by the Biofeedback Discussion System e.g., 310. The meeting system software agent 1160 will respond and notify a meeting participant if the participant's heart rate or breathing rate exceeds normal values or the hand temperature device e.g., 1650 shows that they are stressed and ask them to breathe deeply and take a break from the discussion for a minute or two in order to calm down. For any participant who is identified as stressed, their smartphone will vibrate or their wristband will vibrate to remind them to remain calm. A participant's wristband will emit a mild shock if the meeting participant's pupil dilation goes below a threshold showing lack of concentration or if the camera shows fidgeting or hand or arm movement that shows that the meeting participant is distracted and their attention is waning. A harsh audio tone will sound through the speakers e.g., 1740 and a participant's Google™ Glass™ e.g., 1735 will beep if the Biofeedback Discussion System has determined that a particular speaker or speakers is/are dominating the discussion on a particular topic based on the number of sub-goals that the meeting participants have agreed to cover during the meeting and the total time allocated for the meeting. A flashing light is activated if any participant uses content anger (anger words), uses a loud voice (out of normal talking range as in shouting), or uses accusatory hand gestures or facial expressions. Meeting participants 1110A, 1110B, 1110C, 1110D, 1110E, 1110F, 1110G, 1110H, and 1110S are likely to respond to these feedback signals as they are rendered and possibly alter their discussion.

Feedback signals are rendered visually to the meeting participants 1110A, 1110B, 1110C, 1110D, 1110E, 1110F, 1110G, 1110H, and 1110S by the Biofeedback Discussion System e.g. 130. The meeting participants would see these feedback signals rendered via the tablet e.g., 1710, a smartphone e.g., 1715, a display monitor e.g., 1720, a large wall screen display e.g., 1725. In this example, a view of the visual display 1105 shows example feedback signal renderings that include, but is not limited to a group goal and sub-goals listing 1120, a progress indicator for the percentage of covered sub-goals 1130, a progress indicator for the elapsed time of the discussion 1140, a word race graph 1150, a meeting system software agent avatar 1160, and the avatar's speech bubble 1165.

A listing of the meeting participants' 1110A, 1110B, 1110C, 1110D, 1110E, 1110F, 1110G, 1110H, and 1110S group goal and sub-goals 1120 informs the participants of what they will be discussing during the meeting. The meeting group goal is set by the meeting organizer or manager at the beginning of the discussion, rendered at 1120, and the group goal is submitted to the Biofeedback Discussion System e.g. 130. Meeting participants also submit their goals to the Biofeedback Discussion System before the discussion begins. The Biofeedback Discussion System then analyzes each meeting participant's goal against the meeting group goal that has been suggested by the meeting organizer. The Biofeedback Discussion System then asks the meeting participants to vote on each of the meeting participant goals they submitted; as to whether each goal being voted on is in line with the group goal or is outside of the group goal. Each goal that is voted as being in line with the group goal becomes a meeting sub-goal and is rendered at 1120 as a sub-goal. Any meeting participant goals that have been determined to be outside the scope of the suggested group goal are presented again to the meeting participants by the Biofeedback Discussion System and the meeting participants are asked to vote on either changing the group goal to incorporate the meeting participant's goal that have been so far excluded or to add the out-of-topic meeting participant goal to the meeting transcript as a goal that needs to be addressed in subsequent meetings. If the group goal has been altered by the meeting participant voting, then the rendering of the group goal for the meeting participants is updated in the display at 1120. Meeting participants seeing the group goal and sub-goals will be reminded of their sub-goal contribution or of the number of sub-goals pertaining to a particularly important topic requiring resolution and will therefore bring those one or more sub-goals to the attention of the other meeting participants to ensure that the sub-goal(s) have been sufficiently covered during the discussion. Other participants may notice the amount of time remaining in the meeting and also notice that one or more sub-goals have not yet been discussed and then interject into the discussion that a specific sub-goal requires discussion, thus altering the subsequent meeting discussion.

A sliding-scale measure 1130 represents the percentage of sub-goals that have been discussed as a portion of all of the agreed sub-goals covered during the discussion. Prior to starting the discussion, the meeting participants 1110A, 1110B, 1110C, 1110D, 1110E, 1110F, 1110G, 1110H, and 1110S state and agree their personal goals as related to the group goal for the meeting so that when the sub-goals are grouped together they become the basis for the discussion. The black portion of the sub-goals covered box, signifies the portion as a percentage of the all the sub-goals that have been discussed during the discussion so far. The sub-goals covered rendering is provided as a tool to help the meeting Participants manage the time that they have allocated and to ensure that each meeting participant can speak up in time to make sure that their sub-goal is discussed before the meeting ends.

A sliding-scale measure 1140 represents the time that has elapsed so far during the discussion. Prior to starting the discussion a meeting participant states how long the meeting is to last to the Biofeedback Discussion System e.g. 130. The black portion of the elapsed time box, signifies the portion of the total time set aside for the discussion that has already elapsed. The portion of time is measured as a percentage of the whole time allocated for the discussion. The time elapsed rendering is provided as a tool to help the meeting participants 1110A, 1110B, 1110C, 1110D, 1110E, 1110F, 1110G, 1110H, and 1110S manage the time that they have allocated in order to best achieve their meeting discussion goal. When the elapsed time measurement approaches 90% completion, the Biofeedback Discussion System will notify or remind the meeting participants (by way of the meeting system software agent speech bubble 1155) that the discussion time is nearing completion. When the elapsed time measurement approaches 95% completion, the Biofeedback Discussion System will suggest to the meeting participants (by way of the meeting system software agent speech bubble 1165) that they need to wrap up the meeting and assess which sub-goals have been discussed and achieved during the discussion and what sub-goals, if any, have yet to be addressed or completed. An assessment of whether the group goal has been achieved or not should then also be evaluated by the meeting participants and will become part of the meeting transcript maintained by the Biofeedback Discussion System.

A word race graph 1150 renders the most used words spoken and written by meeting participants 1110A, 1110B, 1110C, 1110D, 1110E, 1110F, 1110G, 1110H, and 1110S during the discussion. The word race graph shows the most often spoken (or typed-text) words in a race. The most frequently spoken (or typed-text) words during the meeting discussion are tabulated (counted) and the top words are selected for rendering; in this example there are six (6) words selected for rendering. These top words are then compared to the total number of words spoken so far during the meeting and a percentage of that particular word with respect to the total number of words spoken is calculated. The word is then rendered in the word race graph and placed at the percentage point (where 0% is at the left-hand side of the graph, 50% is at the middle of the graph, and 100% is at the right-hand side of the graph) representing that word's frequency calculation. The vertical lines at the bottom of the graph represent the 25%, 50%, and 75% markers from right to left. The horizontal lines represent the frequency calculation result for each of the six words. The endpoint of each line, at the right-hand side of the line, signify the frequency calculation result for that word. The word itself is rendered to the right of the word race graph line. Words that are not considered when identifying the most frequently used words do not include adjectives, prepositions, and other words including but not limited to in this non-exhaustive list: good, new, last, long, great, little, own, other, old, right, big, high, different, small, large, next, early, young, important, few, public, bad, same, able, to, of, in, for, on, with, at, by, from, up, about, into, over, after, beneath, under, above, the, and, a, that, I, it, not, he, as, you, this, but, his, they, her, she, or, an, will, my, one, all, would, there, their. The meeting Participants seeing the rendering of most used words are kept aware of the content of their meeting discussion and can easily determine whether the group of most used words cover the sub-goal topics that are set as a goal to be covered during the discussion. A meeting participant noticing the elapsed time reading 1140, the sub-goals covered 1130, and the word race graph 1150 can see that although the vendor sub-goal has at least been mentioned, it has not been given sufficient attention to have resolved the new vendor issues and so that meeting participants will alter the discussion by bringing this information to the attention of the other meeting participants and thereby alter the discussion. It is anticipated that the visual rendering of the word race graphic to meeting participants will be compelling such that meeting participants will possibly want to alter the discussion to ensure that a particularly important word is used, and therefore the sub-goals that include those important words will be discussed to the participants' satisfaction.

The meeting system software agent 1160 is the system interface between the participants 1110A, 1110B, 1110C, 1110D, 1110E, 1110F, 1110G, 1110H, and 1110S and the Biofeedback Discussion System e.g., 130. The meeting system Software Agent Behavior e.g., 315 is embodied by the meeting system software agent avatar and is driven by the Discussion Altering Machine e.g., 320. Focusing back on FIG. 11, the system has rendered a visual representation of the meeting system software agent as a businessman avatar. The meeting system software agent participates in a discussion with the meeting participants 1110 (any one or a combination of the meeting participants) to provide feedback signals in the form of responses to meeting Participant feedback signals 1120, 1130, 1140, and 1150 and to respond to meeting participant questions asked of the Biofeedback Discussion System should they occur.

A speech bubble 1165 is used by the meeting system software agent 1160 to carry on the discussion with the meeting participants 1110 (any one of the meeting participants). Although it is anticipated that the meeting system software agent 1160 will have the capability of aural speech, this embodiment implies both the additional aural speech discussion capability as well as the textual discussion capability via the example of the feedback signal rendered as visual text.

Figure 12:
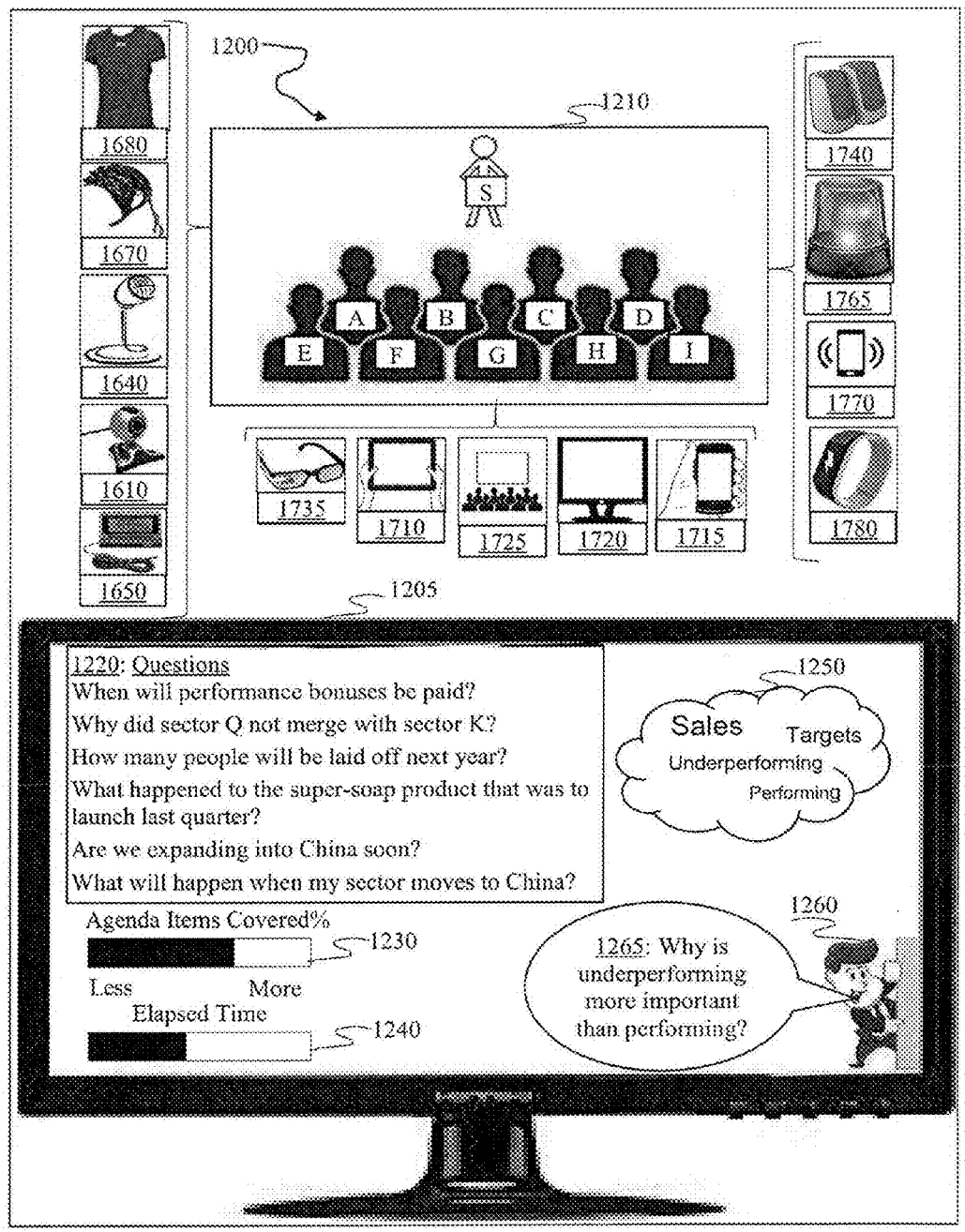
FIG. 12 is a diagram of conference participants during a discussion. The diagram depicts an example of a business or professional conference where participants are made aware of the speaker's and other participant's biosignals, can track topics discussed, and can interact with an AI System to ask questions during the discussion.

FIG. 12 is a diagram of a group of people engaged in a discussion. Devices capture their visually perceptible and sound output biosignals as well as eye behavior, hand temperature, and heart and breathing rates e.g., with a camera 1610, a microphone 1640, a brainwave helmet 1670, a hand temperature sensor 1650, and a T-shirt containing sensors 1680 respectively. Feedback devices render visual, aural, and tactile feedback signals to the conference participants 1210A, 1210B, 1210C, 1210D, 1210E, 1210F, 1210G, 1210H, 1210I and 1210S. These feedback signals are rendered e.g., to a tablet 1710, a smartphone 1715, a display monitor 1720, a large wall screen display 1725, Google™ Glass™ 1735, speakers 1740, a flashing light 1765, a vibrating smartphone 1770, and a vibrating/shock emitting wristband 1780. The visual display 1205 includes a list of questions 1220, a progress indicator for the percentage of agenda items covered 1230, a progress indicator for the elapsed time of the discussion 1240, a word cloud 1250, a conference system software agent avatar 1260, and the avatar's speech bubble 1265.

To be useful as biofeedback, biofeedback signals rendered via devices e.g., 1710, 1715, 1720, 1725, 1735, 1740, 1765, 1770, and 1780 are presented to the conference participants 1210A, 1210B, 1210C, 1210D, 1210E, 1210F, 1210G, 1210H, 1210I and 1210S in substantially near real-time, and preferably in near real-time.

The nature of the conference in this example is one among co-workers or domain specific colleagues within a business environment. Although this example is about business conferences, other groups attending conferences including but not limited to social organizations, charitable organizations, religious organizations, special interest organizations are also considered as likely embodiments for conference biofeedback altering their discussion.

Conferences and seminars could be considered as a fairly similar types of business or other domain group meetings. In examples 1200 and 1300, the differences between conferences and seminars are time duration where a conference is typically is held over multiple days and a seminar would likely be held over a few hours during one day or may be held for one day in total and one of subject matter where conferences often include multiple tracks of topic areas whereas seminar agenda items typically consist of only one topic area. In this conference example, there would be multiple discussions each of duration is about 1-2 hours day where each discussion may be linked to other discussions covering similar topics whereas the seminar agenda would cover only one topic area during one discussion.

The conference participants include a conference speaker 1210S and a group of conference attendees 1210A, 1210B, 1210C, 1210D, 1210E, 1210F, 1210G, 1210H, 1210I. Although a specific number of conference attendees are shown in this example, it is anticipated that there may be any number of conference attendees 1210A, 1210B, 1210C . . . 1210N. The 1210S attendee is the special case of the speaker. Herein the conference participants are referred to as a conference speaker and conference attendees respectively and as a group they are conference participants.

The conference participants may each have a conference goal that they want to achieve during the discussion with the Biofeedback Discussion System e.g., 130 and with other conference participants. Often in a business conference the agenda has been set by one or a handful of conference leaders or organizers and the goal may or may not be clear to all conference participants. Conference goals may only be stated at the end of the conference as outcomes (implying the goal for the conference). When using the Biofeedback Discussion System, the goal of the conference speaker 1210S is to cover all agenda items within the time allotted 1240 for the conference and to answer conference attendee questions 1220. Whereas the goal of all conference participants 1210A, 1210B, 1210C, 1210D, 1210E, 1210F, 1210G, 1210H, and 1210I when using the Biofeedback Discussion System, is to ensure that their particular interest that is included in at least one of the items of the agenda list or questions list and is discussed during the conference to the satisfaction of that conference participant.

Usefulness of biofeedback signals to conference attendees 1210A, 1210B, 1210C, 1210D, 1210E, 1210F, 1210G, 1210H, 1210I and conference speaker 1210S is very likely related to the amount, quality and relevance of information provided to the system. Conference discussions outlined in a conference agenda often transpire over several days and the discussions would be organized into multiple topic tracks over that course of days. Discussions within the same topic track may be sufficiently related to each other such that information that the Biofeedback Discussion System e.g., 130 derived from one discussion may be useful in subsequent discussions. So relevant information provided to the system, for conference participants, for a current discussions are mostly centered on the specific topic agenda within the greater conference agenda, information from prior related discussions from the conference, and the speaker's 1210S background and career artifacts. Some preferred embodiments will automatically load the speaker's data (e.g., as part of initialization data 310) and populate the rendered feedback signals accordingly; incorporating this data for the start of the current discussion.

The conference speaker 1210S is a special case conference participant. The conference speaker has either compiled the agenda items alone or together with the conference sponsor or organizer. The conference speaker leads the discussion by presenting the agenda items and the detailed content information pertaining to the agenda list to the conference attendees 1210A, 1210B, 1210C, 1210D, 1210E, 1210F, 1210G, 1210H, and 1210I. In this example, conference attendees can see the conference speaker and all the conference attendees in human form at the conference during the discussion; although in other conference embodiment examples the conference speaker and one or more conference attendees can participate in the conference from a remote location.

Conference speaker 1210S provides many different types of information to the system. One type is particular to conferences including but not limited to an agenda, their background information, and career artifacts. Another type of information is sensor derived information from a heart and breathing rate T-shirt e.g., 1680, a brainwave headset e.g., 1670, a hand temperature sensor e.g., 1650, and a standard microphone e.g., 1640, and camera e.g., 1610 all to capture their biosignals. Feedback signal are rendered to the conference speaker 1210S via any of e.g., to a tablet 1710, a smartphone 1715, a display monitor 1720, a large wall screen display 1725, or Google™ Glass™ 1735. Other feedback signals are rendered to the conference speaker 1210S via e.g., speakers 1740, a flashing light 1765, a vibrating smartphone 1770, and/or a vibrating/shock emitting wristband 1780.

Conference attendees 1210A, 1210B, 1210C, 1210D, 1210E, 1210F, 1210G, 1210H, and 1210I provide many different types of information to the system. One type is particular to conferences for example questions based on the agenda and the discussion. Another type of information is sensor derived information from a heart and breathing rate T-shirt e.g., 1680, a brainwave headset e.g., 1670, a hand temperature sensor e.g., 1650, and a standard microphone e.g., 1640, and camera e.g., 1610 all to capture their biosignals. Feedback signals are rendered to the conference attendees 1210A, 1210B, 1210C, 1210D, 1210E, 1210F, 1210G, 1210H, and 1210I via any of e.g., to a tablet 1710, a smartphone 1715, a display monitor 1720, a large wall screen display 1725, or Google™ Glass™ 1735. Other feedback signals are rendered to the conference attendees 1210A, 1210B, 1210C, 1210D, 1210E, 1210F, 1210G, 1210H, and 1210I via e.g., speakers 1740, a flashing light 1765, a vibrating smartphone 1770, a vibrating/shock emitting wristband 1780. The conference attendees are assumed to use a varying combination of sensors and feedback rendering devices herein identified for use during the discussion.

The conference speaker 1210S wants to ensure that all agenda items are covered to the satisfaction of conference attendees 1210A, 1210B, 1210C, 1210D, 1210E, 1210F, 1210G, 1210H, and 1210I as well as allocating sufficient time to answer conference attendee questions. The conference speaker also wants to remain aware of their own behavior during the discussion.

Conference attendees 1210A, 1210B, 1210C, 1210D, 1210E, 1210F, 1210G, 1210H, and 1210I want to ensure that the conference agenda items are discussed and that their questions are answered during the time allotted for the conference. The motivation for conference attendees using the Biofeedback Discussion System can be to keep track of percentage of agenda items covered during the allotted conference time, to watch which topic words are dominating the discussion, and to remain aware of the list of conference attendee questions 1220 to make sure their question appears on the list and that the speaker 1210S is using time wisely so that their question will be answered during the discussion.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Conference speaker 1210S emits biosignals while engaged in the conference discussion. Biofeedback signals for heart rate, breathing rate, voice anger, content anger, eye movement, pupil dilation, hand temperature, and fidgeting and gestures (both general body and hand and limb movement) are categorized. Measurement of heart rate and breathing rate biosignals are obtained whereby the conference speaker 1210S wears clothing containing sensors, e.g., a T-shirt 1680. The conference speaker's voice anger and content anger (anger words) is obtained by a microphone, e.g., 1640. The conference speaker's eye movement and pupil dilation biosignal is obtained by a camera, e.g., 1610. The conference speaker's hand temperature is obtained whereby the conference speaker affixes a hand temperature sensor, e.g., 1650 to their finger. The conference speaker's fidgeting and gesture biosignals are obtained by that conference speaker's actions being observed by a camera, e.g. 1610.

Conference attendees 1210A, 1210B, 1210C, 1210D, 1210E, 1210F, 1210G, 1210H, and 1210I emit biosignals while engaged in the conference discussion. Biofeedback signals for heart rate, breathing rate, hand temperature, and fidgeting and gestures (both general body and hand and limb movement) are categorized. Measurement of heart rate and breathing rate biosignals are obtained whereby the conference attendees 1210A, 1210B, 1210C, 1210D, 1210E, 1210F, 1210G, 1210H, and 1210I wear clothing containing sensors, e.g., a T-shirt 1680. The conference attendees' hand temperature is obtained whereby the conference attendees affix a hand temperature sensor, e.g., 1650 to their fingers. The conference attendees' fidgeting and gesture biosignals are obtained by that conference attendee's actions being observed by a camera, e.g. 1610.

Conference speaker's 1210S feedback signals are rendered by the Biofeedback Discussion System e.g., 310. The conference speaker's wristband e.g., 1780 will vibrate or their Google™ Glass e.g., 1735 will register a notification if the conference speaker's heart rate or breathing rate exceeds normal values or their hand temperature device e.g., 1650 shows that they are stressed; reminding them to breathe deeply in order to calm down. The conference speaker's wristband will emit a mild shock if the camera observes eye movement behavior that signifies lying. A flashing light e.g., 1765 will activate if the conference speaker is talking too loudly (out of normal talking range as in shouting) or is using content anger (anger words) or negative gestures or facial expressions. The conference system software agent 1260 will notify the conference speaker (either verbally or in the avatar's speech bubble 1265) if the conference timing is insufficient to cover all agenda items and conference participant questions.

Conference attendees 1210A, 1210B, 1210C, 1210D, 1210E, 1210F, 1210G, 1210H, and 1210I feedback signals are rendered by the Biofeedback Discussion System e.g., 310. Conference attendees will be notified by their vibrating wristband e.g., 1780 or vibrating smartphone e.g., 1770 if the conference attendee's heart rate or breathing rate exceeds normal values or the hand temperature device e.g., 1650 shows that they are stressed to remind them to breathe deeply and maybe take a break from the discussion for a minute or two in order to calm down. If conference attendees' brainwave helmets e.g., 1670 or the camera e.g., 1610 detect that a conference attendees shows signs of losing concentration (are bored) during the discussion, the conference attendees' wristbands e.g., 1780 will emit a mild shock or when appropriate (when a certain percentage of conference attendees' biosignals show the same inattentive behavior) the speakers e.g., 1740 will sound a foghorn. Conference attendees 1210A, 1210B, 1210C, 1210D, 1210E, 1210F, 1210G, 1210H, and 1210I are likely to respond to these feedback signals as they are rendered and possibly alter their discussion.

Feedback signals are rendered visually to the conference attendees 1210A, 1210B, 1210C, 1210D, 1210E, 1210F, 1210G, 1210H, 1210I and conference speaker 1210S by the Biofeedback Discussion System e.g. 130. The seminar speaker would likely see these feedback signals rendered via a display monitor e.g., 1720 or a large wall screen display e.g. 1725. The conference attendees would see these feedback signals rendered via a tablet e.g., 1710, a smartphone e.g., 1715, a display monitor e.g., 1720, or a large wall screen display e.g. 1725. In this example, a view of the visual display 1205 shows example feedback signal renderings that include a list of questions 1220, a progress indicator for the percentage of agenda items covered 1230, a progress indicator for the elapsed time of the discussion 1240, a word cloud 1250, a conference system software agent avatar 1260, and the avatar's speech bubble 1265.

A list of questions 1220 posed by conference attendees 1210A, 1210B, 1210C, 1210D, 1210E, 1210F, 1210G, 1210H, and 1210I is rendered. During the discussion, conference attendees can add questions to the list. New questions added by conference attendees are appended (added to the bottom) of the list. Questions added to the questions list 1220 are to be answered by the conference speaker 1210S aurally during the discussion or at the minimum, saved in the conference transcript. As questions are answered by the conference speaker 1210S, they are removed from the questions list 1220. Seeing the questions list may prompt conference attendees to ask a question that they hadn't thought of until prompted by a question already posted on the list 1220.

A sliding-scale measure 1230 of the percentage of agenda items that have been discussed as a portion of all of the scheduled agenda items for the discussion. Prior to starting the conference discussion, the conference speaker 1210S or a conference organizer will have submitted an agenda for the conference to the Biofeedback Discussion System e.g., 130. The black portion of the agenda items covered box, signifies the portion of agenda items discussed as a percentage of the all the agenda items that were scheduled for the discussion. The agenda items covered is rendered and is provided as a tool to help the conference attendees 1210A, 1210B, 1210C, 1210D, 1210E, 1210F, 1210G, 1210H, and 1210I and conference speaker 1210S manage the time that they have allocated and to ensure that each agenda item 1230 has been covered and that each conference attendee has had their question answered or at least acknowledged and added to the conference transcript as open items that require further discussion before the conference ends. Seeing the how much of the total agenda items have been covered may prompt the conference speaker 1210S to move to the next agenda item or answer a question quickly; thus altering the discussion.

A sliding-scale measure 1240 represents the time that has elapsed during the discussion. Time allotted for the conference has been predetermined by the conference speaker or the organization managing the conference. The black portion of the elapsed time box, signifies the portion of the total time set aside for the discussion that has already elapsed. The portion of time is measured as a percentage of the whole time allocated for the discussion. The time elapsed rendering is provided as a tool to help the conference speaker 1210S manage the time that they have allocated in order to best achieve their conference discussion goals. When the elapsed time measurement approaches 90% completion, the Biofeedback Discussion System will notify or remind the conference participants (by way of the conference system software agent speech bubble 1265) that the discussion time is nearing completion. When the elapsed time measurement approaches 95% completion, the Biofeedback Discussion System will suggest to the conference participants (by way of the conference system software agent speech bubble 1265) that they need to wrap up the conference and assess which agenda items have been discussed and achieved during the discussion and what agenda items, if any, have yet to be addressed or completed.

A tag cloud graph 1250 renders the most used words spoken and written by conference participants during the discussion. The tag cloud graphic renders the most used words in the most prominent manner either by using a larger font size than other words of lesser importance to render the words, by using brighter colors for the most often used words, or by some other means of visual significance within the graphical rendering space that signifies that a particular word is more significant or important or at least more often used during the discussion than other words. The list of commonly used words does not include adjectives, preposition, and other words including but not limited to in this non-exhaustive list: good, new, first, last, long, great, little, own, other, old, right, big, high, different, small, large, next, early, young, important, few, public, bad, same, able, to, of, in, for, on, with, at, by, from, up, about, into, over, after, beneath, under, above, the, and, a, that, I, it, not, he, as, you, this, but, his, they, her, she, or, an, will, my, one, all, would, there, their. The conference participants seeing the rendering of most used words are kept aware of the content of their conference discussion and can easily determine whether the group of most used words cover the sub-goal topics that are set as a goal to be covered during the discussion. A conference attendee (one of 1210A, 1210B, 1210C, 1210D, 1210E, 1210F, 1210G, 1210H, or 1210I) noticing the elapsed time reading 1240, the agenda items covered 1230, and the tag cloud 1250 can see that although the top performers agenda item has at least been mentioned, the discussion has not given sufficient attention as many top performers who have received awards have yet to be mentioned. That conference attendee (one of 1210A, 1210B, 1210C, 1210D, 1210E, 1210F, 1210G, 1210H, or 1210I) will then alter the discussion by bringing this information to the attention of the other conference attendees and the conference speaker; thereby altering the discussion.

The conference system software agent 1260 is the system interface between the conference attendees 1210A, 1210B, 1210C, 1210D, 1210E, 1210F, 1210G, 1210H, and 1210I, the conference speaker 1210S, and the Biofeedback Discussion System e.g., 130. The conference system Software Agent Behavior e.g., 315 embodied by the conference system software agent avatar 1260 and is driven by the Discussion Altering Machine e.g., 320. Focusing back on FIG. 12, the system has rendered a visual representation of the conference system software agent as a businessman avatar. The conference system software agent participates in a discussion with the conference attendees (any one or a combination of the conference attendees) and the speaker 1210S to provide feedback signals in the form of responses to conference participant feedback signals 1220, 1230, 1240, and 1250 and to respond to conference attendee or speaker questions asked of the Biofeedback Discussion System should they occur.

A speech bubble 1265 is used by the conference system software agent 1260 to carry on the discussion with the conference attendees 1210A, 1210B, 1210C, 1210D, 1210E, 1210F, 1210G, 1210H, and 1210I (any one of the conference attendees) and the conference speaker 1210S. Answers to any questions answered by the conference system software agent 1260 during the discussion will be rendered as text in the speech bubble unless the system software avatar is enabled to respond to the question aurally. Although it is anticipated that the conference system software agent 1260 will have the capability of aural speech, this embodiment implies both the additional aural speech discussion capability as well as the textual discussion capability via the example of the feedback signal rendered as visual text.

Figure 13:
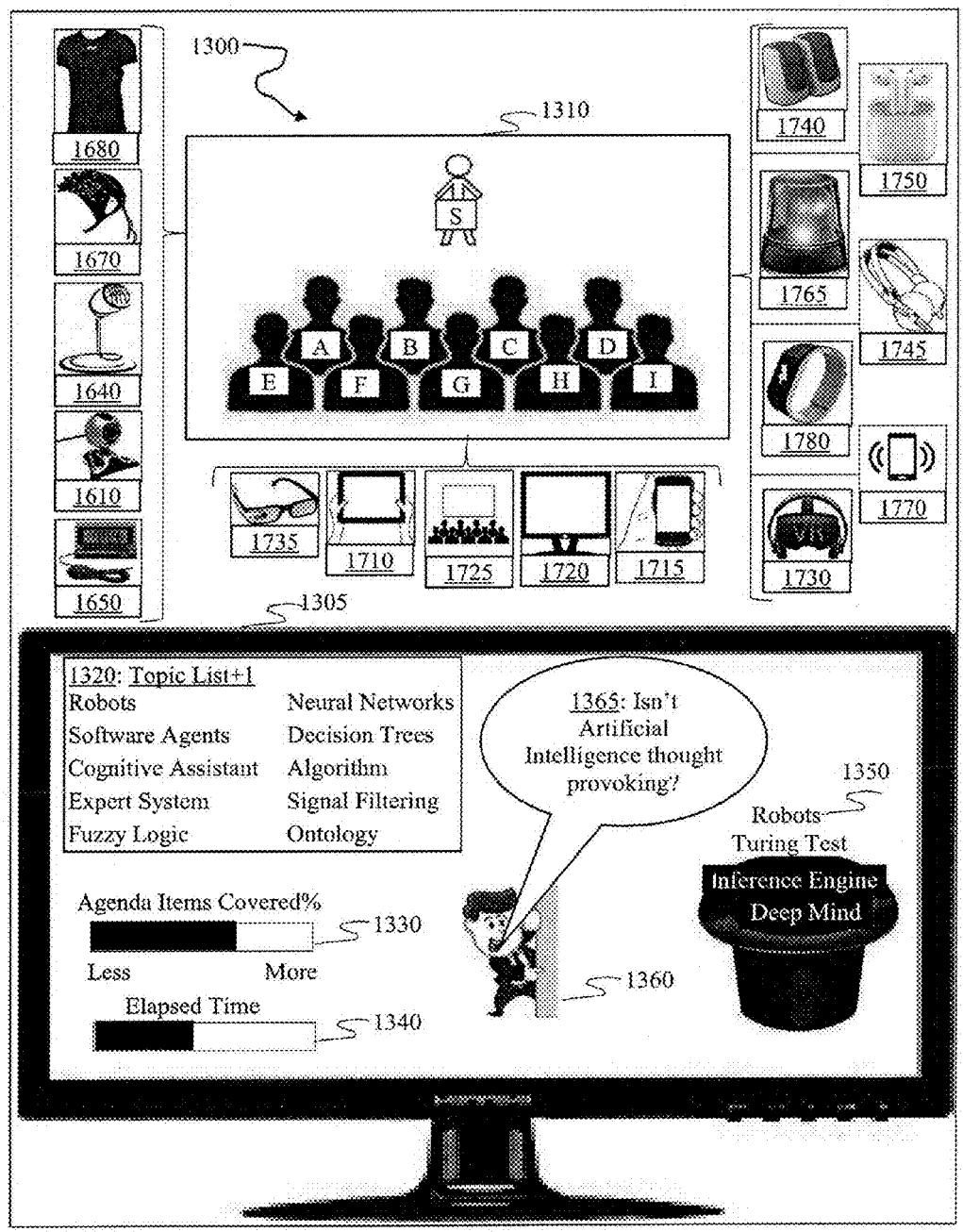
FIG. 13 is a diagram of seminar participants during a discussion. The diagram depicts a technical seminar where participants are provided feedback signals about the speaker, as well as their fellow participants. Information from the speaker's portion of speech is categorized by an AI System supported Discussion Altering Machine that generates topical information rendered to the participants in substantially near real-time.

FIG. 13 is a diagram of a seminar attended by a group of people. Devices capture their visually perceptible and sound output biosignals as well as eye behavior, hand temperature, and heart and breathing rates e.g., with a camera 1610, a microphone 1640, a brainwave helmet 1670, a hand temperature sensor 1650, and a T-shirt containing sensors 1680 respectively. Feedback devices render visual, aural, and tactile feedback signals to the seminar participants 1310A, 1310B, 1310C, 1310D, 1310E, 1310F, 1310G, 1310H, 1310I and 1310S. These feedback signals are rendered e.g., to a tablet 1710, a smartphone 1715, a display monitor 1720, a large wall screen display 1725, Virtual Reality (VR)/Augmented Reality (AR) headset 1730, Google™ Glass™ 1735, speakers 1740, headphones 1745, AirPods™ 1750, a flashing light 1765, a vibrating smartphone 1770, and a vibrating/shock emitting wristband 1780. The visual display 1305 includes a Topic List+1 1320, a progress indicator for the percentage of agenda items covered 1330, a progress indicator for the elapsed time of the discussion 1340, a word hat 1350, a seminar system software agent avatar 1360, and the avatar's speech bubble 1365.

To be useful as biofeedback, biofeedback signals rendered via devices e.g., 1710, 1715, 1720, 1725, 1730, 1735, 1740, 1745, 1750, 1765, 1770, and 1780 are presented to the seminar participants 1310A, 1310B, 1310C, 1310D, 1310E, 1310F, 1310G, 1310H, 1310I and 1310S in substantially near real-time, and preferably in near real-time.

The nature of the seminar in this example is one among industry peers within a business environment. Although this example is about business seminars, other groups attending seminars including but not limited to social organizations, charitable organizations, religious organizations, special interest organizations are also considered as likely embodiments for seminar biofeedback altering their discussion.

Seminars and conferences could be considered as a fairly similar types of business or other domain group meetings. In examples 1300 and 1200 the differences between seminars and conferences are time duration where a seminar would likely be held over a few hours during one day or may be held for one day in total whereas a conference typically is held over multiple days and one of subject matter where seminar agenda items typically consist of only one topic area whereas conferences often include multiple tracks of topic areas. In this seminar example, the discussion duration is about ½ day and the seminar agenda covers only one topic area.

The seminar participants include a seminar speaker 1310S and a group of seminar attendees 1310A, 1310B, 1310C, 1310D, 1310E, 1310F, 1310G, 1310H, and 1310I. Although a specific number of seminar attendees are shown in this example, it is anticipated that there may be any number of seminar attendees 1310A, 1310B, 1310C . . . 1310N. The 1310S attendee is the special case of the speaker. Herein the seminar participants are referred to as a seminar speaker and seminar attendees respectively and as a group they are seminar participants.

The seminar participants may each have a seminar goal that they want to achieve during the discussion with the Biofeedback Discussion System e.g., 130 and with other seminar participants. Often in a business seminar the agenda has been set by one or a handful of seminar leaders and the seminar goal may or may not be clear to all seminar participants and then may only be stated at the end as seminar outcomes (implying the goal for the seminar). When using the Biofeedback Discussion System, the goal of the seminar speaker 1310S is to cover all agenda items within the time allotted 1340 for the seminar and to answer seminar participant questions. Whereas the goal of all seminar attendees 1310A, 1310B, 1310C, 1310D, 1310E, 1310F, 1310G, 1310H, and 1310I when using the Biofeedback Discussion System, is to ensure that their particular interest is included in at least one of the items of the agenda list or questions list and is discussed during the seminar to the satisfaction of that seminar attendee.

Usefulness of biofeedback signals to seminar attendees 1310A, 1310B, 1310C, 1310D, 1310E, 1310F, 1310G, 1310H, and 1310I and seminar speaker 1310S is very likely related to the amount, quality and relevance of information provided to the system. For example, for seminar participants, discussions are mostly centered on the seminar agenda and the speaker's 1310S background and career artifacts. Some preferred embodiments will automatically load the speaker's data (e.g., as part of initialization data 310) and populate the rendered feedback signals accordingly; incorporating this data for the start of the current discussion.

The seminar speaker 1310S is a special case seminar participant. The seminar speaker has either compiled the agenda items alone or together with the seminar sponsor or organizer. The seminar speaker leads the discussion by presenting the agenda items and the detailed content information pertaining to the agenda list to the seminar attendees 1310A, 1310B, 1310C, 1310D, 1310E, 1310F, 1310G, 1310H, and 1310I. In this example, seminar attendees can see the seminar speaker and all the seminar attendees in human form at the seminar during the discussion; although in other seminar embodiment examples the seminar speaker and one or more seminar attendees can participate in the seminar from a remote location.

Seminar speaker 1310S provides many different types of information to the system. One type is particular to seminars including but not limited to an agenda, their background information, and career artifacts. Another type of information is sensor derived information from a heart and breathing rate T-shirt e.g., 1680, a brainwave headset e.g., 1670, a hand temperature sensor e.g., 1650, and a standard microphone e.g., 1640, and camera e.g., 1610 all to capture their biosignals. Feedback signal are rendered to the seminar speaker 1210S via any of e.g., to a tablet 1710, a smartphone 1715, a display monitor 1720, a large wall screen display 1725, or Google™ Glass™ 1735. Other feedback signals are rendered to the seminar speaker 1310S via e.g., speakers 1740, a flashing light 1765, a vibrating smartphone 1770, and/or a vibrating/shock emitting wristband 1780.

Seminar attendees 1310A, 1310B, 1310C, 1310D, 1310E, 1310F, 1310G, 1310H, and 1310I provide many different types of information to the system. One type is particular to seminars for example questions based on the agenda and the discussion. Another type of information is sensor derived information from a heart and breathing rate T-shirt e.g., 1680, a brainwave headset e.g., 1670, a hand temperature sensor e.g., 1650, and a standard microphone e.g., 1640, and camera e.g., 1610 all to capture their biosignals. Feedback signals are rendered to the seminar attendees 1310A, 1310B, 1310C, 1310D, 1310E, 1310F, 1310G, 1310H, and 1310I via any of e.g., to a tablet 1710, a smartphone 1715, a display monitor 1720, a large wall screen display 1725, or Google™ Glass™ 1735. Other feedback signals are rendered to the seminar attendees 1210A, 1210B, 1210C, 1210D, 1210E, 1210F, 1210G, 1210H, and 1210I via e.g., a VR/AR headset 1730, speakers 1740, headphones 1745, AirPods™ 1750, a flashing light 1765, a vibrating smartphone 1770, a vibrating/shock emitting wristband 1780. The seminar attendees are assumed to use a varying combination of sensors and feedback rendering devices herein identified for use during the discussion.

The seminar speaker 1310S wants to ensure that all agenda items are covered to the satisfaction of seminar attendees 1310A, 1310B, 1310C, 1310D, 1310E, 1310F, 1310G, 1310H, and 1310I as well as allocating sufficient time to answer seminar attendee questions. The seminar speaker also wants to remain aware of their own behavior during the discussion.

Seminar attendees 1310A, 1310B, 1310C, 1310D, 1310E, 1310F, 1310G, 1310H, and 1310I want to ensure that the seminar agenda items are discussed and that their questions are answered during the time allotted for the seminar. The motivation for seminar attendees using the Biofeedback Discussion System can be to keep track of percentage of agenda items covered during the allotted seminar time, to see an expanded topic view, to watch which topic words are dominating the discussion, and to remain aware of the list of seminar attendee questions to make sure their question appears on the list and that the speaker 1310S is using time wisely so that their question will be answered during the discussion.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Seminar speaker 1310S emits biosignals while engaged in the seminar discussion. Biofeedback signals for heart rate, breathing rate, voice anger, content anger, eye movement, pupil dilation, hand temperature, and fidgeting and gestures (both general body and hand and limb movement) are categorized. Measurement of heart rate and breathing rate biosignals are obtained whereby the seminar speaker 1210S wears clothing containing sensors, e.g., a T-shirt 1680. The seminar speaker's hand temperature is obtained whereby the seminar speaker affixes a hand temperature sensor, e.g., 1650 to their finger. The seminar speaker's fidgeting and gesture biosignals are obtained by that seminar speaker's actions being observed by a camera, e.g. 1610.

Seminar attendees 1310A, 1310B, 1310C, 1310D, 1310E, 1310F, 1310G, 1310H, and 1310I emit biosignals while engaged in the seminar discussion. Biofeedback signals for heart rate, breathing rate, hand temperature, and fidgeting and gestures (both general body and hand and limb movement) are categorized. Measurement of heart rate and breathing rate biosignals are obtained whereby the seminar attendees 1310A, 1310B, 1310C, 1310D, 1310E, 1310F, 1310G, 1310H, and 1310I wear clothing containing sensors, e.g., a T-shirt 1680. The seminar attendees' voice anger and content anger (anger words measured when the seminar attendee is asking questions verbally) is obtained by a microphone, e.g., 1640. The seminar attendees' hand temperature is obtained whereby the seminar attendees affix a hand temperature sensor, e.g., 1650 to their fingers. The seminar attendees' fidgeting and gesture biosignals are obtained by that seminar attendee's actions being observed by a camera, e.g. 1610.

Seminar speaker's 1310S feedback signals are rendered by the Biofeedback Discussion System e.g., 310. The seminar speaker's wristband e.g., 1780 will vibrate or their Google™ Glass e.g., 1735 will register a notification if the seminar speaker's heart rate or breathing rate exceeds normal values or their hand temperature device e.g., 1650 shows that they are stressed; reminding them to breathe deeply in order to calm down. The seminar speaker's wristband will emit a mild shock if the microphone detects that the speaker is talking too loudly (out of normal talking range as in shouting) or too quickly. A foghorn will sound from e.g., VR/AR headset earphones 1730, speakers 1740, headphones 1745, and AirPods™ 1750 for all participants if the seminar speaker is using content anger (anger words) or negative gestures or facial expressions. A harsh audio tone is sounded to e.g., VR/AR headset earphones 1730, speakers 1740, headphones 1745, and AirPods™ 1750 for all participants if the speaker has been talking too long on one topic based on the remaining seminar time and remaining topics and questions to be answered. The seminar system software agent 1360 will notify the seminar speaker (either verbally or in the avatar's speech bubble 1365) if the seminar timing is insufficient to cover all agenda items and seminar participant questions.

Seminar attendees 1310A, 1310B, 1310C, 1310D, 1310E, 1310F, 1310G, 1310H, and 1310I feedback signals are rendered by the Biofeedback Discussion System e.g., 310. Seminar attendees will be notified by their vibrating wristband e.g., 1780 or vibrating smartphone e.g., 1770 if the seminar attendee's heart rate or breathing rate exceeds normal values or the hand temperature device e.g., 1650 shows that they are stressed to remind them to breathe deeply and maybe take a break from the discussion for a minute or two in order to calm down. If seminar attendees' brainwave helmets e.g., 1670 or the camera e.g., 1610 detect that seminar attendees show signs of losing concentration (are bored) during the discussion, the flashing light e.g., 1765 will be activated when appropriate (when a certain percentage of seminar attendees' biosignals show the same inattentive behavior). For those seminar participants using a VR/AR headset e.g., 1730 to see and hear the seminar discussion, they will be able to use their smartphone to alter the view in their headset to see a variety of visual displays available that may or may not fit in the view-field of the VR/AR headset all at one time. It is envisioned that the VR/AR headset when used as an augmented reality or AR view of the seminar, the seminar attendee using this device will see overlays of information about the speaker when looking at the speaker or see additional visual renderings layered upon another display device's visual rendering as for example when viewing a large wall screen display e.g., 1725. Seminar attendees 1310A, 1310B, 1310C, 1310D, 1310E, 1310F, 1310G, 1310H, and 1310I are likely to respond to these feedback signals as they are rendered and possibly alter their discussion.

Feedback signals are rendered visually to the seminar attendees 1310A, 1310B, 1310C, 1310D, 1310E, 1310F, 1310G, 1310H, and 1310I and seminar speaker 1310S by the Biofeedback Discussion System e.g. 130. The seminar speaker would likely see these feedback signals rendered via a display monitor e.g., 1720 or a large wall screen display e.g. 1725. The seminar attendees would see these feedback signals rendered via a tablet e.g., 1710, a smartphone e.g., 1715, a display monitor e.g., 1720, or a large wall screen display e.g. 1725, a VR/AR headset e.g., 1730. In this example, a view of the visual display 1305 shows example feedback signal renderings that include a Topic List+1 1320, a progress indicator for the percentage of agenda items covered 1330, a progress indicator for the elapsed time of the discussion 1340, a word hat 1350, a seminar system software agent avatar 1360, and the avatar's speech bubble 1365.

The Topic List+1 1320 is generated by the Biofeedback Discussion System e.g., 130 based on the agenda that was submitted to the Biofeedback Discussion System prior to the seminar. The Discussion Altering Machine e.g., 320 prepares the seminar agenda items by tokenizing (breaking down the sentences or phrases of the topic list) the agenda list items and forwards this tokenized grouping to the AI System e.g., 360 for categorization. The AI System, using appropriate taxonomy and ontology relationships returns a list of categories that cover the initially tokenized agenda list and expands this query for related categories by one (1) degree. An expansion of one (1) degree includes the node in the taxonomy or ontology that is one edge (one relationship) removed from the initial categorization entity. The expansion of agenda terminology to topic+1 in a seminar setting will enable the seminar participants 1310A, 1310B, 1310C, 1310D, 1310E, 1310F, 1310G, 1310H, and 1310I and seminar speaker 1310S to broaden their discussion beyond what was originally conceived when composing the agenda and will likely lead to unexpected approaches to the discussion; thus altering that discussion.

A sliding-scale measure 1330 of the percentage of agenda items that have been discussed as a portion of all of the scheduled agenda items for the discussion. Prior to starting the seminar discussion, the seminar speaker 1310S or a seminar organizer will have submitted an agenda for the seminar to the Biofeedback Discussion System e.g., 130. The black portion of the agenda items covered box, signifies the portion of agenda items discussed as a percentage of the all the agenda items that were scheduled for the discussion. The agenda items covered is rendered and is provided as a tool to help the seminar attendees 1310A, 1310B, 1310C, 1310D, 1310E, 1310F, 1310G, 1310H, and 1310I and the seminar speaker 1310S manage the time that they have allocated and to ensure that each agenda item 1330 has been covered and that each seminar attendee has had their question answered or at least acknowledged and added to the seminar transcript as open items that require further discussion before the seminar ends. Seeing the how much of the total agenda items have been covered may prompt the seminar speaker 1310S to move to the next agenda item or answer a question quickly; thus altering the discussion.

A sliding-scale measure 1340 represents the time that has elapsed during the discussion. Time allotted for the seminar has been predetermined by the seminar speaker or the organization managing the seminar. The black portion of the elapsed time box, signifies the portion of the total time set aside for the discussion that has already elapsed. The portion of time is measured as a percentage of the whole time allocated for the discussion. The time elapsed rendering is provided as a tool to help the seminar speaker 1310S manage the time that they have allocated in order to best achieve their seminar discussion goals. When the elapsed time measurement approaches 90% completion, the Biofeedback Discussion System will notify or remind the seminar participants (by way of the seminar system software agent speech bubble 1365) that the discussion time is nearing completion. When the elapsed time measurement approaches 95% completion, the Biofeedback Discussion System will suggest to the seminar participants (by way of the seminar system software agent speech bubble 1365) that they need to wrap up the seminar and assess which agenda items have been discussed and achieved during the discussion and what agenda items, if any, have yet to be addressed or completed.

A word hat graph 1350 renders the most used words spoken and written by seminar participants during the discussion. The word hat graph renders the most used discussion words in a list that is overlaid upon a visual image of an upturned hat as might be used in a magic show. The most used words are listed in order from top to bottom vertically from most used to lesser used words that are shown coming out of the hat and included in the list. Each time the word list is updated by the Biofeedback Discussion System e.g., 130. The words emerge from the hat image scrolling upwards as if they were coming out of the hat. The list of commonly used words does not include adjectives, preposition, and other words including but not limited to in this non-exhaustive list: good, new, first, last, long, great, little, own, other, old, right, big, high, different, small, large, next, early, young, important, few, public, bad, same, able, to, of, in, for, on, with, at, by, from, up, about, into, over, after, beneath, under, above, the, and, a, that, I, it, not, he, as, you, this, but, his, they, her, she, or, an, will, my, one, all, would, there, their. The seminar participants seeing the rendering of most used words are kept aware of the content of their seminar discussion and can easily determine whether the group of most used words cover the sub-goal topics that are set as a goal to be covered during the discussion. This method of rendering most used words to the participants 1310A, 1310B, 1310C, 1310D, 1310E, 1310F, 1310G, 1310H, 1310I, and 1310S may appear surprising and compelling such that the changing order of emerging words from the hat or seeing new words emerge from the had may have the effect of altering the discussion.

The seminar system software agent 1360 is the system interface between the seminar attendees 1310A, 1310B, 1310C, 1310D, 1310E, 1310F, 1310G, 1310H, and 1310I, the seminar speaker 1310S, and the Biofeedback Discussion System e.g., 130. The seminar system Software Agent Behavior e.g., 315 embodied by the seminar system software agent avatar 1360 and is driven by the Discussion Altering Machine e.g., 320. Focusing back on FIG. 12, the system has rendered a visual representation of the seminar system software agent as a businessman avatar. The seminar system software agent participates in a discussion with the seminar attendees (any one or a combination of the seminar attendees) and the speaker 1310S to provide feedback signals in the form of responses to seminar participant feedback signals 1320, 1330, 1340, and 1350 and to respond to seminar attendee or speaker questions asked of the Biofeedback Discussion System should they occur.

A speech bubble 1365 is used by the seminar system software agent 1360 to carry on the discussion with the seminar participants 1310A, 1310B, 1310C, 1310D, 1310E, 1310F, 1310G, 1310H, 1310I (any one of the seminar participants) and the speaker 1310S. Answers to any questions answered by the seminar system software agent 1360 during the discussion will be rendered as text in the speech bubble unless the system software avatar is enabled to respond to the question aurally. Although it is anticipated that the seminar system software agent 1360 will have the capability of aural speech, this embodiment implies both the additional aural speech discussion capability as well as the textual discussion capability via the example of the feedback signal rendered as visual text.

Figure 14:
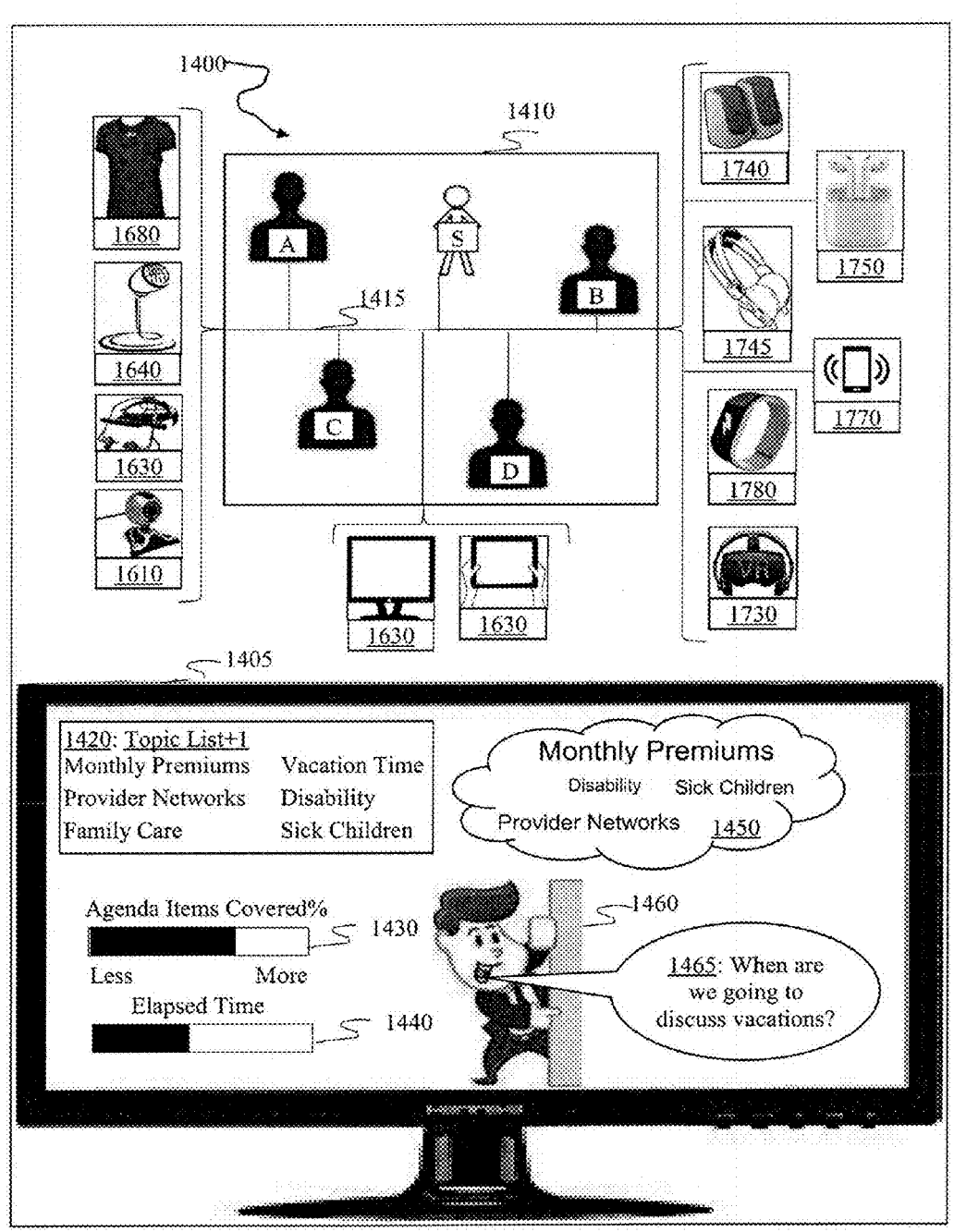
FIG. 14 is a diagram of webinar participants during a discussion. The diagram depicts an example of an employment webinar where participants are not located together. The Discussion Altering Machine provides aural, visual, and tactile feedback signals that enable them to more clearly understand the importance of particular issues and through this awareness, engage in the discussion so that their webinar goals are met.

FIG. 14 is a diagram of a webinar attended by a group of people. Devices capture their visually perceptible and sound output biosignals as well as eye behavior and heart and breathing rates e.g., with a camera 1610, an eye-tracking headset 1630, a microphone 1640, and a T-shirt containing sensors 1680 respectively. Feedback devices render visual, aural, and tactile feedback signals to the webinar participants 1410A, 1410B, 1410C, 1410D and 1410S. Communication link 1415 connects webinar participants 1410A, 1410B, 1410C, 1410D and 1410S to each other, to biofeedback devices, and to the Biofeedback Discussion System e.g., 130 (this connection is not explicitly shown in this example). These feedback signals are rendered e.g., to a tablet 1710, a display monitor 1720, Virtual Reality (VR)/Augmented Reality (AR) headset 1730, speakers 1740, headphones 1745, AirPods™ 1750, a vibrating smartphone 1770, and a vibrating/shock emitting wristband 1780. The visual display 1405 includes a Topic List+1 1420, a progress indicator for the percentage of agenda items covered 1430, a progress indicator for the elapsed time of the discussion 1440, a tag cloud 1450, a seminar system software agent avatar 1460, and the avatar's speech bubble 1465.

To be useful as biofeedback, biofeedback signals rendered via devices e.g., 1710, 1720, 1730, 1740, 1745, 1750, 1770, and 1780 are presented to the seminar participants 1410A, 1410B, 1410C, 1410D and 1410S in substantially near real-time, and preferably in near real-time.

The nature of the webinar in this example is one among company employees within a business environment. Although this example is about business webinars, other groups participating in webinars may include but not be limited to social organizations, charitable organizations, religious organizations, special interest organizations are also considered as likely embodiments for webinar biofeedback altering their discussion.

Webinars and seminars could be considered as fairly similar types of business or other domain group meetings. In examples 1400 and 1300 the differences between webinars and seminars exist in that webinars participants are always distributed (across locations) and discussions would operate differently as to which biofeedback signals and are effective and under what circumstances; whereas seminars participants are most always co-located, can see each other and the speaker, and would therefore more effectively react to different biofeedback signals than would be effective for webinar participants.

The webinar participants include a webinar speaker 1410S and a group of webinar attendees 1410A, 1410B, 1410C, and 1410D. Although a specific number of webinar attendees are shown in this example, it is anticipated that there may be any number of webinar attendees 1410A, 1410B, 1410C . . . 1410N. The 1410S attendee is the special case of the speaker. Herein the webinar participants are referred to as a webinar speaker and webinar attendees respectively and as a group they are webinar participants.

The webinar participants may each have a webinar goal that they want to achieve during the discussion with the Biofeedback Discussion System e.g., 130 and with other webinar participants. Often in a business webinar the agenda has been set by one or a handful of webinar leaders and the webinar goal may or may not be clear to all webinar participants and then may only be stated at the end as webinar outcomes (implying the goal for the webinar). When using the Biofeedback Discussion System, the goal of the webinar speaker 1410S is to cover all agenda items within the time allotted 1440 for the webinar and to answer webinar attendee questions. Whereas the goal of each webinar attendee 1410A, 1410B, 1410C, and 1410D when using the Biofeedback Discussion System, is to ensure that their particular interest is included within at least one of the items of the agenda list and is discussed during the webinar to the satisfaction of that webinar attendee.

Usefulness of biofeedback signals to webinar attendees 1410A, 1410B, 1410C, and 1410D and webinar speaker 1410S is very likely related to the amount, quality and relevance of information provided to the system. For example, for webinar participants, discussions are mostly centered on the webinar agenda and possibly the speaker's 1410S background and career artifacts. Some preferred embodiments will automatically load the speaker's data (e.g., as part of initialization data 310) and populate the rendered feedback signals accordingly; incorporating this data for the start of the current discussion.

The webinar speaker 1410S is a special case webinar participant. The webinar speaker has either compiled the agenda items alone or together with the webinar sponsor or organizer. The webinar speaker leads the discussion by presenting the agenda items and the detailed content information pertaining to the agenda list to the webinar attendees 1410A, 1410B, 1410C, and 1410D. In this example, where webinar attendees and the webinar speaker are not co-located, webinar attendees cannot see the webinar speaker and all the webinar attendees in human form during the discussion.

Webinar speaker 1410S provides many different types of information to the system. One type is particular to webinars for example as in an agenda and possibly the speaker's background information and career artifacts. Another type of information is sensor derived information from a heart and breathing rate T-shirt e.g., 1680, an eye-tracking headset e.g., 1630, and a standard microphone e.g., 1640, and camera e.g., 1610 all to capture their biosignals. Feedback signal are rendered to the webinar speaker 1410S via either of e.g., to a tablet 1710 or a display monitor 1720. Other feedback signals are rendered to the webinar speaker 1410S via e.g., speakers 1740, a vibrating smartphone 1770, and/or a vibrating/shock emitting wristband 1780.

Webinar attendees 1410A, 1410B, 1410C, and 1410D provide many different types of information to the system. One type is particular to webinars; for example, questions based on the agenda and the discussion. Another type of information is sensor derived information from a heart and breathing rate T-shirt e.g., 1680, an eye-tracking headset e.g., 1630, and a standard microphone e.g., 1640, and camera e.g., 1610 all to capture their biosignals. Feedback signals are rendered to the webinar attendees 1410A, 1410B, 1410C, and 1410D via either of e.g., a tablet 1710 or a display monitor 1720. Other feedback signals are rendered to the webinar attendees 1410A, 1410B, 1410C, and 1410D via e.g., a Virtual Reality (VR/Augmented Reality (AR) headset 1730, speakers 1740, headphones 1745, AirPods™ 1750, a vibrating smartphone 1770, a vibrating/shock emitting wristband 1780. The webinar attendees are assumed to use a varying combination of sensors and feedback rendering devices herein identified for use during the discussion.

The webinar speaker 1410S wants to ensure that all agenda items are covered to the satisfaction of webinar attendees 1410A, 1410B, 1410C, and 1410D as well as allocating sufficient time to answer webinar attendee questions. The webinar speaker also wants to remain aware of their own behavior during the discussion.

Webinar attendees 1410A, 1410B, 1410C, and 1410D want to ensure that the webinar agenda items are discussed and that their questions are answered during the time allotted for the webinar. The motivation for webinar attendees using the Biofeedback Discussion System can be to keep track of percentage of agenda items covered during the allotted webinar time, to see an expanded topic view, to watch which topic words are dominating the discussion, and to remain aware of the list of webinar attendee questions to make sure their question appears on the list and that the speaker 1410S is using time wisely so that their question will be answered during the discussion.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Webinar speaker 1410S emits biosignals while engaged in the webinar discussion. Biofeedback signals for heart rate, breathing rate, voice anger, content anger, eye movement, and pupil dilation are categorized. Measurement of heart rate and breathing rate biosignals are obtained whereby the webinar speaker 1210S wears clothing containing sensors, e.g., a T-shirt 1680. The webinar speaker's voice anger and content anger (anger words) is obtained by a microphone, e.g., 1640. The webinar speaker's eye movement and pupil dilation biosignal is obtained by a camera, e.g., 1610. The webinar speaker's fidgeting and gesture biosignals are obtained by that webinar speaker's actions being observed by a camera, e.g. 1610.

Webinar attendees 1410A, 1410B, 1410C, and 1410D emit biosignals while engaged in the webinar discussion. Biofeedback signals for heart rate, breathing rate, and fidgeting and gestures (both general body and hand and limb movement) are categorized. Measurement of heart rate and breathing rate biosignals are obtained whereby the webinar attendees 1410A, 1410B, 1410C, and 1410D wear clothing containing sensors, e.g., a T-shirt 1680. The webinar attendees' fidgeting and gesture biosignals are obtained by that webinar attendee's actions being observed by a camera, e.g. 1610.

Webinar speaker's 1410S feedback signals are rendered by the Biofeedback Discussion System e.g., 310. The webinar speaker's wristband e.g., 1780 will vibrate if the webinar speaker's heart rate or breathing rate exceeds normal values showing that they are stressed; reminding them to breathe deeply in order to calm down. The webinar speaker's wristband will emit a mild shock if the microphone detects that the speaker is talking too loudly (out of normal talking range as in shouting). A foghorn will sound from e.g., VR/AR headset earphones 1730, speakers 1740, headphones 1745, and AirPods™ 1750 for all participants if the webinar speaker is using content anger (anger words) or negative gestures or facial expressions. A harsh sound would be emitted from e.g., VR/AR headset earphones 1730, speakers 1740, headphones 1745, and AirPods™ 1750 if it was determined that the webinar speaker's 1410S eye movements indicated that they are lying (it has been shown that looking up and to the left may signify lying). A series of short beeps is sounded to e.g., VR/AR headset earphones 1730, speakers 1740, headphones 1745, and AirPods™ 1750 for all participants if the speaker has been talking too long on one topic based on the remaining webinar time and remaining topics and questions to be answered. The webinar system software agent 1460 will notify the webinar speaker (either verbally or in the avatar's speech bubble 1465) if the webinar timing is insufficient to cover all agenda items and webinar participant questions.

Webinar attendees 1410A, 1410B, 1410C, and 1410D feedback signals are rendered by the Biofeedback Discussion System e.g., 310. Webinar attendees will be notified by their vibrating wristband e.g., 1780 or vibrating smartphone e.g., 1770 if a webinar attendee's heart rate or breathing rate exceeds normal values that shows that they are stressed in order to remind them to breathe deeply and maybe take a break from the discussion for a minute or two in order to calm down. If webinar attendees' eye-tracking headset e.g., 1630 or a camera e.g., 1610 detect that webinar attendees show signs of losing concentration (are bored) during the discussion, their wristband e.g., 1780 will emit a mild shock to that participant. When a certain percentage of webinar attendees' biosignals show the same inattentive behavior detected by their eye-tracking headset e.g., 1630 or a camera e.g., 1610, an ominous set of musical chords (as in doom and gloom) will sound from e.g., VR/AR headset speakers 1730, speakers 1740, headphones 1745, and AirPods™ 1750 for the webinar attendees and webinar speaker. For those webinar participants using a VR/AR headset e.g., 1730 to see and hear the webinar discussion, they will be able to use their smartphone to alter the view in their headset to see a variety of visual displays available that may or may not fit in the view-field of the VR/AR headset all at one time. It is envisioned that the VR/AR headset when used as an augmented reality or AR view of the webinar, the webinar attendee using this device could see overlays of information about the speaker superimposed on an image of the speaker that comes from the webinar speaker's 1410S camera e.g., 1610 or see additional visual renderings layered another visual rendering. Webinar attendees 1410A, 1410B, 1410C, and 1410D are likely to respond to these feedback signals as they are rendered and possibly alter their discussion.

The communication link 1415 between the webinar participants 1410A, 1410B, 1410C, 1410D, and 1410S, biofeedback devices, and the Biofeedback Discussion System e.g., 130. The communication link 1415 enables webinar participants to communicate with each other, with biofeedback input and output devices, and the Biofeedback Discussion System. Communication link 1415 can operate over any remote digital connection protocol including as examples, but are not limited to, the Internet, WiFi, Bluetooth, near-field, or telecommunications bands.

Feedback signals are rendered visually to the webinar attendees 1410A, 1410B, 1410C, and 1410D and webinar speaker 1410S by the Biofeedback Discussion System e.g. 130. The webinar speaker would likely see these feedback signals rendered via a display monitor e.g., 1720 or a tablet e.g., 1715. The webinar attendees would see these feedback signals rendered via a tablet e.g., 1710, a display monitor, or a VR/AR headset e.g., 1730. In this example, a view of the visual display 1405 shows example feedback signal renderings that include a Topic List+1 1420, a progress indicator for the percentage of agenda items covered 1430, a progress indicator for the elapsed time of the discussion 1440, a tag cloud 1450, a seminar system software agent avatar 1460, and the avatar's speech bubble 1465.

The Topic List+1 1420 is generated by the Biofeedback Discussion System e.g., 130 based on the agenda that was submitted to the Biofeedback Discussion System prior to the webinar. The Discussion Altering Machine e.g., 320 prepares the webinar agenda items by tokenizing (breaking down the sentences or phrases of the topic list) the agenda list items and forwards this tokenized grouping to the AI System e.g., 360 for categorization. The AI System, using appropriate taxonomy and ontology relationships returns a list of categories that cover the initially tokenized agenda list and expands this query for related categories by one (1) degree. An expansion of one (1) degree includes the node in the taxonomy or ontology that is one edge (one relationship) removed from the initial categorization entity. The expansion of agenda terminology to topic+1 in a webinar setting will enable the webinar attendees 1410A, 1410B, 1410C, and 1410D and webinar speaker 1410S to broaden their discussion beyond what was originally conceived when composing the agenda and will likely lead to unexpected approaches to discussion thus altering that discussion.

A sliding-scale measure 1430 of the percentage of agenda items that have been discussed as a portion of all of the agenda items discussed during the discussion. Prior to starting the webinar discussion, the webinar speaker 1410S or webinar organizer will have submitted an agenda for the webinar to the Biofeedback Discussion System e.g., 130. The black portion of the agenda items covered box, signifies the portion as a percentage of the all the agenda items that have been discussed during the discussion. The agenda items covered is rendered and is provided as a tool to help the webinar attendees 1410A, 1410B, 1410C, and 1410D and webinar speaker 1410S manage the time that they have allocated and to ensure that each agenda item has been covered and that each webinar attendee has had their questions answered or at least acknowledged and added to the webinar transcript as open items that require further discussion before the webinar ends. Seeing the how much of the total agenda items have been covered may prompt the seminar speaker 1410S to move to the next agenda item or answer a question quickly; thus altering the discussion.

A sliding-scale measure 1340 represents the time that has elapsed during the discussion. Time allotted for the webinar has been predetermined by the webinar speaker or the organization managing the webinar. The black portion of the elapsed time box, signifies the portion of the total time set aside for the discussion that has already elapsed. The portion of time is measured as a percentage of the whole time allocated for the discussion. The time elapsed rendering is provided as a tool to help the webinar speaker 1410S manage the time that they have allocated in order to best achieve their webinar discussion goals. When the elapsed time measurement approaches 90% completion, the Biofeedback Discussion System will notify or remind the webinar participants (by way of the webinar system software agent speech bubble 1465) that the discussion time is nearing completion. When the elapsed time measurement approaches 95% completion, the Biofeedback Discussion System will suggest to the webinar participants (by way of the webinar system software agent speech bubble 1465) that they need to wrap up the webinar and assess which agenda items have been discussed and achieved during the discussion and what agenda items, if any, have yet to be addressed or completed.

A tag cloud graph 1450 renders the most used words spoken and written by webinar participants 1410A, 1410B, 1410C, 1410D, and 1410S during the discussion. The tag cloud graphic renders the most used words in the most prominent manner either by using a larger font size than other words of lesser importance to render the words, by using brighter colors for the most often used words, or by some other means of visual significance within the graphical rendering space that signifies that a particular word is more significant or important or at least more often used during the discussion than other words. The list of commonly used words does not include adjectives, preposition, and other words as examples in this non-exhaustive list: good, new, first, last, long, great, little, own, other, old, right, big, high, different, small, large, next, early, young, important, few, public, bad, same, able, to, of, in, for, on, with, at, by, from, up, about, into, over, after, beneath, under, above, the, and, a, that, I, it, not, he, as, you, this, but, his, they, her, she, or, an, will, my, one, all, would, there, their. The webinar participants seeing the rendering of most used words are kept aware of the content of their webinar discussion and can easily determine whether the group of most used words cover the sub-goal topics that are set as a goal to be covered during the discussion. A webinar participant noticing the elapsed time reading 1440, the agenda items covered 1430, and the tag cloud 1450 can see that although the topic of Sick Children has at least been mentioned, the discussion has not given sufficient attention to satisfy questions coming from concerned parents. That individual webinar participant 1410A will then alter the discussion by bringing this information to the attention of the other webinar participants 1410A, 1410B, 1410C, 1410D (any one of the webinar attendees) and the webinar speaker 1410S and then alter the discussion.

A webinar system software agent 1460 is the system interface between the webinar attendees 1410A, 1410B, 1410C, 1410D the webinar speaker 1310S, and the Biofeedback Discussion System e.g., 130. The webinar system Software Agent Behavior e.g., 315 is driven by the Discussion Altering Machine e.g., 320. Focusing back on FIG. 14, the system has rendered a visual representation of the webinar system software agent as a businessman avatar. The webinar system software agent participates in a discussion with the webinar attendees 1410A, 1410B, 1410C, 1410D (any one or a combination of the webinar attendees) and the speaker 1410S to provide feedback signals in the form of responses to webinar participant feedback signals 1420, 1430, 1440, and 1450 and to respond to webinar participant questions asked of the Biofeedback Discussion System should they occur.

A speech bubble 1465 is used by the webinar system software agent 1460 to carry on the discussion with the webinar participants 1410A, 1410B, 1410C, 1410D (any one of the webinar attendees) and the speaker 1410S. Answers to any questions answered by the webinar system software agent 1460 during the discussion will be rendered as text in the speech bubble unless the system software avatar is enabled to respond to the question aurally. Although it is anticipated that the webinar system software agent 1460 will have the capability of aural speech, this embodiment implies both the additional aural speech discussion capability as well as the textual discussion capability via the example of the feedback signal rendered as visual text.

Figure 15:
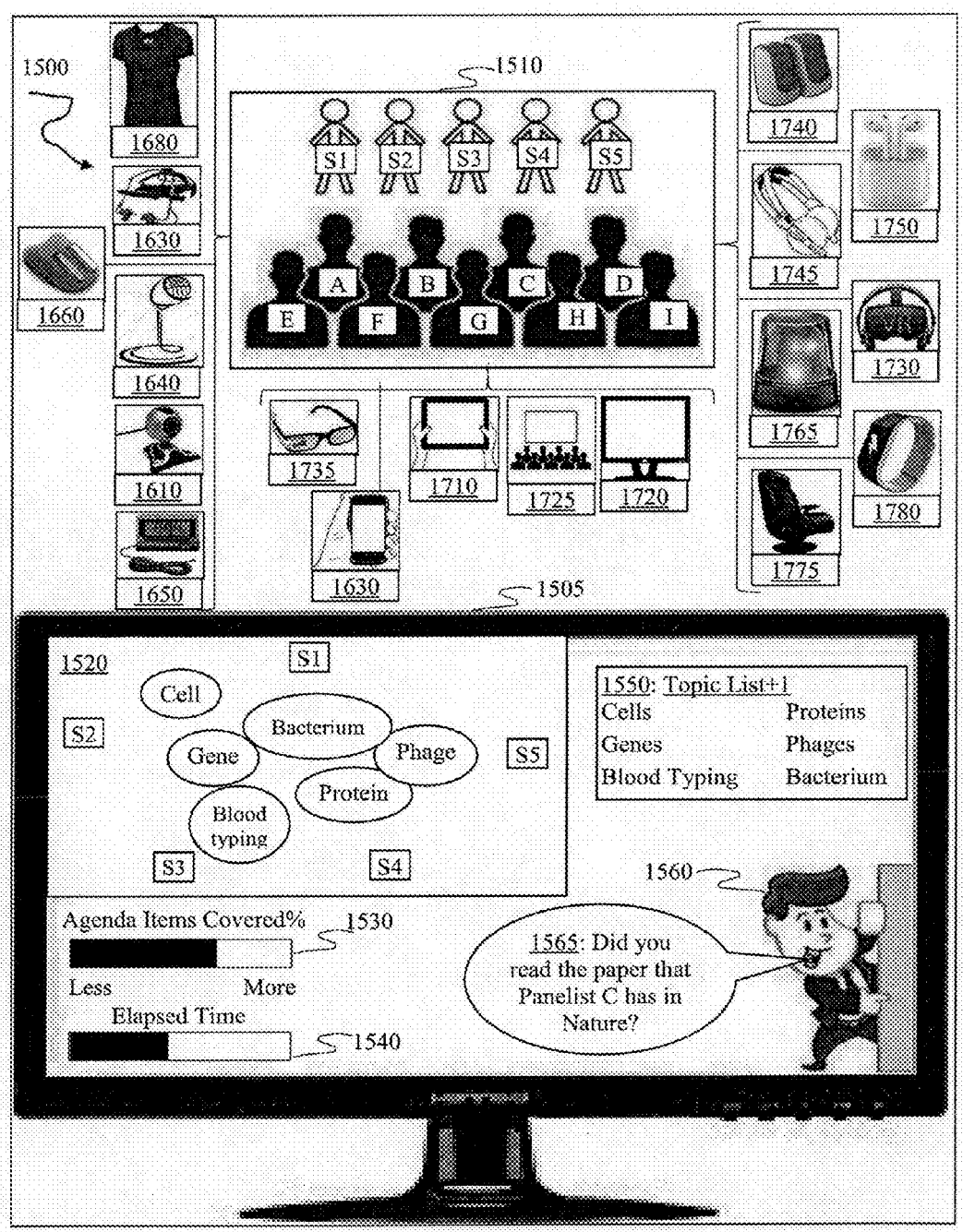
FIG. 15 is a diagram of a round-table event hosting five speakers and attended by many participants. The diagram depicts an example of a round-table technical review discussion in the realm of biophysics. The Biofeedback Discussion System renders auditory, visual and tactile feedback signals to the speakers and participants so that they can coordinate the interest of the participants with the information from the speakers more accurately in substantially near real-time.

FIG. 15 is a diagram of a round-table event attended by a group of people. Devices capture their visually perceptible and sound output biosignals as well as eye behavior, hand temperature, and heart and breathing rates e.g., with a camera 1610, a microphone 1640, an eye-tracking headset 1630, a hand temperature sensor 1650, a galvanic skin response (GSR) stress detection device 1660, and a T-shirt containing sensors 1680 respectively. Feedback devices render visual, aural, and tactile feedback signals to the round-table event participants 1510A, 1510B, 1510C, 1510D, 1510E, 1510F, 1510G, 1510H, 1510I, 1510S1, 1510S2, 1510S3, 1510S4, and 1510S5. These feedback signals are rendered e.g., to a tablet 1710, a smartphone 1715, a display monitor 1720, a large wall screen display 1725, Virtual Reality (VR)/Augmented Reality (AR) headset 1730, Google™ Glass™ 1735, speakers 1740, headphones 1745, AirPods™ 1750, a flashing light 1765, a vibrating chair 1775, and a vibrating/shock emitting wristband 1780. The visual display 1505 includes an affinity graph 1520, a progress indicator for the percentage of agenda items covered 1530, a progress indicator for the elapsed time of the discussion 1540, a Topic List+1 1550, a seminar system software agent avatar 1560, and the avatar's speech bubble 1565.

To be useful as biofeedback, biofeedback signals rendered via devices e.g., 1710, 1715, 1720, 1725, 1730, 1735, 1740, 1745, 1750, 1765, 1775, and 1780 are presented to the seminar participants 1510A, 1510B, 1510C, 1510D, 1510E, 1510F, 1510G, 1510H, 1510I, 1510S1, 1510S2, 1510S3, 1510S4, and 1510S5 in substantially near real-time, and preferably in near real-time.

The nature of the round-table event in this example is one among company employees within a business environment. Although this example is about business round-table events, other groups attending round-table events for example include social organizations, charitable organizations, religious organizations, special interest organizations are also considered as likely embodiments for round-table event biofeedback altering their discussion.

The round-table event participants include round-table event speakers 1510S1, 1510S2, 1510S3, 1510S4, and 1510S5 and a group of round-table event attendees 1510A, 1510B, 1510C, 1510D, 1510E, 1510F, 1510G, 1510H, and 1510I. Although a specific number of round-table event speakers and attendees are shown in this example, it is anticipated that there may be any number of round-table event speakers 1510S1, 1510S2, 1510S3 . . . 1510SN and attendees 1510A, 1510B, 1510C . . . 1510N. The 1510S1, 1510S2, 1510S3, 1510S4, and 1510S5 attendee is the special case of the speakers. Herein the round-table event participants are referred to as a round-table event speaker(s) and round-table event attendees respectively and as a group they are round-table event participants.

The round-table event participants may each have a round-table event goal that they want to achieve during the discussion with the Biofeedback Discussion System e.g., 130 and with other round-table event speakers and participants. Often in a business round-table event the agenda has been set by one or a handful of round-table event leaders and the round-table event goal may or may not be clear to all round-table event participants and then may only be stated at the end as round-table event outcomes (implying the goal for the round-table event). When using the Biofeedback Discussion System, the goal of the round-table event speakers 1510A, 1510B, 1510C, 1510D, and 1510E is to cover all agenda items within the time allotted 1540 for the round-table event and to answer round-table event participant questions. Whereas the goal of each round-table event participant 1510A, 1510B, 1510C, 1510D, 1510E, 1510F, 1510G, 1510H, and 1510I when using the Biofeedback Discussion System, is to ensure that their particular interest is included within at least one of the items of the agenda list and is discussed during the round-table event to the satisfaction of that round-table event participant.

Usefulness of biofeedback signals to round-table event attendees 1510A, 1510B, 1510C, 1510D, 1510E, 1510F, 1510G, 1510H, and 1510I and round-table event speakers 1510S1, 1510S2, 1510S3, 1510S4, and 1510S5 is very likely related to the amount, quality and relevance of information provided to the system. For example, for round-table event participants, discussions are mostly centered on the round-table event agenda and the speakers' 1510S1, 1510S2, 1510S3, 1510S4, and 1510S5 background and career artifacts. Some preferred embodiments will automatically load the speakers' data (e.g., as part of initialization data 310) and populate the rendered feedback signals accordingly; incorporating this data for the start of the current discussion.

The round-table event speakers 1510S1, 1510S2, 1510S3, 1510S4, and 1510S5 are a special case round-table event participant. A round-table event speaker has either compiled the agenda items alone, together with the other round-table event speakers, or together with round-table event sponsors or organizers. Round-table event speakers lead the discussion by presenting their agenda items and the detailed content information pertaining to their agenda list to the round-table event attendees 1510A, 1510B, 1510C, 1510D, 1510E, 1510F, 1510G, 1510H, and 1510I. In this example, round-table event attendees can see the round-table event speakers and all the round-table event attendees in human form at the round-table event during the discussion; although in other round-table event embodiment examples one or more round-table event speakers and one or more round-table event attendees can participate in the round-table event from a remote location.

Round-table event speaker 1510S1, 1510S2, 1510S3, 1510S4, and 1510S5 provides many different types of information to the system. One type is particular to round-table events including but not limited to an agenda, their background information, and career artifacts. Another type of information is sensor derived information from a heart and breathing rate T-shirt e.g., 1680, an eye-tracking headset e.g., 1630, a galvanic skin response (GSR) stress detection device e.g., 1660, and a standard microphone e.g., 1640, and camera e.g., 1610 all to capture their biosignals. Feedback signal are rendered to the round-table event speakers 1510S1, 1510S2, 1510S3, 1510S4, and 1510S5 via any of e.g., to a tablet 1710, a smartphone 1715, a display monitor 1720, a large wall screen display 1725, or Google™ Glass™ 1735. Other feedback signals are rendered to the conference speakers 1510S1, 1510S2, 1510S3, 1510S4, and 1510S5 via e.g., speakers 1740, a flashing light 1765, a vibrating chair 1775, and/or a vibrating/shock emitting wristband 1780.

Round-table event attendees 1510A, 1510B, 1510C, 1510D, 1510E, 1510F, 1510G, 1510H, and 1510I provide many different types of information to the system. One type is particular to round-table event for example questions based on the agenda and the discussion. Another type of information is sensor derived information from a heart and breathing rate T-shirt e.g., 1680, a hand temperature sensor e.g., 1650, and a standard microphone e.g., 1640, and camera e.g., 1610 all to capture their biosignals. Feedback signals are rendered to the round-table event attendees 1510A, 1510B, 1510C, 1510D, 1510E, 1510F, 1510G, 1510H, and 1510I via any of e.g., a tablet 1710, a smartphone 1715, a display monitor 1720, a large wall screen display 1725, or Google™ Glass™ 1735. Other feedback signals are rendered to the round-table event attendees 1510A, 1510B, 1510C, 1510D, 1510E, 1510F, 1510G, 1510H, and 1510I via e.g., a VR/AR headset 1730, speakers 1740, headphones 1745, AirPods™ 1750, a flashing light 1765, a vibrating smartphone 1770, a vibrating/shock emitting wristband 1780. The round-table event attendees are assumed to use a varying combination of sensors and feedback rendering devices herein identified for use during the discussion.

Round-table event speakers 1510S1, 1510S2, 1510S3, 1510S4, and 1510S5 want to ensure that all of their agenda items are covered to the satisfaction of round-table event attendees 1510A, 1510B, 1510C, 1510D, 1510E, 1510F, 1510G, 1510H, and 1510I as well as allocating sufficient time to answer round-table event attendee questions. A round-table event speaker also wants to remain aware of their own behavior during the discussion.

Round-table event attendees 1510A, 1510B, 1510C, 1510D, 1510E, 1510F, 1510G, 1510H, and 1510I want to ensure that the round-table event agenda items are discussed and that their questions are answered during the time allotted for the round-table event. The motivation for round-table event attendees using the Biofeedback Discussion System can be to keep track of percentage of agenda items covered during the allotted round-table event time, to see which speakers most use which specific words during the discussion, to see an expanded topic view, to and to remain aware of the list of round-table event attendee questions to make sure their question appears on the list and that the speakers 1510S1, 1510S2, 1510S3, 1510S4, and 1510S5 are using time wisely so that their question will be answered during the discussion.

Biofeedback signals rendered to participants can range from the very simple (buzzes, flashes, vibrations, etc.) to more complicated auditory and visual tactile signals, for example photographs, diagrams, and videos. It is even contemplated that feedback signals could include complex tactile and olfactory stimuli. The biofeedback signals can be rendered to participants in any suitable manner, as for example using a display screen for flashes, images or videos, and using a speaker for beeps or other auditory signals.

Round-table event speakers 1510S1, 1510S2, 1510S3, 1510S4, and 1510S5 emit biosignals while engaged in the round-table event discussion. Biofeedback signals for heart rate, breathing rate, voice anger, content anger, eye movement, pupil dilation, hand temperature, and fidgeting and gestures (both general body and hand and limb movement) are categorized. Measurement of heart rate and breathing rate biosignals are obtained whereby round-table event speakers 1510S1, 1510S2, 1510S3, 1510S4, and 1510S5 wear clothing containing sensors, e.g., a T-shirt 1680. The round-table event speakers' voice anger and content anger is obtained by a microphone, e.g., 1640. The round-table event speakers' eye movement and pupil dilation biosignal is obtained by the round-table event speaker wearing an eye-tracking headset, e.g., 1630. It has been shown a round-table speaker's concentration level can be discerned by the amount of pupil dilation observed for that round-table speaker and that detection of possible lying by a round-table speakers can be observed by that speaker's eyes moving up and to the left. The round-table event speaker's hand temperature is obtained whereby the round-table event speakers' hand temperature and hand moisture are obtained whereby the round-table event speaker rests his/her fingers in the slots at the top of the GSR device, e.g., 1660. The round-table event speaker's fidgeting and gesture biosignals are obtained by that round-table event speaker's actions being observed by a camera, e.g. 1610.

Round-table event attendees 1510A, 1510B, 1510C, 1510D, 1510E, 1510F, 1510G, 1510H, and 1510I emit biosignals while engaged in the round-table event discussion. Biofeedback signals for heart rate, breathing rate, hand temperature, and fidgeting and gestures (both general body and hand and limb movement) are categorized. Measurement of heart rate and breathing rate biosignals are obtained whereby the round-table event attendees 1510A, 1510B, 1510C, 1510D, 1510E, 1510F, 1510G, 1510H, and 1510I wear clothing containing sensors, e.g., a T-shirt 1680. The round-table event attendees' hand temperature is obtained whereby the round-table event attendees affix a hand temperature sensor, e.g., 1650 to their fingers. The round-table event attendees' fidgeting and gesture biosignals are obtained by that round-table event attendee's actions being observed by a camera, e.g. 1610.

Round-table event speakers 1510S1, 1510S2, 1510S3, 1510S4, and 1510S5 feedback signals are rendered by the Biofeedback Discussion System e.g., 310. In this example, it is assumed that all round-table event speakers are all wearing vibrating/shock emitting wristbands and sitting on chairs that can vibrate and that the round-table event speakers remain seated in the vibrating chairs while speaking. A round-table event speaker's wristband e.g., 1780 will vibrate or their Google™ Glass™ e.g., 1735 will register a notification if the round-table event speaker's heart rate or breathing rate exceeds normal values or their GSR hand temperature and moisture device e.g., 1660 shows that they are stressed; reminding them to breathe deeply in order to calm down. All round-table event speakers' wristbands e.g., 1780 will emit a mild shock if the camera e.g., 1610 detects that round-table event attendees a sufficient number of round table event attendees show signs of losing concentration (are bored) during the discussion. A foghorn will be sounded from e.g., VR/AR headset earphones 1730, speakers 1740, headphones 1745, or AirPods™ 1750 if the microphone e.g., 1640 or camera e.g., 1610 detect that the speaker is talking too loudly (out of normal talking range as in shouting), is using content anger (words), or negative gestures or facial expressions. A harsh audio clanging tone is sounded to e.g., VR/AR headset earphones 1730, speakers 1740, headphones 1745, and AirPods™ 1750 for all participants if any speaker has been talking too long on one topic; this duration assessment is based on the remaining round-table event time and remaining topics and questions to be answered. A flashing light e.g., 1765 will activate if any round-table event speaker's eyes move up and to the left while they are speaking as this may signify that round-table event speaker is lying. The round-table event system software agent 1560 will notify round-table event speakers (either verbally or in the avatar's speech bubble 1565) if the round-table event timing is insufficient to cover all agenda items and round-table event participant questions.

Round-table event attendees 1510A, 1510B, 1510C, 1510D, 1510E, 1510F, 1510G, 1510H, and 1510I feedback signals are rendered by the Biofeedback Discussion System e.g., 310. Round-table event attendees will be notified by their vibrating wristband e.g., 1780 or vibrating smartphone e.g., 1770 if the round-table event attendee's heart rate or breathing rate exceeds normal values or the hand temperature device e.g., 1650 shows that they are stressed to remind them to breathe deeply and maybe take a break from the discussion for a minute or two in order to calm down. If the camera e.g., 1610 detect that round-table event attendees show signs of losing concentration (are bored) during the discussion, that round-table event attendee's wristband e.g., 1780 emits a mild shock. For those round-table event participants using a VR/AR headset e.g., 1730 to see and hear the round-table event discussion, they will be able to use their smartphone to alter the view in their headset to see a variety the of visual displays available that may or may not fit in the view-field of the VR/AR headset all at one time. It is envisioned that the VR/AR headset when used as an augmented reality or AR view of the round-table event, the round-table event attendee using this device will see overlays of information about the speaker when looking at the speaker or see additional visual renderings layered upon another display device's visual rendering as for example when viewing a large wall screen display e.g., 1725. Round-table event attendees may think of questions that they want to ask of round-table event speakers based on the visual feedback signals rendered to the affinity graph 1520, the topic+1 list 1550, or the round-table event system software agent avatar's speech bubble 1565. Round-table event attendees 1510A, 1510B, 1510C, 1510D, 1510E, 1510F, 1510G, 1510H, and 1510I are likely to respond to these feedback signals as they are rendered and possibly alter their discussion.

Feedback signals are rendered visually to the round-table event attendees 1510A, 1510B, 1510C, 1510D, 1510E, 1510F, 1510G, 1510H, and 1510I and round-table event speakers 1510S1, 1510S2, 1510S3, 1510S4, and 1510S5 by the Biofeedback Discussion System e.g. 130. Round-table event speakers would likely see these feedback signals rendered via a display monitor e.g., 1720 or a large wall screen display e.g. 1725. The round-table event attendees would see these feedback signals rendered via a tablet e.g., 1710, a smartphone e.g., 1715, a display monitor e.g., 1720, or a large wall screen display e.g. 1725, a VR/AR headset e.g., 1730. In this example, a view of the visual display 1505 shows example feedback signal renderings that include an affinity graph 1520, a progress indicator for the percentage of agenda items covered 1530, a progress indicator for the elapsed time of the discussion 1540, a Topic List+1 1550, a round-table event system software agent avatar 1560, and the avatar's speech bubble 1565.

An affinity graph 1520 is rendered and updated periodically (depending on the embodiment example this could be somewhere between every 5 seconds and every 30 seconds) by the Biofeedback Discussion System e.g., 130. The graph shows the five (5) speakers, 1510S1, 1510S2, 1510S3, 1510S4, and 1510S5 as symbols in boxes "S1", "S2", "S3", "S4", and "S5" respectively. These box symbols remain stationary within the graph throughout the discussion. The words in ellipses are words that have been most frequently used during the discussion so far. The list of frequently used words does not include adjectives, preposition, and other words including but not limited to in this non-exhaustive list: good, new, first, last, long, great, little, own, other, old, right, big, high, different, small, large, next, early, young, important, few, public, bad, same, able, to, of, in, for, on, with, at, by, from, up, about, into, over, after, beneath, under, above, the, and, a, that, I, it, not, he, as, you, this, but, his, they, her, she, or, an, will, my, one, all, would, there, their. The number of most often used words included in the graphical display may vary from a possible minimum of the top 5 words to a possible limit of the top 20 words depending on the space available the embodiment example visual rendering space. The most frequently used words in the graph move according to which of the five (5) speakers has used that particular word the most. In this embodiment example i.e., "cells" has been spoken about the same amount of times by speakers 1510S1 and 1510S2 and "phages" has been said most often by 1510S5 during the discussion. Round-table event attendees 1510A, 1510B, 1510C, 1510D, 1510E, 1510F, 1510G, 1510H, and 1510I will observe which of the speakers is most conversant or most contentious about a particular topic word and will likely ask or not ask questions of particular speakers based on this knowledge; therefore altering the subsequent discussion.

A sliding-scale measure 1530 of the percentage of agenda items that have been discussed as a portion of all of the scheduled agenda items for the discussion. Prior to starting the round-table event discussion, a round-table event speaker has either compiled the agenda items alone, together with the other round-table event speakers, or together with round-table event sponsors or organizers and will have submitted the agenda for the round-table event to the Biofeedback Discussion System e.g., 130. The black portion of the agenda items covered box, signifies the portion of agenda items discussed as a percentage of the all the agenda items that were scheduled for the discussion. The agenda items covered is rendered and is provided as a tool to help the seminar attendees 1510A, 1510B, 1510C, 1510D, 1510E, 1510F, 1510G, 1510H, and 1510I and the seminar speakers 1510S1, 1510S2, 1510S3, 1510S4, and 1510S5 manage the time that they have allocated to the round-table event and to ensure that each agenda item has been covered and that each round-table event attendee has had their question answered or at least acknowledged and added to the round-table event transcript as open items that require further discussion before the round-table event ends. Seeing the how much of the total agenda items have been covered may prompt one or more seminar speakers 1510S1, 1510S2, 1510S3, 1510S4, and 1510S5 to move to the next agenda item or answer a question quickly; thus altering the discussion.

A sliding-scale measure 1540 of the time that has elapsed during the discussion. Time allotted for the round-table event has been predetermined by the round-table event speaker or the organization managing the round-table event. The black portion of the elapsed time box, signifies the portion of the total time set aside for the discussion that has already elapsed. The portion of time is measured as a percentage of the whole time allocated for the discussion. The time elapsed rendering is provided as a tool to help the round-table event participants manage the time that they have allocated in order to best achieve their round-table event discussion goals. When the elapsed time measurement approaches 90% completion, the Biofeedback Discussion System will notify or remind the round-table event participants (by way of the round-table event system software agent speech bubble 1565) that the discussion time is nearing completion. When the elapsed time measurement approaches 95% completion, the Biofeedback Discussion System will suggest to the round-table event participants (by way of the round-table event system software agent speech bubble 1565) that they need to wrap up the round-table event and assess which agenda items have been discussed and achieved during the discussion and what agenda items, if any, have yet to be addressed or completed.

The Topic List+1 1550 is generated by the Biofeedback Discussion System e.g., 130 based on the agenda that was submitted to the Biofeedback Discussion System prior to the round-table event. The Discussion Altering Machine e.g., 320 prepares the round-table event agenda items by tokenizing (breaking down the sentences or phrases of the topic list) the agenda list items and forwards this tokenized grouping to the AI System e.g., 360 for categorization. The AI System, using appropriate taxonomy and ontology relationships returns a list of categories that cover the initially tokenized agenda list and expands this query for related categories by one (1) degree. An expansion of one (1) degree includes the node in the taxonomy or ontology that is one edge (one relationship) removed from the initial categorization entity. The expansion of agenda terminology to topic+1 in a round-table event setting will enable the round-table event attendees 1510A, 1510B, 1510C, 1510D, 1510E, 1510F, 1510G, 1510H, and 1510I and round-table event speakers 1510S1, 1510S2, 1510S3, 1510S4, and 1510S5 to broaden their discussion beyond what was originally conceived when composing the agenda and will likely lead to unexpected approaches to discussion thus altering that discussion.

The round-table event system software agent 1560 is the system interface between the seminar attendees 1510A, 1510B, 1510C, 1510D, 1510E, 1510F, 1510G, 1510H, and 1510I, the seminar speakers 1510S1, 1510S2, 1510S3, 1510S4, and 1510S5, and the Biofeedback Discussion System e.g., 130. The round-table event system Software Agent Behavior e.g., 315 is driven by the Discussion Altering Machine e.g., 320. Focusing back on FIG. 15, the system has rendered a visual representation of the round-table event system software agent as a businessman avatar. The round-table event system software agent 1560 participates in a discussion with the round-table event attendees 1510A, 1510B, 1510C, 1510D, 1510E, 1510F, 1510G, 1510H, and 1510I (any one or a combination of the round-table event attendees) and the speakers 1510S1, 1510S2, 1510S3, 1510S4, and 1510S5 (any one or a combination of round-table event speakers) to provide feedback signals in the form of responses to round-table event attendee feedback signals 1520, 1530, 1540, and 1550 and to respond to round-table event attendee or speaker questions asked of the Biofeedback Discussion System should they occur.

A speech bubble 1565 is used by the round-table event system software agent 1560 to carry on the discussion with the round-table event participants 1510A, 1510B, 1510C, 1510D, 1510E, 1510F, 1510G, 1510H, and 1510I (any one or a combination of the round-table event participants) and all speakers 1510S1, 1510S2, 1510S3, 1510S4, and 1510S5 (any one or a combination of round-table event speakers). Answers to any questions answered by the round-table event system software agent 1560 during the discussion will be rendered as text in the speech bubble unless the round-table event system software avatar is enabled to respond to the question aurally. Although it is anticipated that the round-table event system software agent 1560 will have the capability of aural speech, this embodiment implies both the additional aural speech discussion capability as well as the textual discussion capability via the example of the feedback signal rendered as visual text.

Figure 16:
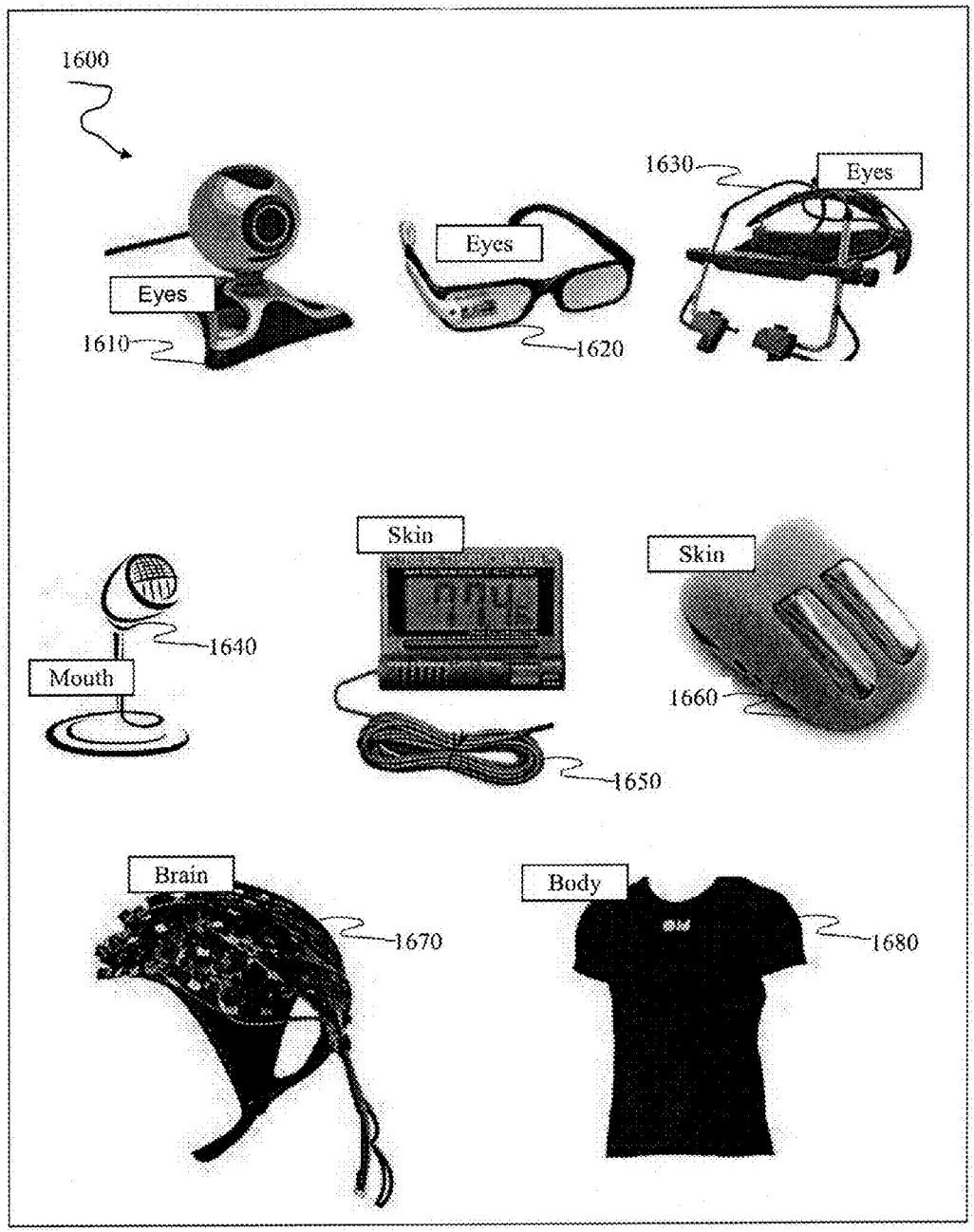
FIG. 16 is a diagram of biofeedback devices worn or directly accessed by participants that capture biofeedback data from the participants that is used by the Biofeedback Discussion System to alter their speech (utterances) during a discussion.

FIG. 16 includes examples of applicable biofeedback devices used by humans to measure their physiological activity for example as in brainwaves, heart function, breathing, muscle activity, and skin temperature. The devices are a standard digital video camera 1610, Google™ Glass™ 1620, an eye tracking headset 1630, a standard microphone 1640, a stress or hand temperature thermometer 1650, a galvanic skin response GSR2 Biofeedback Relaxation System 1660, a noninvasive optical brain and tissue monitoring system (TechEn CW6 System) 1670, and an OM™ T-shirt with sensors 1680. In FIG. 16 are biofeedback devices worn or directly accessed by human participants e.g., 301A, 301B . . . 301N that capture biofeedback data from the human participants that is used by the Biofeedback Discussion System e.g., 130 to alter their discussion.

A standard digital camera 1610 captures still (not moving) and moving images that may be of interest as sources of biosignal data from a human participant. Preferred embodiments are most likely to employ video cameras that produce moving images. Video cameras will be used to intake biofeedback information from human participants e.g., 301A-301N including but not limited to: detection facial expression, body gestures as in wiggling the body, raising or waving the hands and/or arms, finger pointing, and standing up, sitting down, or moving to another location. Video signals from the video camera are communicated via the communication link e.g., 120 to the Discussion Altering Machine e.g., 135 for analysis. Cameras must output industry standard file formats for video including but not limited to VP8™, VP9™, VP6™, Sorenson Spark, Screen video, Screen video 2, H.264, H.262/MPEG-2 Part 2 or MPEG-1 Part 2, Theora, Dirac™, AVI, Quicktime, Windows™ Media Video™, Windows Media Video Screen™, Windows™ Media Video Image™, RealVideo™, Variant of Motion JPEG, MPEG-4 Part 2, MPEG-2, MPEG-1, MPEG-1 part 2, H.262, H.263, and Adobe™ Flash™ Platform.

The standard digital camera 1610 also captures an audio component of a digital video file that can be analyzed and used by the Discussion Altering Machine e.g., 135. These audio formats that may be coupled with the video feed may include Vorbis, Opus™, MP3™, ADPCM, Nellymoser, Speex™, AAC™, PCM™, DTS™, MPEG-1, Audio Layer II (MP2™), or Dolby Digital™ (AC-3™), FLAC™, Windows™ Media Audio, Sipro™ ACELP™.net, RealAudio™, Variant of IMA™, ADPCM, Advanced Audio Coding™, MP3™, MPEG-1 Audio Layer I, MPEG-1 Audio Layer I, MPEG-1 Audio Layer III (MP3), MPEG-2 Part 3, Dolby Digital™, AMR-NB, AMR-WB, AMR-WB+, AAC-LC, HE-AAC v1 or Enhanced aacPlus (HE-AAC v2), EVRC™, SMV™ or VMR-WB, SWF™, F4V, and ISO™ base media file format.

Another example of a video capture device is Google™ Glass™ 1620, a device worn over the eyes like glasses. The glasses pair, or connect, to a smartphone using the Bluetooth wireless technology. Using an Android smartphone for Google™ Glass embodiments is preferable. Participants e.g., 301A-301N can see other participants, depending on whether the embodiment includes more than one human participant. While at the same time the Google™ Glass takes a photograph or records video from a 5-megapixel camera mounted on the glasses. A participant activates taking a video using Google™ Glass using the touch sensitive arm of the glasses or using voice commands.

An eye-tracking headset 1630 is used to detect pupil dilation that signifies cognitive load or mental concentration (Daniel Kahneman, *Thinking Fast and Slow* (New York: Farrar, Straus, and Giroux, 2011).) and to detect eye movement to determine a participant's cognitive reaction signifying telling the truth or lying. The method of detecting eye movement is as follows: the pupil is surrounded by two sets of muscles, a circular set and a radial set; the circular muscles react to the presence or absence of light; the radial muscles react when a person exerts mental effort; the Index of Cognitive Activity (ICA) measures pupil changes resulting from mental effort (radial muscles) while factoring out the light reflex (circular muscles). When using eye movement measures to determine a participant's likelihood of telling the truth or lying, eye-tracking technology measures the person's cognitive reaction. Measurements indicating this cognitive reaction include pupil dilation, response time, reading and rereading time, and errors. It has been found that lying takes more effort than telling the truth, so signs as in dilated pupils or taking longer to read and answer the question may be indicative of this extra effort.

A standard microphone 1640 is used by participants to capture their portions of speech and any ambient sounds nearby. It may be a separate piece of equipment as represented in the image 1640 or it may be included as a component in another device including but not limited to a computing device, a smartphone, voice recorder, or audio/visual conferencing device. Audio formats may include but are limited to .3gp, .aa, .aac, .aax, .act, .aiff, .amr, .ape, .au, .awb, .dct, .dss, .dvf, .flac, .gsm, .iklax, .ivs, .m4a, .m4b, .m4p, .mmf, .mp3, .mpc, .msv, .ogg, .oga, mogg, .opus, .ra, .rm, .raw, .sln, .tta, .vox, .wav, .wma, .wv, .webm.

A stress or hand temperature thermometer 1650 can be used by participants to measure their level of stress during a discussion. Another application that can be used by participants is to support the detection of lying wherein if a participant's hands are cold, it can signify extreme stress that can occur when a participant is lying. To use the device, the participant affixes a high sensitivity small bead thermal sensor to a finger of either hand using a band, tape, or other suitable means. The stress thermometer takes skin temperature readings at the point of contact of the sensor. A reading of less than 80° signifies the hand of the participant is cold and that the participant is either tense (stressed) or lying or both. A reading of between 80° to 90° still signifies some stress or anxiety on the part of the participant, but towards the higher end of this range the participant is likely to feel and behave more calmly. A reading of over 90° signifies that the person is relaxed and calm. Baseline readings over multiple discussions may be indicated as some participants may typically have warmer or colder hands on any given day as is their nature.

The GSR2 Biofeedback Relaxation System 1660 is a single channel galvanic skin resistance monitor that measures minute changes in skin pore size and sweat gland activity as it relates to tension. The GSR2 provides a relative measure of skin conductance, as opposed to an absolute measure. For relaxation purposes, one only needs an indication of whether a physiological signal is going up or down. Embodiments where participants would find it helpful in using the GSR2 would like be in meetings or in educational settings to help maintain relaxation while learning new information.

A noninvasive optical brain and tissue monitoring system 1670 is worn on the head of the participant. The TechEn CW6 System shown here is used an example of a brain monitoring system although other brain monitoring systems may provide equal or superior functionality to supply brain biofeedback signals. This brain biofeedback device applies to many embodiments due to the large number of source and detector channels; low cost; safe, non-ionizing radiation; portability; and ease of setup for participants. The primary benefit of more signal channels is improved spatial resolution and dense-array whole-head coverage. Using NIRS (near-infrared spectroscopy), Optical imaging at centimeter depths is afforded by the relationship of the absorption spectra of water, oxygenated hemoglobin (HbO) and deoxygenated hemoglobin (Hb), the three primary absorbers in tissue at near-infrared wavelengths. The water spectrum at those wavelengths permits a "spectral window" in the background absorption allowing investigators to see the hemoglobin. Moreover, within this window, the spectra of oxygenated and deoxygenated hemoglobin are distinct enough to allow spectroscopy and recovery of separate concentrations of both types of molecules. The scattering properties of different tissue types are similarly distinct. Using diffuse optical imaging, three-dimensional spatial variations in blood parameters can be reconstructed: including hemoglobin concentration and oxygen saturation as well as tissue scattering characteristics to detect and monitor meaningful brain activity during a discussion.

OM™ T-shirt 1680 is worn by a participant as a T-shirt would normally be worn. The T-shirt contains sensors woven into the fabric of the T-shirt that detect a participant's heart rate and breathing rate as well as other biofeedback measurements that do not apply to discussion embodiments.

Figure 17:
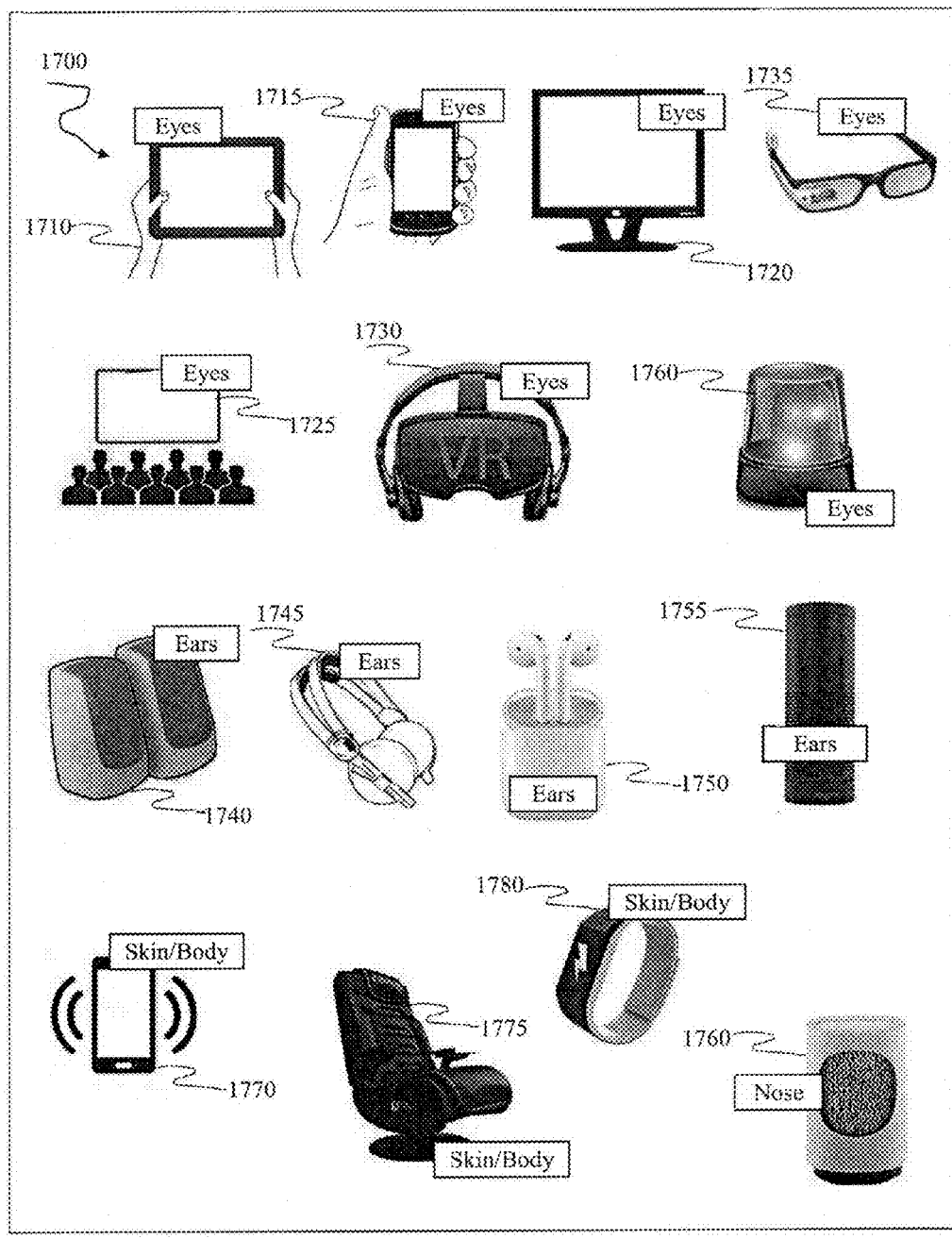
FIG. 17 is a diagram of biofeedback devices worn or directly accessed by human participants that render biofeedback data from the Biofeedback Discussion System to the human participants, altering their speech during a discussion.

FIG. 17 includes examples of applicable biofeedback devices that use feedback signals generated by the Discussion Altering Machine e.g., 320 to render biofeedback signals to participants to view, hear, smell, or feel. The devices are a table display 1710, a smartphone display 1720, a computer monitor display 1720, a projector display screen or large screen monitor (TV) 1725, a virtual reality (VR) or augmented reality (AR) headset 1730, Google™ Glass™ 1735, Computer speakers or multimedia speakers 1740, headphone 1745, Apple™ AirPod™ 1750, Amazon™ Echo™ 1755, an aromatherapy device 1760, a flashing light 1765, a vibrating smartphone 1770, the Ace Bayou™ XRocker™ vibrating chair 1775, and the Pavlok™ wristband 1780.

The biofeedback devices are worn or directly accessed by human participants e.g., 301A, 301B . . . 301N that render biofeedback data from the Biofeedback Discussion System e.g., 130 to the human participants, altering their discussion.

A hand held tablet visual display device 1710 is often used by participants in a variety of situations where a computer monitor is cumbersome and a smartphone is considered to have too small a display area to suit the participant's needs. A tablet is a thin, flat mobile computer with a touchscreen display, processing circuitry, and a rechargeable battery in a single device. They are often equipped with sensors, including digital cameras, a microphone, and an accelerometer. The touchscreen display uses the recognition of finger or stylus gestures to replace the mouse, trackpad and keyboard used in laptops. They usually feature on-screen, pop-up virtual keyboards for typing and inputting commands. Tablets may have physical buttons for basic features including speaker volume and power, and ports for plugging in network communications, headphones and battery charging. Tablets are typically larger than smartphones or personal digital assistants with screens 7 inches (18 cm) or larger, measured diagonally. Tablets have Wi-Fi capability built in so that users can connect to the Internet and can have cellular network capabilities. Tablets would be most appropriate for participants to use in embodiments including but not limited to meetings, conferences, seminars, webinars, round-table discussions, and educational environments although other embodiment's visual displays can well be configured to function on a tablet.

A smartphone visual display device 1715 is commonly used as an alternate visual aid when participants are part of a larger group viewing rendered visual feedback signals. A smartphone is a mobile phone with an advanced mobile operating system which combines features of a personal computer operating system with other features useful for mobile or handheld use. Smartphones, which are usually pocket-sized, typically combine the features of a cell phone with those of other popular digital mobile devices like personal digital assistants (PDAs), including but not limited to an event calendar, media player, video games, GPS navigation, digital camera and digital video camera. Most smartphones can access the Internet and can run a variety of third-party software components ("apps"). They typically have a color display with a graphical user interface that covers 70% or more of the front surface. The display is often a touchscreen, which enables the user to use a virtual keyboard to type words and numbers and press onscreen icons to activate "app" features. Participants using a smartphone may be limiting for some embodiments, yet it is anticipated that embodiments will be smartphone enabled for some if not all functionality. Preferred embodiments where participants use a smartphone to access a visual feedback signal include dating, education uses, and some meeting, conference, seminar, and webinar uses.

A computer monitor or a computer display 1720 is an electronic visual display for computers. A monitor usually comprises the display device, circuitry, casing, and power supply. The display device in modern monitors is typically a thin film transistor liquid crystal display (TFT-LCD) or a flat panel LED display, while older monitors used a cathode ray tubes (CRT). It can be connected to the computer via VGA™, DVI™, HDMI™, DisplayPort™, Thunderbolt™, LVDS (Low-voltage differential signaling) or other proprietary connectors and signals. A computer monitor is deemed as being a suitable device for visual biofeedback signal rendering for all embodiments.

A projector display screen 1725 or large screen monitor (TV) is often used when presenting visual feedback signals to a group of participants. A projection screen is an installation consisting of a surface and a support structure used for displaying a projected image for the view of an audience. Projection screens may be permanently installed, as in a movie theater; painted on the wall; or portable with tripod or floor rising models as in a conference room or other non-dedicated viewing space. Large-screen televisions use thin screen technologies including liquid crystal display (LCD), plasma display (PDP) and Digital Light Processing (DLP). Recently released technologies like organic light-emitting diode (OLED) and not-yet released technologies like surface-conduction electron-emitter display (SED) or field emission display (FED) are making their way to replace the first flat screen technologies in picture quality. The diagonal screen size of a CRT television is limited to about 40 inches because of the size requirements of the cathode ray tube, which fires three beams of electrons onto the screen, creating a viewable image. A larger screen size requires a longer tube, making a CRT television with a large screen (50 to 80 inches) unrealistic because of size. Large screen TVs or projector display screens are most applicable to larger group discussions as would occur in meeting, conference, seminar, and round-table embodiments, yet other envisioned embodiments may also find the larger size of the display of the visual feedback signal helpful.

Virtual reality (VR) or augmented reality (AR) headsets are both represented by 1730. The specific functionality used by participants wearing the VR or AR headset is described in each embodiment example. Augmented reality is a live direct or indirect view of a physical, real-world environment whose elements are augmented (or supplemented) by computer-generated sensory input including but not limited to sound, video, graphics or GPS data. It is related to a more general concept called mediated reality, in which a view of reality is modified (possibly even diminished rather than augmented) by a computer. As a result, the technology functions by enhancing one's current perception of reality. By contrast, virtual reality replaces the real world with a simulated one. Augmentation is conventionally in real-time and in semantic context with environmental elements. Information about the environment and its objects is overlaid on the real world. This information can be virtual or real, e.g. seeing other real sensed or measured information. Augmented reality brings out the components of the digital world into a person's perceived real world. One example is an AR Helmet for construction workers which displays information about the construction sites. Many embodiments would lend themselves to AR or VR views of the rendered biofeedback signals including invention, dating, meeting, conference, seminar, round-table, and educational discussions.

The Google™ Glass™ 1735 is a device worn over the eyes like glasses. Google™ Glass is currently limited in its display size capability, but does provide the ability to render visual notifications to a participant. Current embodiments where Google™ Glass is helpful in a discussion include dispute mediation, meetings, conferences, seminars, and round-tables. It is anticipated that other embodiments may find future features of Google™ Glass™ helpful when rendering feedback signals to a participant.

Computer speakers 1740, or multimedia speakers, are speakers sold for use with computers, although usually capable of other audio uses, e.g. for an MP3 player. Most such speakers have an internal amplifier, and consequently require a power source, which may be by a main power supply often via an AC adapter, batteries, or a USB port (able to supply no more than 2.5 W DC, 500 mA at 5V). The signal input connector is often a 3.5 mm jack plug (usually color-coded lime green per the PC 99 standard); RCA connectors are sometimes used, and a USB port may supply both signal and power (requiring additional circuitry, and only suitable for use with a computer). Battery-powered wireless Bluetooth speakers require no connections at all. Most computers have speakers of low power and quality built in; when external speakers are connected they disable the built-in speaker.

Headphones 1745 are a pair of small listening devices that are designed to be worn on or around the head over a user's ears. They are electroacoustic transducers, which convert an electrical signal to a corresponding sound in the user's ear. Headphones are designed to allow a single user to listen to an audio source privately, in contrast to a loudspeaker, which emits sound into the open air, for anyone nearby to hear. Headphones are also known as earspeakers, earphones or, colloquially, cans. Circum-aural and supra-aural headphones use a band over the top of the head to hold the speakers in place. In the context of telecommunication, a headset is a combination of headphone and microphone. Headphones connect to a signal source; for example an audio amplifier, radio, CD player, portable media player, mobile phone, video game console, or electronic musical instrument, either directly using a cord, or using wireless technology including hut not limited to Bluetooth or FM radio.

The Apple™ AirPod™ 1750 is a set of wireless earbuds for the iPhone 7. The Bluetooth-based AirPods, when placed in the ear, the AirPod's W1 processor provides the intelligence to connect automatically to the iPhone or Apple Watch, and double tapping the AirPods activates Siri. Earbuds or earphones consist of individual units that plug into the user's ear canal. AirPods use optical sensors and a motion accelerometer to detect when they're in your ears. The W1 chip automatically routes the audio and engages the microphone. And when are in a discussion, an additional accelerometer works with beamforming microphones to filter out background noise and focus on the sound of your voice. Embodiments envisioned that would find the AirPod useful include invention, dispute mediation, dating, meetings, conferences, seminars, webinars, round-table discussions, and all educational embodiments as the AirPod enables privacy for the participant in a discussion.

The Amazon™ Echo™ 1755 is a smart, wireless speaker. It combines a wireless speaker, music streamer and virtual assistant in one unit. The device consists of a 9.25-inch (23.5 cm) tall cylinder speaker with a seven-piece microphone array. The device is capable of voice interaction and other applications unrelated to embodiments herein. It can also control several smart devices using itself as a home automation hub. In the default mode the device continuously listens to all speech. Echo requires a Wi-Fi internet connection in order to work. Echo's voice recognition capability is based on Amazon Web Services and the Amazon common voice platform. It is envisioned that Echo may play a part in embodiment examples including but not limited to invention, dispute mediation, meetings, conferences, seminars, round-table discussions, and some educational discussions where more than one participant is co-located during their discussion.

An electronic aromatherapy device 1760 is used to alter human moods. In embodiments where emotion and mood play a significant role including but not limited to dispute mediation, dating, and educational discussions, the effect of aroma feedback signals can alter a discussion. When you smell lemon oil, some molecules dissolve in the mucus lining of the olfactory epithelium on the roof of the nasal cavity. There, the molecules stimulate olfactory receptors. Olfactory sensory neurons carry the signals from the receptors to the olfactory bulb, which filters and begins processing the input signals of the lemon scent. Mitral cells then carry the output signals from the olfactory bulb to the olfactory cortex, which allows you to perceive and recognize the tangy scent of lemon. Interestingly, the mitral cells do not only lead to the olfactory cortex, they also carry the signals from the lemon scent to other areas in the brain's limbic system. Some mitral cells connect directly to the amygdala, the brain structure involved in emotional learning and memory. Indeed, the olfactory system is the only sensory system that involves the amygdala and the limbic system in its primary processing pathway.

A flashing light 1765 is a light showing one or more flashes at regular intervals, the duration of the light period is less than that of the dark period. In particular, a light showing a single flash at regular intervals; distinctive names are used to indicate different combinations of flashes.

A smartphone 1770 depicted in vibration mode is a typical smartphone capability. Mobile phones are made to vibrate by a very small electric motor with an eccentrically mounted (off-center) weight on the shaft. When the motor spins, this unbalanced weight makes the phone vibrate. The motors that are used in mobile phones really are tiny: some of them aren't much bigger than 4 mm across and maybe 10 mm long, with a shaft well under 1 mm in diameter. Embodiments where a vibration feedback signal emanating from a smartphone may be useful include invention, dispute mediation, meetings, conferences, seminars, webinars, round-table discussions, and educational discussions.

An Ace Bayou™ XRocker™ 1775 is a vibrating chair that is currently used by eGame players (video garners) and when watching video or movies. These chairs use Audio Force Modulation Technology (AFM) which means you can feel the sound vibrating from inside the hollow of the chair.

In embodiments where special seating can be provided by either the participant or by the organization holding group events the vibrating feedback signal provided to the participant can alter their discussion. Embodiments where vibration feedback signal emanating from the participant's seat may be useful include invention, dispute mediation, meetings, conferences, seminars, webinars, round-table discussions, and educational discussions.

A Pavlok™ wristband 1780 provides feedback signals including electro shock, beeping, vibrating, light, and textual notifications. Features of the wristband include an accelerometer that your activity and inactivity patterns, a real-time haptic feedback including vibration, sound, and LEDs operational via Bluetooth 4.0. A static shock circuit delivers up to 340V of electric current as the default setting; yet this setting is adjustable. Embodiments envisioned where participants may find a more noticeable feedback signal during a discussion may include dispute mediation, dating, and educational discussions . . . .

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of using an artificial intelligence (AI) system to establish a biofeedback loop to assist in altering a discussion in which a participant is participating, the method comprising automatically executing a biofeedback loop having the following steps during the discussion:
   in at least near real-time;
      electronically receiving speech from the participant;
      using a discussion altering machine to derive an appended portion of speech from (a) the received speech and (b) profile information about the participant;
      electronically submitting the appended portion of speech to the AI system;
      receiving from the AI system at least one of a suggested new concept or group goal that is relevant to the discussion;
      using a combination of (a) the at least one new concept or group goal and (b) an expression characteristic of a portion of the speech, to produce at least a first electronic feedback signal that includes a rendering of the at least one new concept or group goal as part of a computer generated graphical user interface;
      providing the first electronic feedback signal to the participant to elicit a physical response from the participant;
   using an electronic sensor to sense the physical response, and using the physical response as a subsequent expression characteristic in the biofeedback loop; and
   wherein each of the expression characteristic and the subsequent expression characteristic is selected from the group consisting of a hand gesticulation, a facial expression, a heart rate, a breathing rate, a brain wave, an eye movement, a pupil dilation, a body temperature, a pore size, an auditory tone, a word delivery speed, a loudness, and an accent, all with respect to the participant.

2. The method of claim 1, wherein the AI system comprises IBM™ Watson™.

3. The method of claim 1, wherein the at least one new concept includes multiple concepts and ranking the multiple concepts.

4. The method of claim 3, wherein the step of rendering of the at least one new concept includes providing the participant with a visual representation of the multiple concepts and their respective rankings.

5. The method of claim 1, wherein the first electronic feedback signal comprises a vibration that is tactilely appreciable to a human, and further comprising applying the vibration to a portion of the participant's body.

6. The method of claim 5, wherein the vibration has a frequency and is applied at an intensity, which is sufficient to elicit a pain response that is perceived by the participant.

7. The method of claim 1, further comprising eliciting from the participant a first goal relating to the discussion.

8. The method of claim 7, further comprising using the AI system to identify the at least one concept based at least in part on both the appended portion of speech and the first goal.

9. The method of claim 7, further comprising rendering a second feedback signal to the participant as a function of an extent to which the appended portion of speech relates to the first goal.

10. The method of claim 7, further comprising receiving a second goal from a second participant, and providing the second feedback signal, subsequent to the first electronic feedback signal, to at least one of the first and second participants as a function of an extent to which the appended portion of speech relates to a consolidated goal derived from the first and second goals.

11. The method of claim 7, further comprising applying semantic analysis to the first goal to derive topic words.

12. The method of claim 11, further rendering to the participant a representation of a comparison of the at least one concept with the topic words.

13. The method of claim 7, further comprising deriving deliverable words from the first goal, and using the deliverable words to remind the participant of the goal.

14. The method of claim 1, wherein the expression characteristic is used to provide a second signal to the participant as a function of an extent to which the appended portion of speech relates to the goal.

15. The method of claim 1, wherein the expression characteristic is selected only from the group consisting of the heart rate, the breathing rate, the brain waves, the eye movement, the pupil dilation, the body temperature, and the pore size.

16. The method of claim 1, wherein the expression characteristic is selected only from the group consisting of an auditory tone, a word delivery speed, and a loudness.

17. The method of claim 1, wherein the expression characteristic is an accent.

18. The method of claim 1, wherein a second participant to the discussion comprises a computer system.

19. The method of claim 1, further comprising, receiving from the participant at least one of the appended portion of speech and goal information, as typed text entered by the participant.

20. The method of claim 1, further comprising using the first electronic feedback signal to indicate to the participant an extent to which the portion of the speech relates to the at least one concept.

21. The method of claim 1, further comprising receiving the profile information about the participant, and conveying the profile information to the AI system.

22. The method of claim 1, further comprising using an augmented reality headset to convey a composite image to the participant, the composite image including (a) a representation of another participant engaged in the discussion, and (b) a representation of profile information about the other participant.

* * * * *